(12) United States Patent
Steynberg et al.

(10) Patent No.: US 10,889,762 B2
(45) Date of Patent: Jan. 12, 2021

(54) PROCESS FOR OPERATING A HIGHLY PRODUCTIVE TUBULAR REACTOR

(71) Applicant: VELOCYS TECHNOLOGIES LIMITED, Harwell (GB)

(72) Inventors: Andre Steynberg, Dublin, OH (US); Bin Yang, Columbus, OH (US); Ravi Arora, New Albany, OH (US); Laura Silva, Dublin, OH (US); Heinz Robota, Dublin, OH (US); Sean Fitzgerald, Columbus, OH (US); Paul Neagle, Westerville, OH (US); Jason Robinson, Columbus, OH (US); Paul Schubert, Dublin, OH (US); Steven Perry, Marysville, OH (US)

(73) Assignee: VELOCYS TECHNOLOGIES LIMITED, Oxfordshire (GB)

( * ) Notice: Subject to any disclaimer, the term of this patent is extended or adjusted under 35 U.S.C. 154(b) by 0 days.

(21) Appl. No.: 16/328,029

(22) PCT Filed: Dec. 8, 2017

(86) PCT No.: PCT/US2017/065446
§ 371 (c)(1),
(2) Date: Feb. 25, 2019

(87) PCT Pub. No.: WO2018/107110
PCT Pub. Date: Jun. 14, 2018

(65) Prior Publication Data
US 2019/0284479 A1  Sep. 19, 2019

Related U.S. Application Data

(60) Provisional application No. 62/432,480, filed on Dec. 9, 2016, provisional application No. 62/432,450, filed on Dec. 9, 2016.

(51) Int. Cl.
| | | |
|---|---|---|
| C07C 1/00 | (2006.01) |
| C10G 2/00 | (2006.01) |
| B01J 4/00 | (2006.01) |
| B01J 8/06 | (2006.01) |
| B01J 23/75 | (2006.01) |
| B01J 35/02 | (2006.01) |
| B01J 35/10 | (2006.01) |
| B01J 38/12 | (2006.01) |
| B01J 38/10 | (2006.01) |
| C07C 1/04 | (2006.01) |
| B01J 38/04 | (2006.01) |

(52) U.S. Cl.
CPC .............. *C10G 2/341* (2013.01); *B01J 4/008* (2013.01); *B01J 8/062* (2013.01); *B01J 23/75* (2013.01); *B01J 35/023* (2013.01); *B01J 35/10* (2013.01); *B01J 38/10* (2013.01); *B01J 38/12* (2013.01); *C07C 1/041* (2013.01); *C10G 2/331* (2013.01); *B01J 38/04* (2013.01); *B01J 2208/00539* (2013.01); *B01J 2208/00557* (2013.01); *B01J 2208/065* (2013.01)

(58) Field of Classification Search
CPC .......... C10G 2/341; C10G 2/331; B01J 4/008; B01J 8/062; B01J 23/75; B01J 35/023; B01J 35/10; B01J 38/10; B01J 38/12; B01J 38/04; B01J 2208/00539; B01J 2208/00557; B01J 2208/065
See application file for complete search history.

(56) References Cited

U.S. PATENT DOCUMENTS

| | | | | |
|---|---|---|---|---|
| 5,080,872 A | * | 1/1992 | Jezl ...................... B01J 8/0285 422/148 |
| 6,126,908 A | * | 10/2000 | Clawson ................ B01J 8/0278 422/626 |
| 6,211,255 B1 | * | 4/2001 | Schanke .................. B01J 19/32 518/715 |
| 6,403,660 B1 | * | 6/2002 | Espinoza .............. C07C 1/0455 518/700 |
| 6,521,565 B1 | | 2/2003 | Clavenna et al. |
| 7,012,103 B2 | * | 3/2006 | Espinoza ................... B01J 8/06 518/706 |
| 8,232,415 B2 | * | 7/2012 | Taheri ..................... B01J 8/067 549/258 |
| 8,524,787 B2 | * | 9/2013 | Ermolaev ............... B01J 8/067 518/700 |
| 8,906,970 B2 | * | 12/2014 | Gamlin .................... B01J 8/067 518/706 |

(Continued)

FOREIGN PATENT DOCUMENTS

| | | | |
|---|---|---|---|
| GB | 895 038 | 4/1962 |
| GB | 895038 A | * 4/1962 | ............. C10G 1/002 |

OTHER PUBLICATIONS

J. Field et al., I & EC Product Research Development (1964) (Year: 1964).*

(Continued)

*Primary Examiner* — Alexander R Pagano
(74) *Attorney, Agent, or Firm* — Ping Wang; Morris, Manning & Martin LLP

(57) ABSTRACT

The present technology is directed to processes for conversion of synthesis gas in a tubular reactor to produce a synthetic product that utilizes high activity carbon monoxide hydrogenation catalysts and a heat transfer structure that surprisingly provides for higher per pass conversion with high selectivity for the desired synthetic product without thermal runaway.

15 Claims, 35 Drawing Sheets

(56) References Cited

U.S. PATENT DOCUMENTS

| | | | | |
|---|---|---|---|---|
| 8,959,769 B2* | 2/2015 | Gauthier | ............... | F28D 7/0041 |
| | | | | 29/890.03 |
| 9,908,093 B2* | 3/2018 | Simmons | .................. | C01B 3/56 |
| 2003/0185721 A1* | 10/2003 | Wang | ..................... | C10G 2/332 |
| | | | | 422/177 |
| 2005/0281735 A1* | 12/2005 | Chellappa | ............... | C01B 3/501 |
| | | | | 423/648.1 |
| 2013/0090394 A1* | 4/2013 | Husain | ................... | C07C 7/144 |
| | | | | 518/711 |
| 2013/0190541 A1* | 7/2013 | Du Preez | ................ | C07C 17/25 |
| | | | | 570/220 |
| 2013/0210941 A1* | 8/2013 | Verhaak | ............... | B01J 23/8892 |
| | | | | 518/713 |
| 2014/0045954 A1* | 2/2014 | LeViness | ............ | B01J 37/0205 |
| | | | | 518/715 |
| 2014/0163122 A1* | 6/2014 | Ge | .......................... | C10G 3/47 |
| | | | | 518/726 |
| 2014/0213669 A1* | 7/2014 | Herrmann | ............... | E21B 17/20 |
| | | | | 518/704 |
| 2015/0225309 A1* | 8/2015 | Tsubaki | .................. | C07C 1/044 |
| | | | | 518/713 |
| 2019/0275505 A1* | 9/2019 | Bao | ...................... | B01J 29/7065 |

OTHER PUBLICATIONS

International Search Report and Written Opinion of the International Search Authority of Application No. PCT/US17/65446 dated Feb. 14, 2018.

* cited by examiner

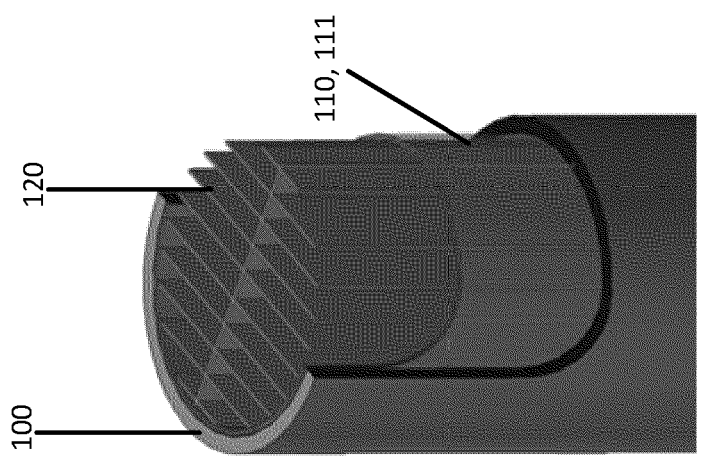
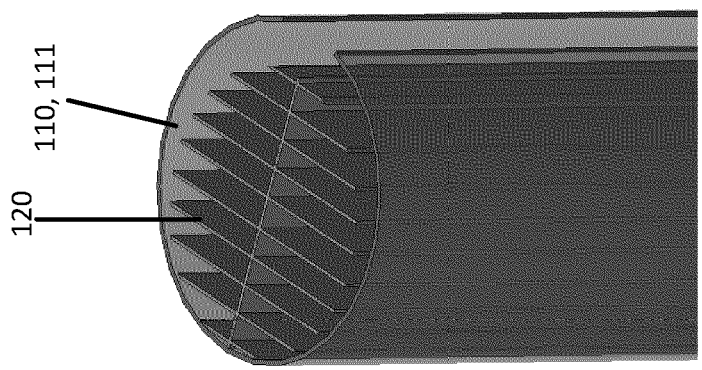
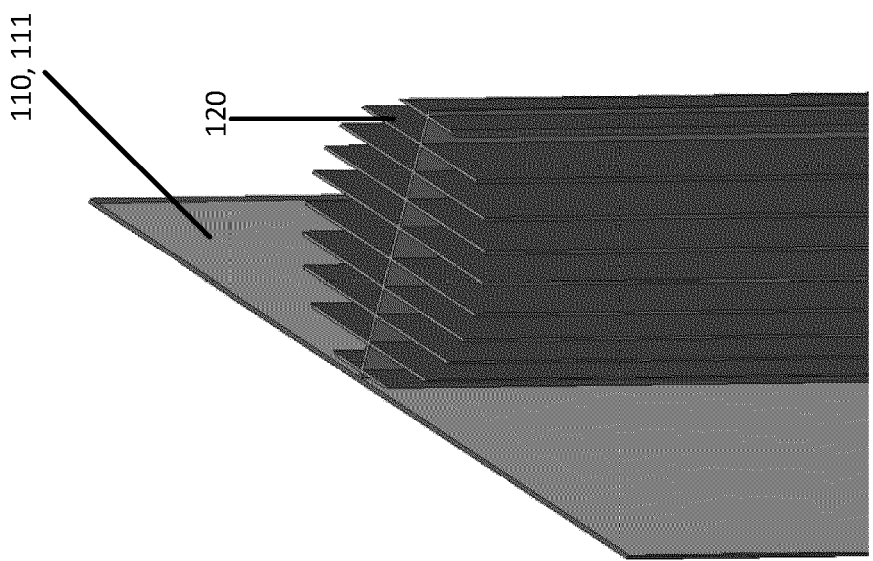
FIG. 9

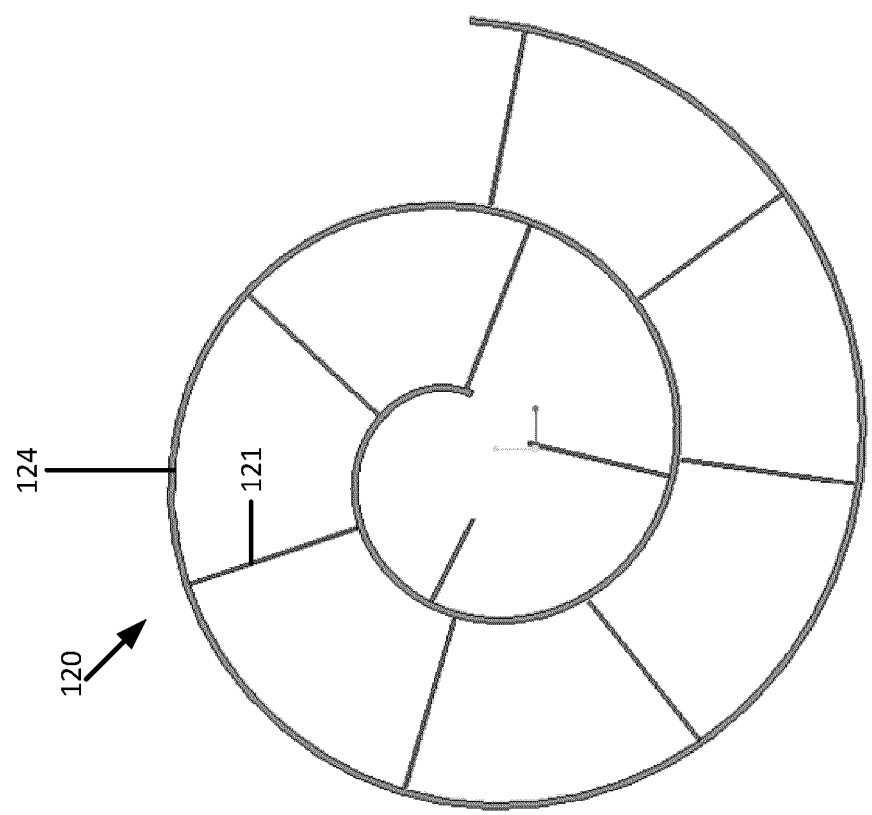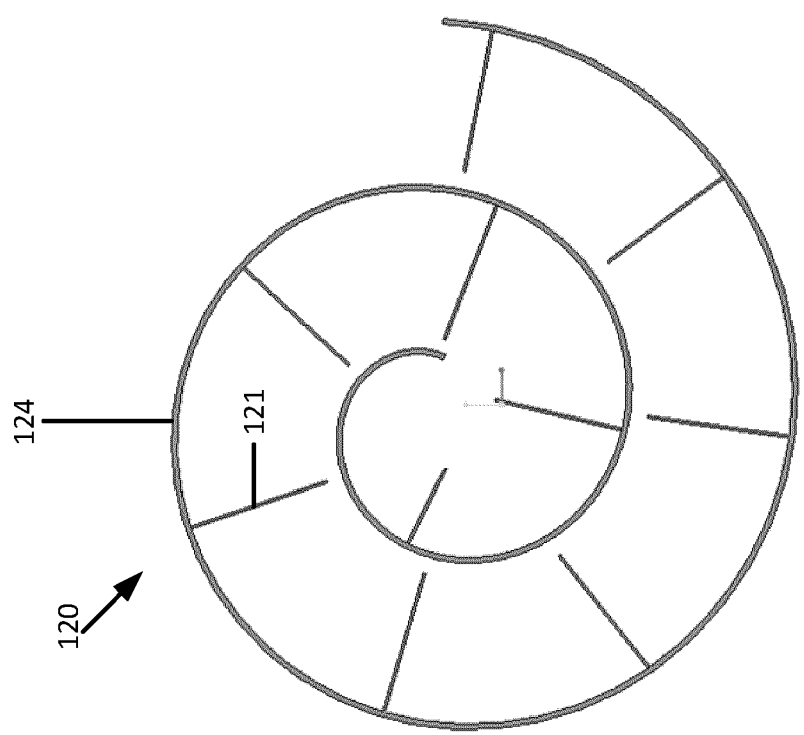
FIG. 16

US 10,889,762 B2

PROCESS FOR OPERATING A HIGHLY PRODUCTIVE TUBULAR REACTOR

CROSS-REFERENCE TO RELATED APPLICATIONS

The present application claims the benefit of priority to U.S. Provisional Application Nos. 62/432,480 and 62/432,450, each filed on Dec. 9, 2016. The contents of the foregoing applications are incorporated herein by reference in their entirety.

FIELD

The present technology generally relates to processes for conversion of synthesis gas in a tubular reactor to produce a synthetic product. The tubular reactor includes a heat transfer structure that allows for high activity carbon monoxide hydrogenation catalysts and/or higher per pass conversion with high selectivity for the desired synthetic product with shorter tube lengths compared to conventional tubular reactors.

SUMMARY

In an aspect, a process is provided for the conversion of synthesis gas. The process includes contacting in a tubular reactor a gaseous stream with a carbon monoxide hydrogenation catalyst to produce a synthetic product. The gaseous stream includes synthesis gas. The tubular reactor includes (i) a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube; (ii) a reactor outlet located downstream of the reactor inlet in fluid communication with the one or more reactor tubes; and (iii) a cooling medium in contact with the one or more reactor tubes. The diameter of the inner tube wall is from 20 mm to 80 mm. The heat transfer structure includes a network of heat conducting surfaces in conductive thermal contact with a portion of the carbon monoxide hydrogenation catalyst and wherein the heat transfer structure is in at least partial conductive thermal contact throughout the surface area of the inner tube wall. The process further includes at least one of the following:

(1) a ratio of effective thermal conductivity of the heat transfer structure and the carbon monoxide hydrogenation catalyst with the inner tube wall over thermal conductivity of the carbon monoxide hydrogenation catalyst ($k_{eff}/k_{cat}$) of at least about 50:1; and (2) a total combined surface area of the heat transfer structure and inner tube wall containing the carbon monoxide hydrogenation catalyst per volume of the carbon monoxide hydrogenation catalyst (the "SA/V") from about 500 $m^2/m^3$ to about 4000 $m^2/m^3$.

Various related apparatus and methods are also described.

In an aspect, a process is provided for the production of an alkylene oxide. The process includes contacting, in a tubular reactor, a gaseous stream comprising a $C_2$-$C_4$ alkylene and an oxygen source with an alkylene oxidation catalyst to produce a synthetic product comprising the alkylene oxide. The tubular reactor includes (a) a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the alkylene oxidation catalyst within the reactor tube; (b) a reactor outlet located downstream of the reactor inlet in fluid communication with the one or more reactor tubes; and (c) a cooling medium in contact with the one or more reactor tubes. In the process, the diameter of the inner tube wall is from 20 mm to 80 mm; the heat transfer structure comprises a network of heat conducting surfaces in conductive thermal contact with a portion of the alkylene oxidation catalyst and wherein the heat transfer structure is in at least partial conductive thermal contact throughout the surface area of the inner tube wall containing the alkylene oxidation catalyst. The process further includes at least one of the following:

(1) a ratio of effective thermal conductivity of the heat transfer structure and the alkylene oxidation catalyst with the inner tube wall over thermal conductivity of the alkylene oxidation catalyst ($k_{eff}/k_{cat}$) of at least about 50:1; and (2) a total combined surface area of the heat transfer structure and inner tube wall containing the alkylene oxidation catalyst per volume of the alkylene oxidation catalyst (the "SA/V") from about 500 $m^2/m^3$ to about 4000 $m^2/m^3$.

Various related apparatus and methods are also described.

BRIEF DESCRIPTION OF THE DRAWINGS

FIG. 9 illustrates an example of a catalyst retention mesh being wrapped around a heat transfer structure.

FIG. 16 illustrates an example of a heat transfer structure including a heat conducting surface formed into a spiral conducting surface, and a plurality of fins extending from the heat conducting surface.

FIG. 18A is a cross-section at the highest temperature location in the reactor and FIG. 18B is a zoom-in view of the cross-section, according to the working examples.

FIG. 20A is a cross-section at the highest temperature location in the reactor and FIG. 20B is a zoom-in view of the cross-section, according to the working examples.

DETAILED DESCRIPTION

I. Definitions

Figure 1:
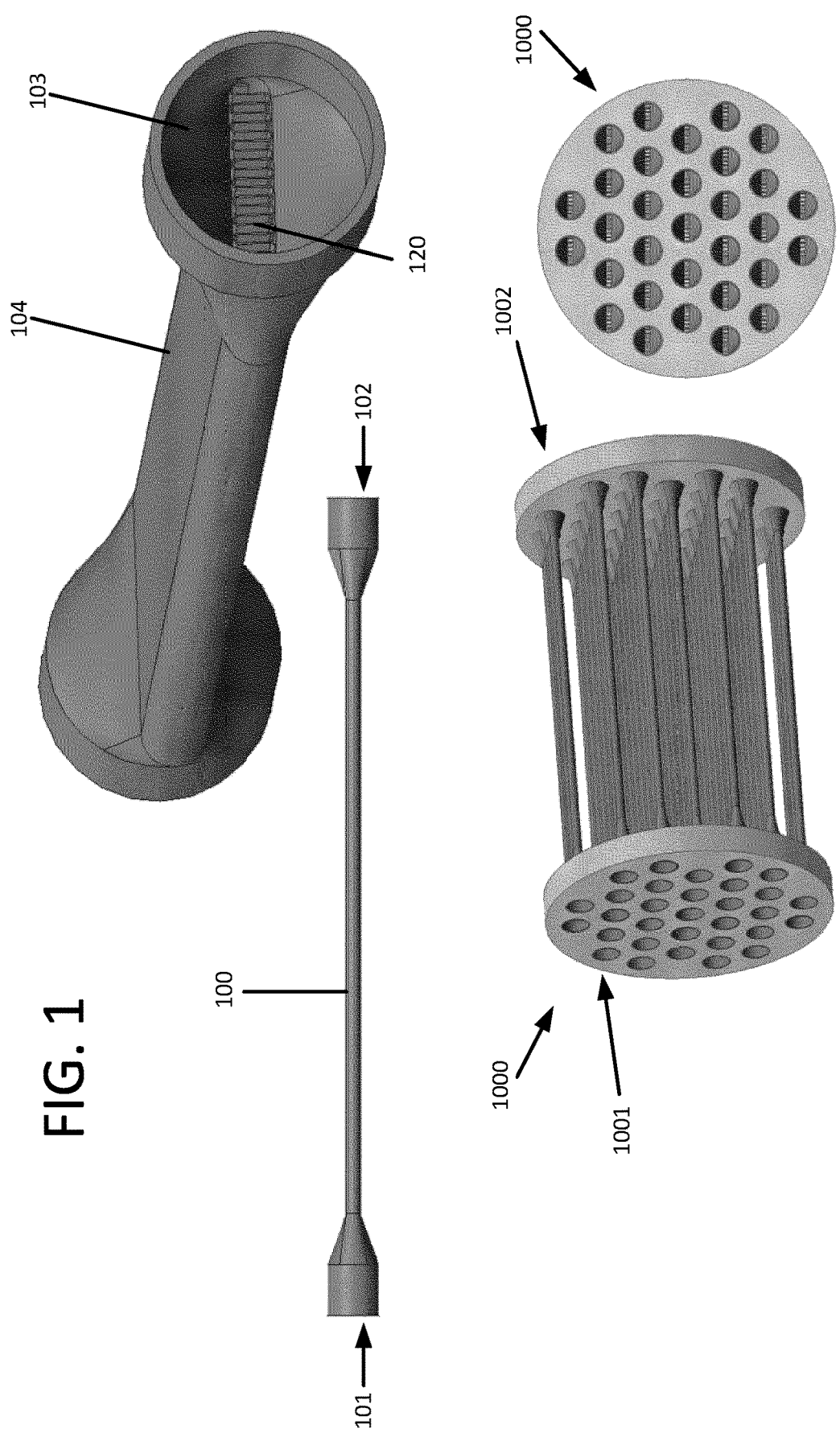
FIG. 1 illustrates a tubular reactor including a plurality of reactor tubes. In the example of FIG. 1, the reactor tube inlet and the reactor tube outlet have a same predetermined diameter, and at least a portion of the reactor tube provided between the tube inlet and the tube outlet has a diameter smaller than the predetermined diameter of the tube inlet and the tube outlet, and a heat transfer structure is provided in the form of a waveform.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As used herein, $C_m$-$C_n$, such as $C_1$-$C_{12}$, $C_1$-$C_8$, or $C_1$-$C_6$ when used before a group refers to that group containing m to n carbon atoms. For example, $C_1$-$C_4$ refers to a group that contains 1, 2, 3, or 4 carbon atoms.

Alkylenes as used herein are straight chain or branched hydrocarbons having 2 to about 20 carbon atoms, and further including at least one double bond.

As used herein, "alkyl" groups include straight chain and branched hydrocarbon radical groups having from 1 to about 20 carbon atoms, and typically from 1 to 12 carbons or, in some embodiments, from 1 to 8 carbon atoms. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH═$CH_2$, C═$CH_2$, or C═$CHCH_3$. Alkenyl groups are not to be confused with alkylenes.

The term "halide" as used herein refers to bromine, chlorine, fluorine, or iodine.

The "primary catalytic metal" of a carbon monoxide hydrogenation catalyst refers to carbon monoxide hydrogenation catalysts with more than one catalytic metal, where the primary catalytic metal is present at a weight percent (wt %) greater than the other catalytic metals.

The term "catalyst gas hourly space velocity" refers to the total gaseous feed flow at standard conditions (0° C., 1 atm) divided by the reactor volume that contains catalyst and typically recorded in units of $hr^{-1}$. Moreover, discussion herein using the term "gas hourly space velocity" or "GHSV" is to be understood as referring to catalyst gas hourly space velocity.

A "portion" of a composition or stream, as used herein, means from about 1% to about 100% by volume of the composition or stream, or any range including or in between any two integers from about 1% to about 100%. A "portion" of a surface means from about 1% to about 100% by surface area of the surface, or any range including or in between any two integers from about 1% to about 100%.

The term "fluid" refers to a gas, a liquid, or a mixture of a gas and a liquid, wherein the fluid may further contain dispersed solids, liquid droplets and/or gaseous bubbles. The droplets and/or bubbles may be irregularly or regularly shaped and may be of similar or different sizes.

The term "thermal contact" refers to two bodies, for example, two metals, that may or may not be in physical contact with each other or adjacent to each other but still exchange heat with each other. One body in thermal contact with another body may heat or cool the other body.

The term "conductive thermal contact" refers to two bodies, for example, two metals, where at least some minimal amount of physical contact with each other is present such that there is a conductive heat flow path between the two bodies.

The terms "upstream" and "downstream" refer to positions relative to the reactor inlet. For example, if position A is between the reactor inlet and position B, then position A is upstream of position B (and position B is downstream of position A). The terms "upstream" and "downstream" do not necessarily refer to a vertical position since the channels used herein may be oriented horizontally, vertically, or at an inclined angle, and the reactor inlet may be positioned such that the flow of a gaseous stream runs counter to the force of gravity.

II. The Present Technology

For highly exothermic synthetic processes that utilize synthesis gas, heat removal is a primary concern. For example, the Fischer-Tropsch reaction is highly exothermic and heat removal is essential to avoid thermal runaway and/or poor product selectivity. It is well appreciated to operate the Fischer-Tropsch reaction with as low a temperature as possible while achieving the target conversion and with low thermal gradients to keep the catalyst temperature substantially uniform. Different styles of reactors have emerged to manage heat removal over the past century.

The tubular fixed bed reactor is one style where heat is transferred radially to the walls of small diameter tubes (e.g., 1-10 cm) while also transferring heat to co-produced and, optionally, recycled liquids. A traditional tubular fixed bed reactor has a temperature rise of around 10-40° C., while the highly intensified microchannel reactor platform reduces thermal gradients to of the order of 1-5° C. to provide exceptional productivity. In general, lower temperature gradients are beneficial to improve selectivity to desired hydrocarbons while minimizing methane production. Such lower temperature gradients require restricting the reactant flow and/or the per pass conversion of reactants to products in order to limit the heat generated. Thus, achieving higher productivity per pass (such as by using high activity catalysts and/or relatively high concentrations of reactants) with concurrently high selectivity, in tubular reactors, is problematic because allowable thermal gradients and temperature rise are exceeded leading first to excessive methane formation and then to thermal runaway.

In the present technology, significantly higher productivity without thermal runaway is surprisingly achieved by utilizing a heat transfer structure as described herein. Where hydrocarbons are formed, this performance is exemplified in significantly higher CO conversion and significantly higher $C_5$+ hydrocarbon selectivity than in tubular reactors not in accordance with the present technology.

Accordingly, in an aspect, a process is provided for the conversion of synthesis gas. The process includes contacting in a tubular reactor a gaseous stream with a carbon monoxide hydrogenation catalyst to produce a synthetic product. The gaseous stream includes synthesis gas. The tubular reactor includes (i) a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube; (ii) a reactor outlet located downstream of the reactor inlet in fluid communication with the one or more reactor tubes; and (iii) a cooling medium in contact with the one or more reactor tubes. The diameter of the inner tube wall is from 20 mm to 120 mm. The heat transfer structure includes a network of heat conducting surfaces in conductive thermal contact with a portion of the carbon monoxide hydrogenation catalyst and wherein the heat transfer structure is in at least partial conductive thermal contact throughout the surface area of the inner tube wall. The process further includes at least one of the following:
(1) a ratio of effective thermal conductivity of the heat transfer structure and the carbon monoxide hydrogenation catalyst with the inner tube wall over thermal conductivity of the carbon monoxide hydrogenation catalyst ($k_{eff}/k_{cat}$) of at least about 50:1; and
(2) a total combined surface area of the heat transfer structure and inner tube wall containing the carbon monoxide hydrogenation catalyst per volume of the carbon monoxide hydrogenation catalyst (the "SA/V") from about 500 m$^2$/m$^3$ to about 4000 m$^2$/m$^3$.

Figure 30:
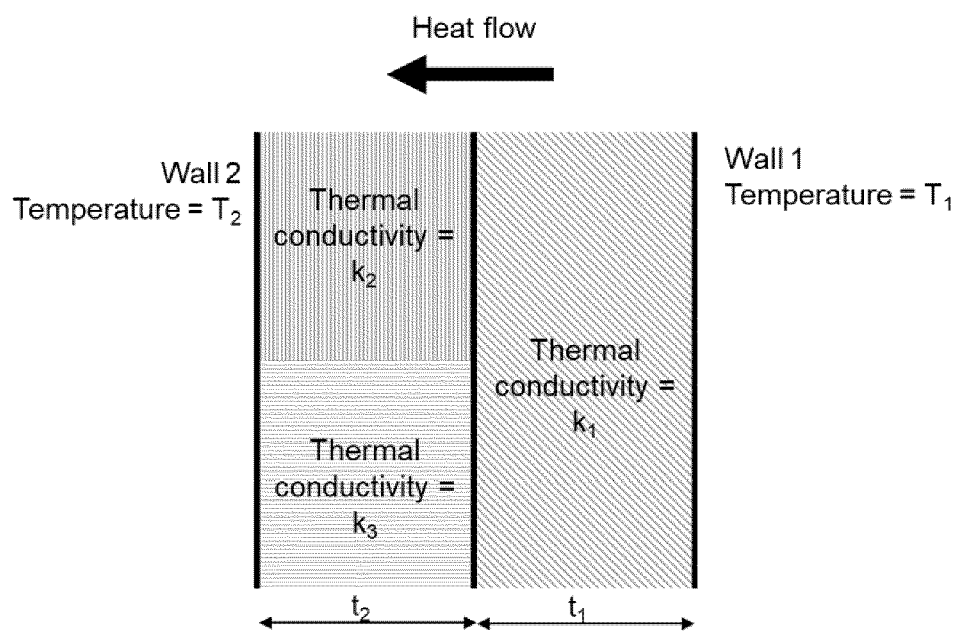
FIG. 30 shows a composite material arrangement of three materials with thermal conductivities of $k_1$, $k_2$ and $k_3$ in a 2-D Cartesian coordinate system between a Wall 1 and Wall 2, provided to aid in the discussion of effective thermal conductivity.

Effective thermal conductivity of a network of conductive media (e.g., the heat transfer structure, the carbon monoxide hydrogenation catalyst, and the inner tube wall) is a combination of series and parallel resistances. FIG. 30 shows an example of composite material arrangement of three materials with thermal conductivities of $k_1$, $k_2$ and $k_3$ in a 2-D Cartesian coordinate system between two walls (Wall 1 and Wall 2). The effective thermal conductivity between Wall 1 and Wall 2 is calculated by solving the Fourier's law for each conductive medium, where the Fourier's law is defined as:

$$Q = -kA \frac{dT}{dn} \quad \text{(Eq. 1)}$$

where Q is the steady state heat transfer, k is the thermal conductivity of the particular material, A is the cross-sectional area in the direction of n, and $$\frac{dT}{dn}$$

is the temperature gradient in the direction n. Assuming material 2 and material 3 of the FIG. 30 example are of the same dimensions, the effective thermal conductivity between Wall 1 and Wall 2 is calculated as:

$$\frac{t_1 + t_2}{k_{eff}} = \frac{t_1}{k_1} + \frac{2t_2}{k_2 + k_3} \quad \text{(Eq. 2)}$$

Figure 31:
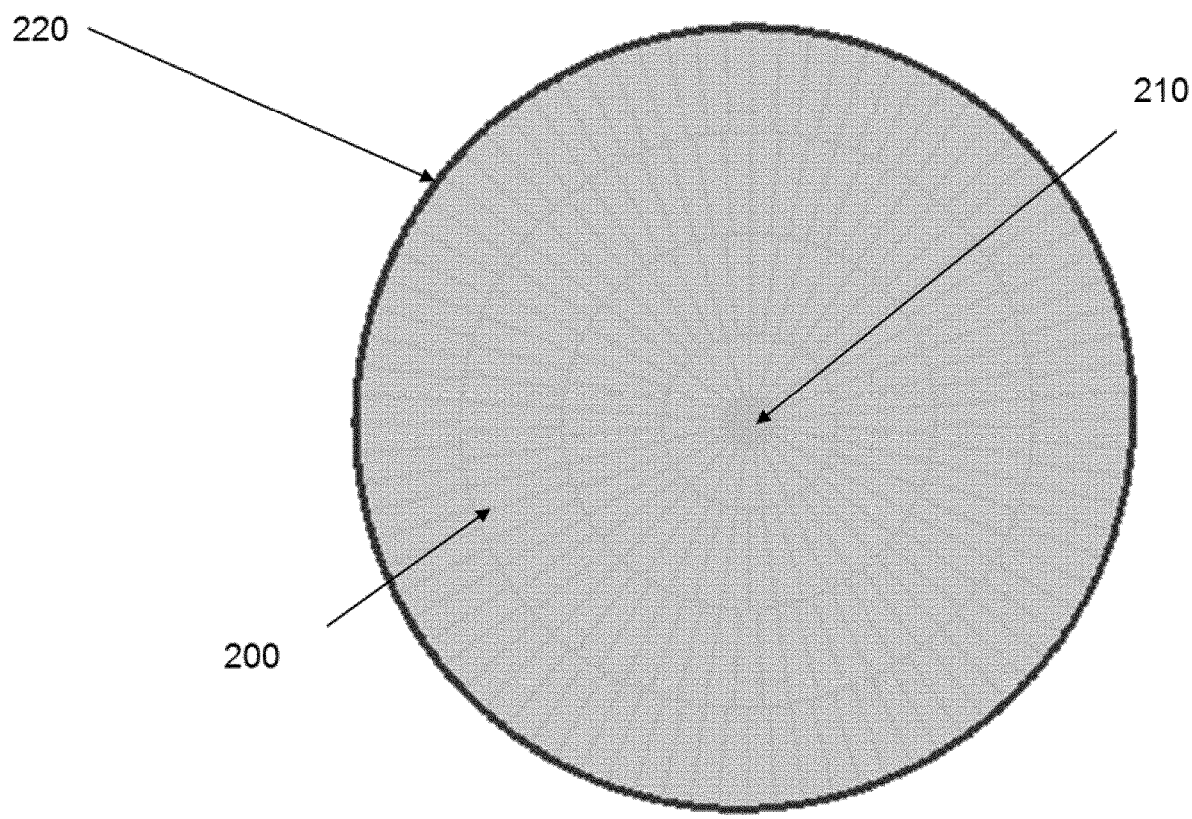
FIG. 31 illustrates a particular embodiment of the present technology as an aid in discussion of effective thermal conductivity.

As illustrated in FIG. 31 for an exemplary heat transfer structure 200 in a reactor tube of length L (length not depicted in FIG. 31) that includes a central support 210 of radius $r_1$ and an inner tube wall 220 of radius $r_2$ such that $r_2 > r_1$ and $L \gg r_2$, to calculate the effective thermal conductivity a temperature boundary condition ($T_1$) may be applied to the central support 210 and a temperature boundary condition ($T_2$) may be applied to the inner tube wall 220 such that $T_1 > T_2$. For these given boundary conditions, steady state heat transfer (Q) from the central support 210 through the heat transfer structure 200 and through the carbon monoxide hydrogenation catalyst to the inner tube wall 220 is calculated. Using this calculated Q, the effective thermal conductivity is calculated by solving Fourier's Law in cylindrical coordinates and is defined by the following equation:

$$K_{eff} = \frac{Q}{2\pi L} \left( \frac{\ln(r_1) - \ln(r_2)}{T_1 - T_2} \right) \quad \text{(Eq. 3)}$$

For a non-radial heat transfer structure, the temperature boundary conditions can be defined in a similar way to calculate steady state heat transfer. The effective thermal conductivity is calculated as follows:

$$K_{eff} = \frac{Qt}{A\Delta T} \quad \text{(Eq. 4)}$$

where Q is the calculated average steady state heat transfer rate calculated on the inner tube wall, $\Delta T$ is temperature difference, A is surface area of the inner tube wall, and t is characteristic distance between temperature boundary conditions.

The network of heat conducting surfaces themselves and/or in combination with the inner tube wall define a plurality of channels within the reactor tube containing the carbon monoxide hydrogenation catalyst. The channels may be of any cross-sectional shape, such as circular, oval, square, rhomboid, triangular, etc. The largest measurable span of the cross-sectional shape of a channel is taken to be the "channel diameter." The channels each independently have a channel diameter from about 0.01 mm to about 10 mm; thus, each channel may independently have a channel diameter of about 0.01 mm, about 0.02 mm, about 0.04 mm, about 0.06 mm, about 0.08 mm, about 0.1 mm, about 0.2 mm, about 0.4 mm, about 0.6 mm, about 0.8 mm, about 1 mm, about 1.5 mm, about 2 mm, about 2.5 mm, about 3 mm, about 3.5 mm, about 4 mm, about 5 mm, about 6 mm, about 7 mm, about 8 mm, about 9 mm, about 10 mm, or any range including and/or in between any two of these values.

The carbon monoxide hydrogenation catalyst used in the process may exhibit a conversion rate of at least about 30 millimoles CO per mL of catalyst per hour when tested by reacting a stream comprising 30 vol. % inert gas and a ratio of $H_2$/CO of 1.84 at a catalyst temperature of 205° C. (±1° C.) and a pressure of 348 psig with a catalyst gas hourly space velocity of 20,000 hr$^{-1}$ using a particulate form of the carbon monoxide hydrogenation catalyst with a weight average diameter of less than 65 µm. Such a conversion rate provided by this test protocol is hereinafter referred to as the "activity" of the carbon monoxide hydrogenation catalyst and may be described without its associated units. For example, stating that the carbon monoxide hydrogenation catalyst has an "activity of at least about 30" will be understood to mean the carbon monoxide hydrogenation catalyst exhibits a conversion rate of at least about 30 millimoles CO per mL of catalyst per hour when tested as described above. Multiple apparatus configurations well known to those skilled in the art are available for conducting such activity measurements. For example, one may use a tubular reactor of a fixed-bed type in which bed temperature is moderated by diluting the reactive catalyst with an appropriate volume of an inert thermal buffering material (see, e.g., Visconti et al., Topics in Catalysis (2011) 54:786-800; Storsxter, et al., Journal of Catalysis 231 (2005) 405-419), or, a slurry-type reactor may be used in which the suspending hydrocarbon fluid serves as the thermal buffer (see, e.g., Ma, et al., Fuel 90 (2011) 756-765). While newer to the discipline, microchannel reactors in which temperature is controlled through shortened heat-transfer distances can also be used for making activity measurements (see, e.g., Park, et al., Industrial and Engineering Chemistry Research 2016 55, 9416-9425). These conditions set the threshold value for defining a high activity catalyst. In any embodiment herein, it may be the activity of the carbon monoxide hydrogenation catalyst is from about 30 millimoles CO per mL of catalyst per hour to about 200 millimoles CO per mL of catalyst per hour. Thus, the activity of the catalyst in millimoles CO per mL of catalyst per hour may about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, or any range including and/or in between any two of these values. Examples of carbon monoxide hydrogenation catalysts with activities in the above-described ranges include, but are not limited to, those described in U.S. Pat. Publ. No. 2015/0018439, incorporated herein by reference in its entirety for any and all purposes.

The $k_{eff}/k_{cat}$ may be at least about 50:1, and may be from about 50:1 to about 2,000:1. The $k_{eff}/k_{cat}$ may be about 50:1, about 100:1, about 200:1, about 300:1, about 400:1, about 500:1, about 600:1, about 700:1, about 800:1, about 900:1, about 1,000:1, about 1,100:1, about 1,200:1, about 1,300:1, about 1,400:1, about 1,500:1, about 1,600:1, about 1,700:1, about 1,800:1, about 1,900:1, about 2,000:1, or any range including and/or in between any two of these values.

The total combined surface area of the heat transfer structure and inner tube wall containing the carbon monoxide hydrogenation catalyst per volume of the carbon monoxide hydrogenation catalyst (the "SA/V") may be from about 500 $m^2/m^3$ to about 4000 $m^2/m^3$. The SA/V may be about 500 $m^2/m^3$, about 550 $m^2/m^3$, about 600 $m^2/m^3$, about 700 $m^2/m^3$, about 800 $m^2/m^3$, about 900 $m^2/m^3$, about 1000 $m^2/m^3$, about 1100 $m^2/m^3$, about 1200 $m^2/m^3$, about 1300 $m^2/m^3$, about 1400 $m^2/m^3$, about 1500 $m^2/m^3$, about 1600 $m^2/m^3$, about 1700 $m^2/m^3$, about 1800 $m^2/m^3$, about 1900 $m^2/m^3$, about 2000 $m^2/m^3$, about 2200 $m^2/m^3$, about 2400 $m^2/m^3$, about 2600 $m^2/m^3$, about 2800 $m^2/m^3$, about 3000 $m^2/m^3$, about 3200 $m^2/m^3$, about 3400 $m^2/m^3$, about 3600 $m^2/m^3$, about 3800 $m^2/m^3$, about 4000 $m^2/m^3$, or any range including and/or in between any two of these values.

In any embodiment herein, it may be at least about 5% of the surface area of the inner tube wall containing the carbon monoxide hydrogenation catalyst is in conductive thermal contact with the heat transfer structure. The surface area of the inner tube wall containing the carbon monoxide hydrogenation catalyst in conductive thermal contact with the heat transfer structure may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or any range including and/or in between any two of these values.

The heat transfer structure may include steel, aluminum, copper, an alloy thereof, or a combination of any two or more thereof. For example, the heat transfer structure may include a combination of steel and aluminum, steel and copper, aluminum and copper, or steel, aluminum, and copper.

In any embodiment herein, the heat transfer structure may include a random network of heat conducting surfaces. In any embodiment herein, the heat transfer structure may include an ordered network of heat conducting surfaces. For example, the heat transfer structure may include a plurality of fins extending radially from a central support. It may be the heat transfer structure includes a first set of a plurality of fins extending radially from a central support to an internal circumferential wall of the heat transfer structure to define a first set of channels and a second set of a plurality of fins extending radially from the circumferential wall to the inner tube wall, wherein each fin of the second set is in conductive thermal contact with the inner tube wall to define a second set of channels. Further embodiments of heat transfer structures are described below in relation to FIGS. 1-16.

The catalyst may be segregated into separate reaction zones in the reactor tube in the direction of flow through the reactor tube. The same or different catalyst may be used in each reaction zone. For example, each reaction zone may differ from another by activity, weight average diameter, average outer surface to volume ratio, diffusion path, form of catalyst (particulate solid, extrudate), etc., or any combination of any two or more thereof. For example, the catalyst of a first reaction zone group may exhibit a higher activity than the catalyst of a second reaction zone. For example, it may be that the activity of the catalyst of the first reaction zone is at least 5% higher, at least 10% higher, at least 20% higher, at least 30% higher, at least 40% higher, or at least 50% higher than the activity of the catalyst of the second reaction zone. When a third reaction zone is employed, the third reaction zone may contain a catalyst with higher activity than the catalyst in the second reaction zone; it may be that the activity of the catalyst of the third reaction zone is at least 5% higher, at least 10% higher, at least 20% higher, at least 30% higher, at least 40% higher, or at least 50% higher than the activity of the catalyst of the second reaction zone. In any embodiment herein including two or more reaction zones, each reaction zone may be defined by a heat transfer structure. For example, a first heat transfer structure may be in contact with a first volume of catalyst and a second heat transfer structure may be in contact a second volume of catalyst, where the first and second heat transfer structures may be identical or different and/or the catalyst of the first volume is the same or different from the catalyst of the second volume.

The process may include introducing the gaseous stream through the reactor inlet at a pressure from about 250 psig to about 1,000 psig. The pressure for introducing the gaseous stream through the reactor inlet may be about 250 psig, about 350 psig, about 400 psig, about 450 psig, about 500 psig, about 550 psig, about 600 psig, about 650 psig, about 700 psig, about 750 psig, about 800 psig, about 850 psig, about 900 psig, about 950 psig, about 1,000 psig, or any range including and between any two of these values. For example, the process may include introducing the gaseous stream through the reactor inlet at a pressure from about 500 psig to about 1,000 psig, or at a pressure from about 500 psig to about 750 psig. In any embodiment herein, a ratio of $H_2/CO$ in the synthesis gas may be from about 1.6 to about 2.0. Thus, the ratio of $H_2/CO$ in the synthesis gas may be about 1.6, about 1.7, about 1.8, about 1.9, about 2.0, or any range including and/or in between any two of these values.

In regard to the reactor tube(s), each reactor tube may independently be from about 0.3 meters (m) to about 5 m in length; thus, each reactor tube may independently be about 0.3 m, about 0.4 m, about 0.5 m, about 0.6 m, about 0.7 m, about 0.8 m, about 0.9 m, about 1 m, about 1.5 m, about 2 m, about 2.5 m, about 3 m, about 3.5 m, about 4 m, about 4.5 m, about 5 m, or any range including and/or in between any two of these values. It may be each reactor tube is independently less than about 5 m. The diameter of the inner tube wall of the one or more reactor tubes is independently in each tube about 20 mm to about 120 mm. Thus, the one or more reactor tubes may each independently have an inner tube wall diameter of about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 110 mm, about 120 mm, or any range including and/or in between any two of these values.

The tubular reactor may contain from 1 to about 30,000 reactor tubes. It may be the tubular reactor includes at least 100 reactor tubes. The tubular reactor may preferably include less than about 20,000 reactor tubes. The tubular reactor may preferably include less than about 10,000 reactor tubes, more preferably less than about 5,000 reactor tubes, and even more preferably less than about 2,000 reactor tubes.

In any embodiment of the process, the contacting step may include maintaining at least about 50% carbon monoxide conversion per pass in the one or more reactor tubes, where per pass conversion of CO is defined by the difference between the inlet and outlet moles of CO divided by the inlet number of moles of CO. The carbon monoxide per pass conversion may be at least about 55%, at least about 60%, preferably at least about 65%, even more preferably at least about 70%. The carbon monoxide per pass conversion may less than about 90%, more preferably less than about 80%, to help ensure the water partial pressure is below levels that would accelerate carbon monoxide hydrogenation catalyst deactivation, such as Fischer-Tropsch catalyst deactivation.

The gaseous stream may include one or more inerts. Inerts include, but are not limited to, molecular nitrogen, helium, methane, natural gas, carbon dioxide, steam, argon, and the like, as well as any mixture of any two or more thereof. The inerts may be included from zero (i.e., no diluent is included) to about 50% by volume of the gaseous stream. Thus, the volume of inerts included in the gaseous stream may be none (i.e., 0%), about 0.1%, about 1%, about 5%, about 10%, about 15%, about 20%, about 25%, about 30%, about 35%, about 40%, about 45%, about 50%, or any range in between and/or including any two of these values.

The process described herein may include a catalyst gas hourly space velocity (GHSV) of the gaseous stream in the tubular reactor from about 5,000 $hr^{-1}$ to about 20,000 $hr^{-1}$. It may be that the catalyst gas hourly space velocity is about 5,000 $hr^{-1}$, about 6,000 $hr^{-1}$, about 7,000 $hr^{-1}$, about 8,000 $hr^{-1}$, about 9,000 $hr^{-1}$, about 10,000 $hr^{-1}$, about 11,000 $hr^{-1}$, about 12,000 $hr^{-1}$, about 13,000 $hr^{-1}$, about 14,000 $hr^{-1}$, about 15,000 $hr^{-1}$, about 16,000 $hr^{-1}$, about 17,000 $hr^{-1}$, about 18,000 $hr^{-1}$, about 19,000 $hr^{-1}$, about 20,000 $hr^{-1}$, or any range including and between any two of these values.

The temperature of the gaseous stream at the reactor inlet may be about 150° C. to about 240° C. For example, the temperature of the gaseous stream at the reactor inlet may preferably be about 160° C. to about 220° C., even more preferably about 170° C. to about 190° C.

As described above, the cooling medium is in contact with the one or more reactor tubes. The cooling medium temperature may be from about 160° C. to about 240° C., more preferably from about 180° C. to about 210° C., and even more preferably from about 190° C. to about 210° C.

A person of ordinary skill in the art will be familiar with carbon monoxide hydrogenation catalysts suitable for generating preferred synthetic products. In general, carbon monoxide hydrogenation catalysts may be porous. Carbon monoxide hydrogenation catalyst may be a particulate catalyst, where the particulate catalyst may be particulate solids, extrudates, or a mixture of the two. Extrudates may have a shape that includes at least one of cylindrical, tubular, polylobular, fluted, or ridged.

For example, where the synthetic product includes hydrocarbons, the carbon monoxide hydrogenation catalyst may include a Fischer-Tropsch catalyst. Fischer-Tropsch catalysts may include cobalt or iron, and may further include a promoter such as Cu, Mn, Pd, Pt, Rh, Ru, Re, Ir, Au, Ag, Os, or a combination of any two or more thereof. For example, the Fischer-Tropsch catalyst may include FeCuMn. The Fischer-Tropsch catalyst may also include a support material. Suitable support materials include a refractory metal oxide, carbide, carbon, nitride or a mixture of any two or more thereof. The Fischer-Tropsch catalyst may further include a surface modified support material, wherein the surface of the support has been modified by being treated with silica, titania, zirconia, magnesia, chromia, alumina, or a mixture of any two or more thereof. In any of the above embodiments, the support material may include alumina, zirconia, silica, titania, or a mixture of two or more thereof. The support material may include a $TiO_2$-modified silica. In any of the above embodiments, the surface of the surface-modified support material may be amorphous.

Where the synthetic product includes methanol, the carbon monoxide hydrogenation catalyst may include a copper-based catalyst such as $Cu/ZnO/Al_2O_3$. Where the synthetic product includes DME, the carbon monoxide hydrogenation catalyst may include a blend of a methanol synthesis catalyst, such as $Cu/ZnO/Al_2O_3$, and a dehydration catalyst, such as $\gamma\text{-}Al_2O_3$.

Where the carbon monoxide hydrogenation catalyst is a Fischer-Tropsch catalyst, the Fischer-Tropsch catalyst may be a particulate Fischer-Tropsch catalyst (such as a particulate solid catalyst, an extrudate catalyst, or a mixture of the two). Thus, for the sake of clarity, it is understood that the particulate Fischer-Tropsch catalyst may include cobalt, and may further include a promoter such as Cu, Mn, Pd, Pt, Rh, Ru, Re, Ir, Au, Ag, Os, or a combination of any two or more thereof. The particulate Fischer-Tropsch catalyst may also include a support material. Suitable support materials include a refractory metal oxide, carbide, carbon, nitride or a mixture of any two or more thereof. The particulate Fischer-Tropsch catalyst may include a surface modified support material, wherein the surface of the support has been modified by being treated with silica, titania, zirconia, magnesia, chromia, alumina, or a mixture of any two or more thereof. In any of the above embodiments, the support material may include alumina, zirconia, silica, titania, or a mixture of two or more thereof. The support material may include a $TiO_2$ modified silica. The surface of the surface-modified support material may be amorphous. Non-limiting examples of particulate Fischer-Tropsch catalysts suitable for use in the present technology are described in International Patent Pub. WO 2012/107718, incorporated herein by reference in its entirety for any and all purposes.

The particulate Fischer-Tropsch catalyst may be coated on a support structure such as a carbon nanotubes, and wherein the carbon nanotubes are disposed on a support material. The support can be made of a variety of materials such as ceramic, but where rapid heat transport is preferred, the support preferably is a thermally conductive material such as a metal. However, the present technology provides for supports where heat transport is less thermally conductive, e.g., ceramic. The support may be stainless steel, an alloy such as monel, cordierite, silica, alumina, rutile, mullite, zirconia, silicon carbide, aluminosilicate, stabilized zironia, steel and alumina-zirconia blend. For use in the present technology, U.S. Pat. No. 6,713,519 provides examples of suitable carbon nanotube-on-support materials over which a particulate Fischer-Tropsch catalyst may be coated.

Particulate carbon monoxide hydrogenation catalysts (such as particulate Fischer-Tropsch catalysts) may have a weight average diameter from about 100 micrometers (μm) to about 1 millimeter (mm). Thus, the carbon monoxide hydrogenation catalyst may be a particulate catalyst with a weight average diameter of about 100 μm, about 150 μm, about 200 μm, about 250 μm, about 300 μm, about 350 μm, about 400 μm, about 450 μm, about 500 μm, about 600 μm, about 700 μm, about 800 μm, about 900 μm, about 1 mm, or any range including and/or in between any two of these values. In any embodiment herein, the carbon monoxide hydrogenation catalyst may be a particulate catalyst having an average outer surface to volume ratio from about 3.0 $mm^{-1}$ to about 50.0 $mm^{-1}$, where such catalysts are preferably extrudates. Thus, the particulate catalyst may have an average outer surface to volume ratio of about 3.0 $mm^{-1}$, about 3.5 $mm^{-1}$, about 4.0 $mm^{-1}$, about 4.5 $mm^{-1}$, about 5.0 $mm^{-1}$, about 5.5 $mm^{-1}$, about 6.0 $mm^{-1}$, about 6.5 $mm^{-1}$, about 7.0 $mm^{-1}$, about 7.5 $mm^{-1}$, about 8.0 $mm^{-1}$, about 8.5 $mm^{-1}$, about 9.0 $mm^{-1}$, about 9.5 $mm^{-1}$, about 10.0 $mm^{-1}$, about 11 $mm^{-1}$, about 12 $mm^{-1}$, about 13 $mm^{-1}$, about 14 $mm^{-1}$, about 15 $mm^{-1}$, about 16 $mm^{-1}$, about 17 $mm^{-1}$, about 18 $mm^{-1}$, about 19 $mm^{-1}$, about 20 $mm^{-1}$, about 21 $mm^{-1}$, about 22 $mm^{-1}$, about 23 $mm^{-1}$, about 24 $mm^{-1}$, about 25 $mm^{-1}$, about 26 $mm^{-1}$, about 27 $mm^{-1}$, about 28 $mm^{-1}$, about 29 $mm^{-1}$, about 30 $mm^{-1}$, about 31 $mm^{-1}$, about 32 $mm^{-1}$, about 33 $mm^{-1}$, about 34 $mm^{-1}$, about 35 $mm^{-1}$, about 36 $mm^{-1}$, about 37 $mm^{-1}$, about 38 $mm^{-1}$, about 39 $mm^{-1}$, about 40 $mm^{-1}$, about 42 $mm^{-1}$, about 44 $mm^{-1}$, about 46 $mm^{-1}$, about 48 $mm^{-1}$, about 50 $mm^{-1}$, or any range including and/or in between any two of these values. In any embodiment herein, the carbon monoxide hydrogenation catalyst may be a particulate catalyst having a diffusion path from about 50 μm to about 500 μm; the diffusion path may be about 50 μm, about 100 μm, about 150 μm, about 200 μm, about 250 μm, about 300 μm, about 350 μm, about 400 μm, about 450 μm, about 500 μm, or any range including and/or in between any two of these values. In any embodiment herein, it may be the carbon monoxide hydrogenation catalyst is in the form of a bed of particulate solids, for example, a fixed bed of particulate solids.

In any embodiment herein, the carbon monoxide hydrogenation catalyst may have a Co loading from about 30 wt % to about 56 wt % based on the total weight of the particulate Fischer-Tropsch catalyst, including any subrange therein. For example, the particulate Fischer-Tropsch catalyst may have a Co loading of about 30 wt %, about 32 wt %, about 34 wt %, about 36 wt %, about 38 wt %, about 40 wt %, about 42 wt %, about 44 wt %, about 46 wt %, about 48 wt %, about 50 wt %, about 52 wt %, about 54 wt %, about 56 wt %, or any range including and between any two of these values.

Illustrative Tubular Reactors of the Present Technology and Related Methods

Referring now to several of the figures, the figures herein are provided to more fully illustrate the preferred aspects of the present technology. The figures should in no way be construed as limiting the scope of the present technology. The examples may include or incorporate any of the variations, embodiments, or aspects of the present technology described in the present disclosure. Furthermore, any embodiment of the process as previously described or further herein described may include or incorporate any one or more elements described in relation to the figures.

Figure 2:
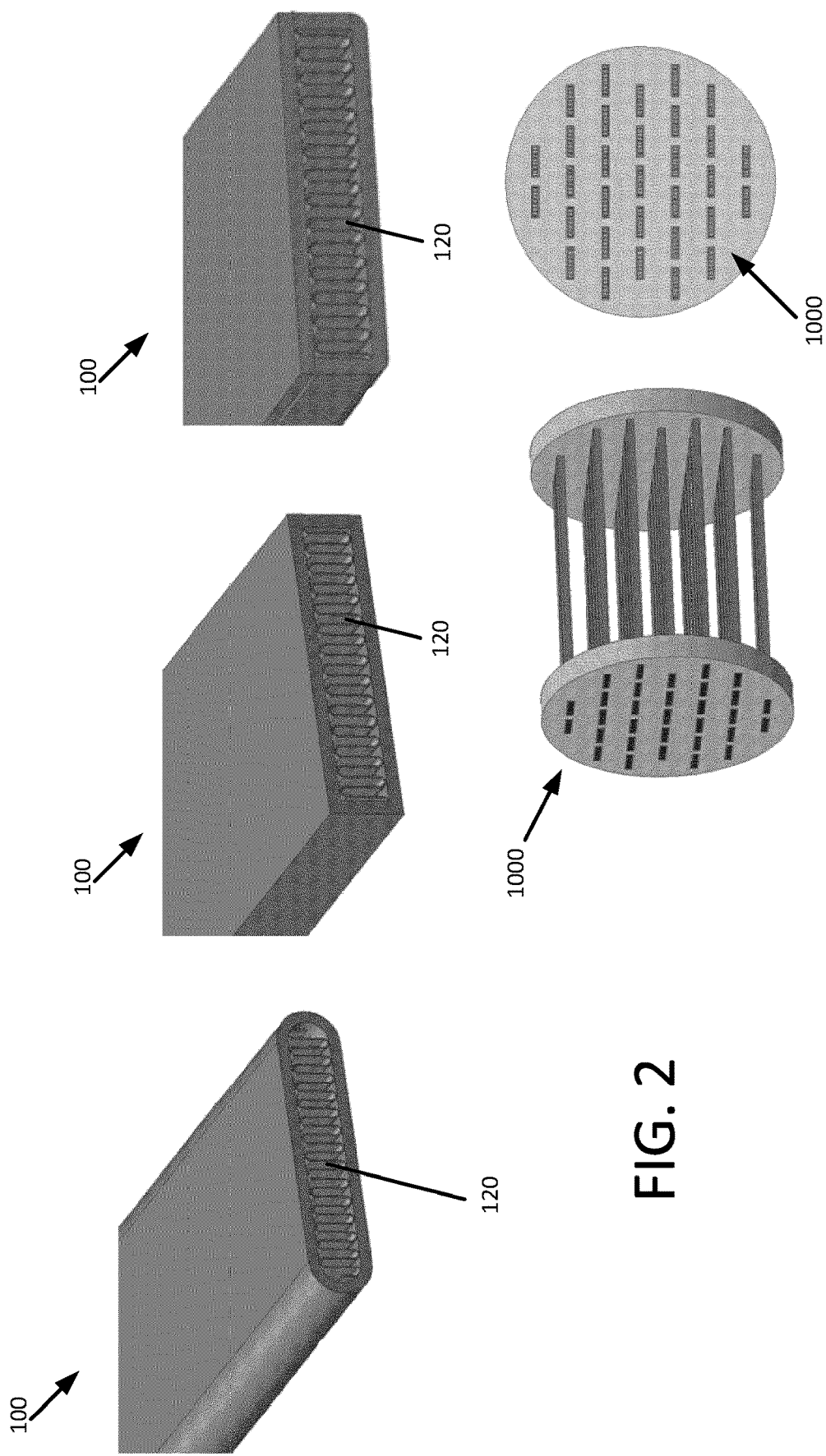
FIG. 2 illustrates another example of a tubular reactor including a plurality of reactor tubes. In the example of FIG. 2, the reactor tubes are rectangular and a heat transfer structure is provided in the form of a waveform.
Figure 4:
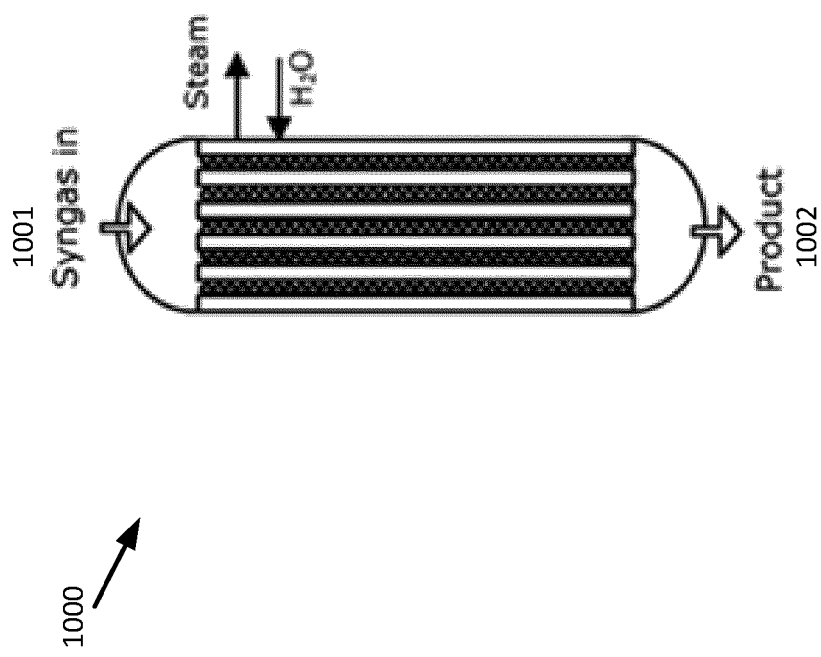
FIG. 4 illustrates a schematic drawing of a conventional fixed bed tubular reactor.
Figure 5:
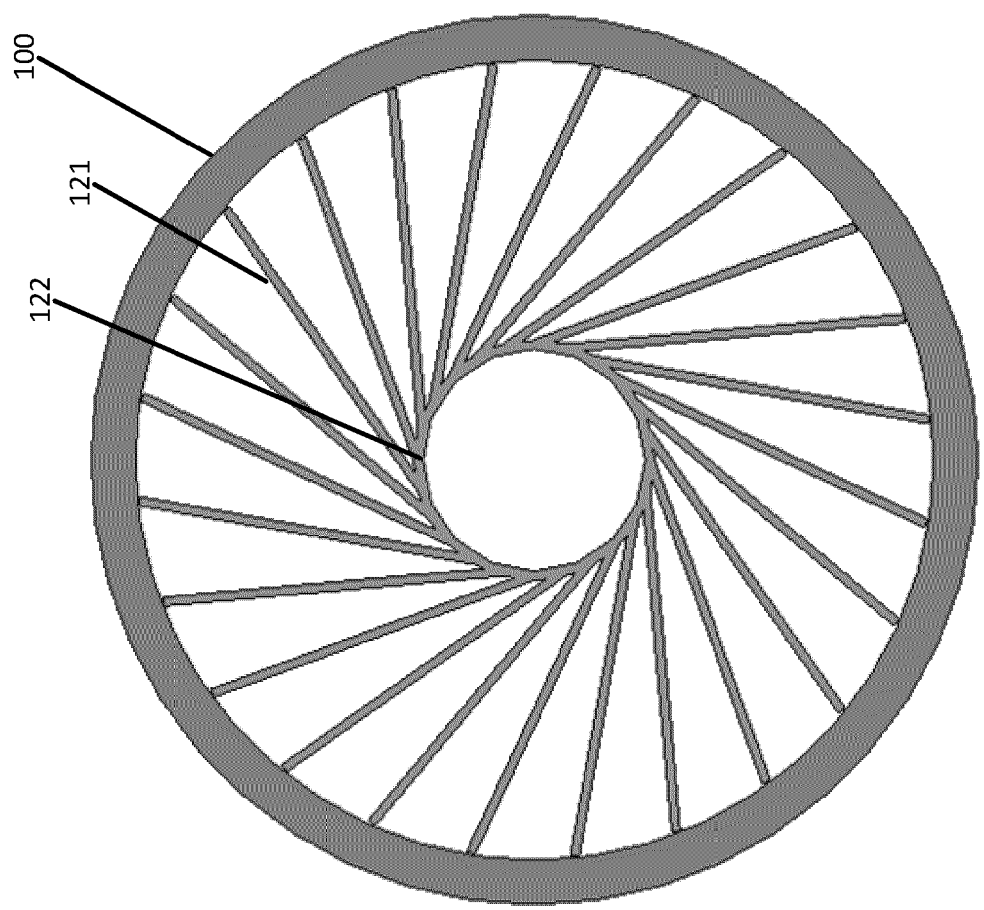
FIG. 5 illustrates an example of a heat transfer structure in which the fins are non-orthogonal to the central support.
Figure 6:
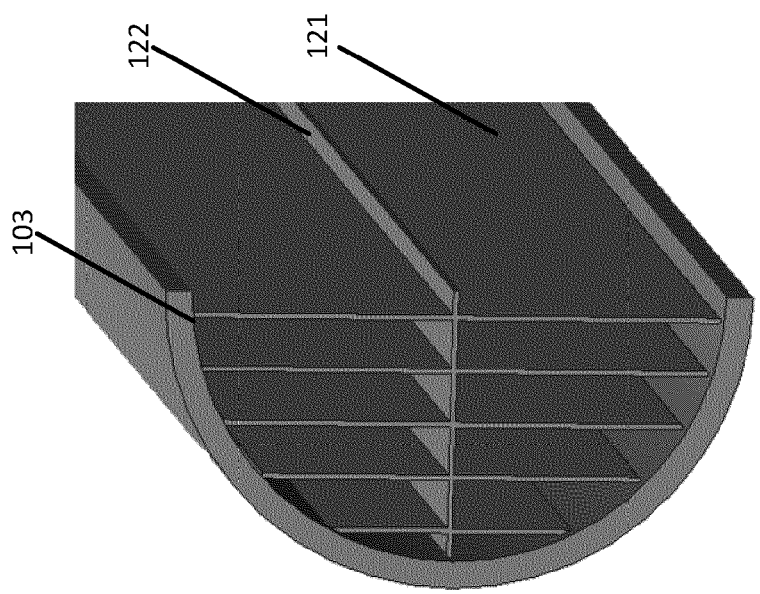
FIG. 6 illustrates an example of a heat transfer structure in which the fins are orthogonal to the central support.

FIG. 4 illustrates a tubular reactor 1000 including a reactor inlet 1001 and a reactor outlet 1002 located downstream of the reactor inlet 1001. Referring to FIGS. 1 and 2, one or more reactor tubes 100 is provided within the tubular reactor 1000. The tubular reactor 1000 may contain from 1 to about 30,000 reactor tubes 100. It may be the tubular reactor 1000 includes at least 100 reactor tubes 100. The tubular reactor 1000 may preferably include less than about 20,000 reactor tubes 100. The tubular reactor 1000 may preferably include less than about 10,000 reactor tubes 100, more preferably less than about 5,000 reactor tubes 100, and even more preferably less than about 2,000 reactor tubes 100. The reactor tubes 100 are arranged parallel with respect to one another.

Each reactor tube 100 is in fluid communication with the reactor inlet 1001 and the reactor outlet 1002. Each reactor tube 100 includes a tube inlet 101, a tube outlet 102 located downstream of the tube inlet 101, an inner tube wall 103 that defines an interior of the reactor tube 100, and an outer tube wall 104 that defines an exterior of the reactor tube 100. A cooling medium may be in contact with the reactor tubes 100 via a channel within the inner tube wall 103 and/or in contact with the outer tube wall 104. A temperature of the cooling medium may be about 160° C. to about 265° C.

Each reactor tube 100 may be made from metal such as low alloy steel, including materials such as chromium-molybdenum heat-resistance steels, or, alternatively, stainless steel or carbon steel. An example of a chromium-molybdenum heat-resistance steel that may be used may contain 0.5 to 9% Cr, 0.5 to 1.0% Mo, and less than or equal to 0.2% C.

In one example, the reactor tube 100 may be cylindrical having a circular cross-section. In other examples, the reactor tube 100 may have a cross-section of any other shape such as a rectangle (see FIG. 2), a square, or an obround. In some examples the reactor tube 100 has a constant cross-section along an entire length thereof. In other examples, the reactor tube 100 includes at least one tapered portion. For instance, as seen in FIG. 1, the tube inlet 101 and the tube outlet 102 may have a same predetermined diameter, and at least a portion of the reactor tube 100 provided between the tube inlet and the tube outlet may have a diameter smaller than or larger than the predetermined diameter of the tube inlet 101 and the tube outlet 102.

As discussed previously, each reactor tube 100 may independently be from about 0.3 meter (m) to about 5 m in length; thus, each reactor tube may independently be about 0.3 m, about 0.4 m, about 0.5 m, about 0.6 m, about 0.7 m, about 0.8 m, about 0.9 m, about 1 m, about 1.5 m, about 2 m, about 2.5 m, about 3 m, about 3.5 m, about 4 m, about 4.5 m, about 5 m, or any range including and/or in between any two of these values. Each reactor tube 100 may independently be shorter than about 5 m. A diameter of the inner tube wall 103 of the one or more reactor tubes 100 may independently be about 20 mm to about 120 mm. Thus, the one or more reactor tubes may each independently have an inner tube wall diameter of about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 110 mm, about 120 mm, or any range including and/or in between any two of these values (e.g., about 20 mm to 80 mm or about 30 to 120 mm).

An interior of at least one reactor tube 100 includes at least one of a catalyst 110 and a heat transfer structure 120. In some examples, all of the reactor tubes 100 include both the catalyst 110 and the heat transfer structure 120. In other examples, some of the reactor tubes 100 include both the catalyst 110 and the heat transfer structure 120, while other reactor tubes 100 do not include either the catalyst 110 or the heat transfer structure 120. In even further examples, all of the reactor tubes 100 include at least one of the catalyst 110 or the heat transfer structure 120. In additional examples, some of the reactor tubes 100 include at least one of the catalyst 110 or the heat transfer structure 120, while other reactor tubes 100 do not include either the catalyst 110 or the heat transfer structure 120.

Figure 10:
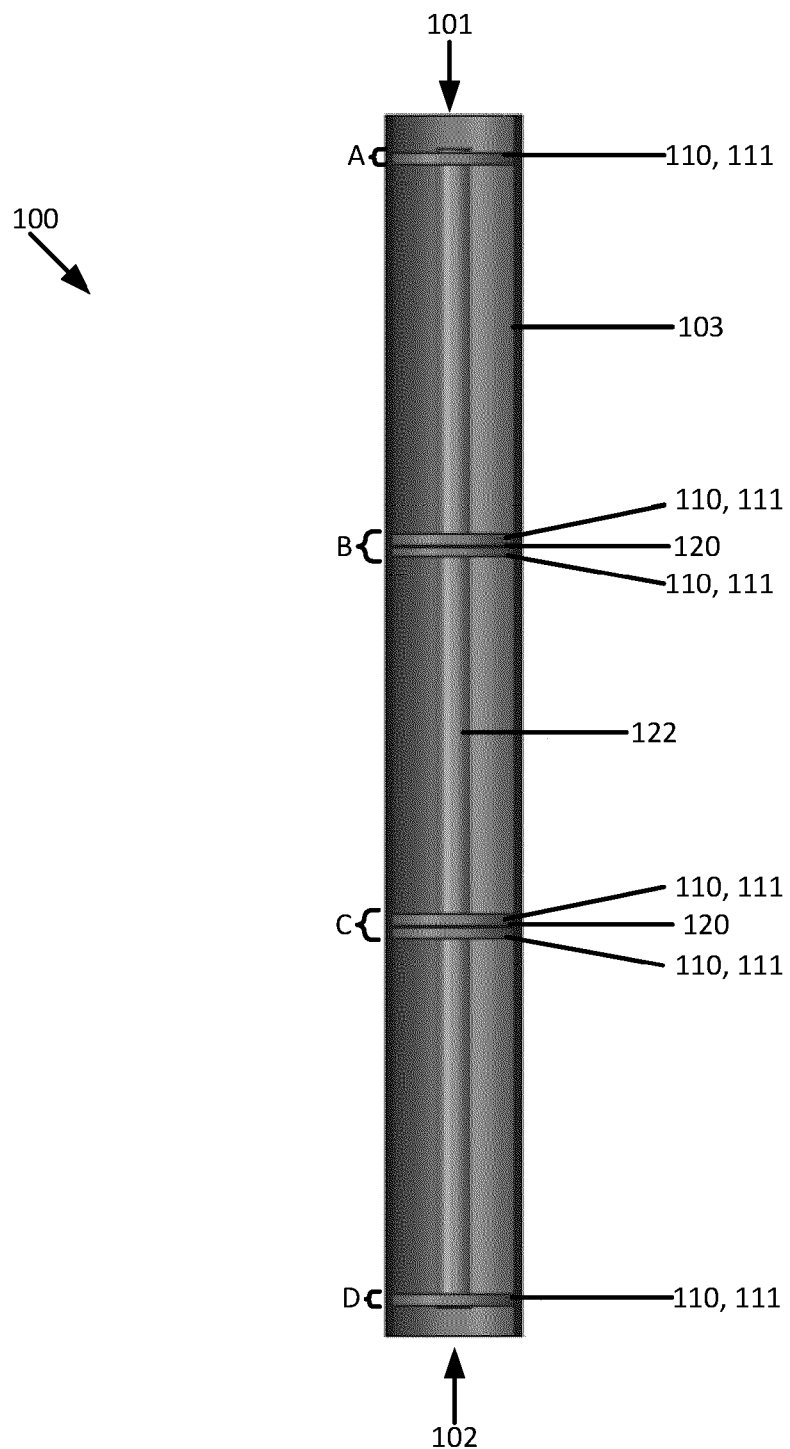
FIG. 10 illustrates a reactor tube in which catalyst is provided in separate reaction zones along a length of the reactor tube. A plurality of heat transfer structures are also provided along a length of the reactor tube.
Figure 11:
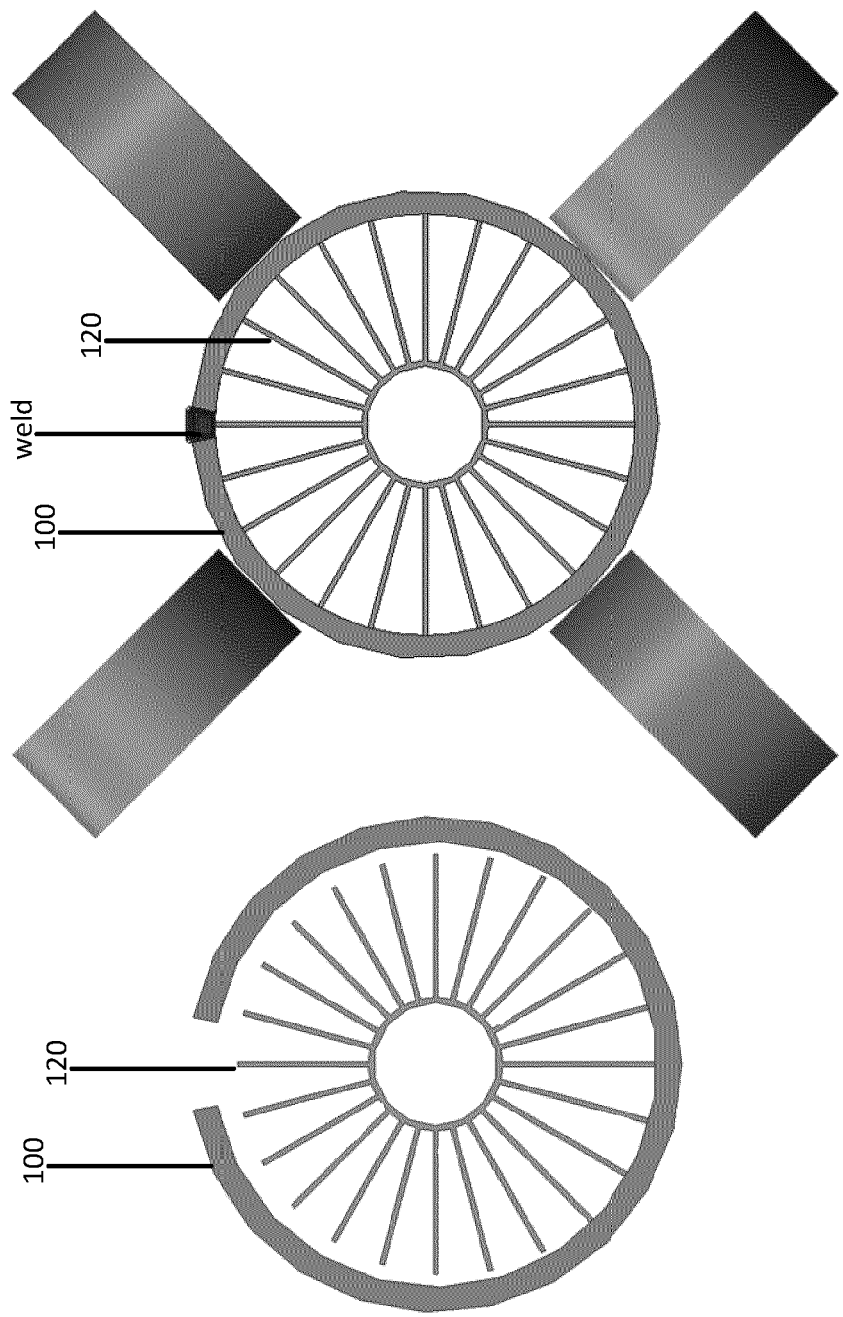
FIG. 11 illustrates an example of a method for disposing the heat transfer structure within a reactor tube.
Figure 12:
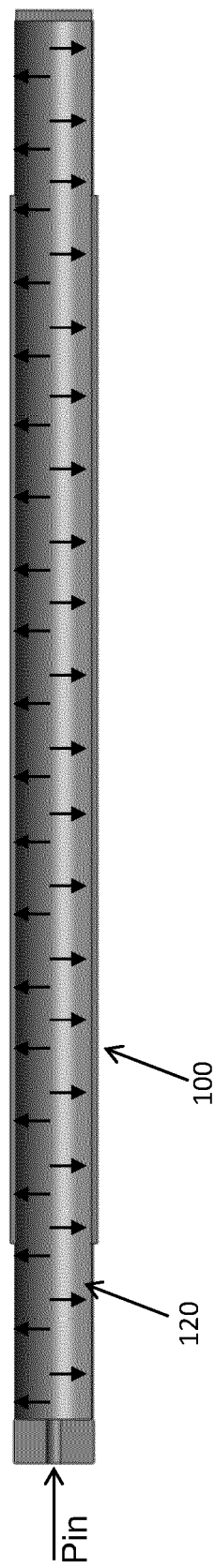
FIG. 12 illustrates another example of a method for disposing the heat transfer structure within a reactor tube.
Figure 13:
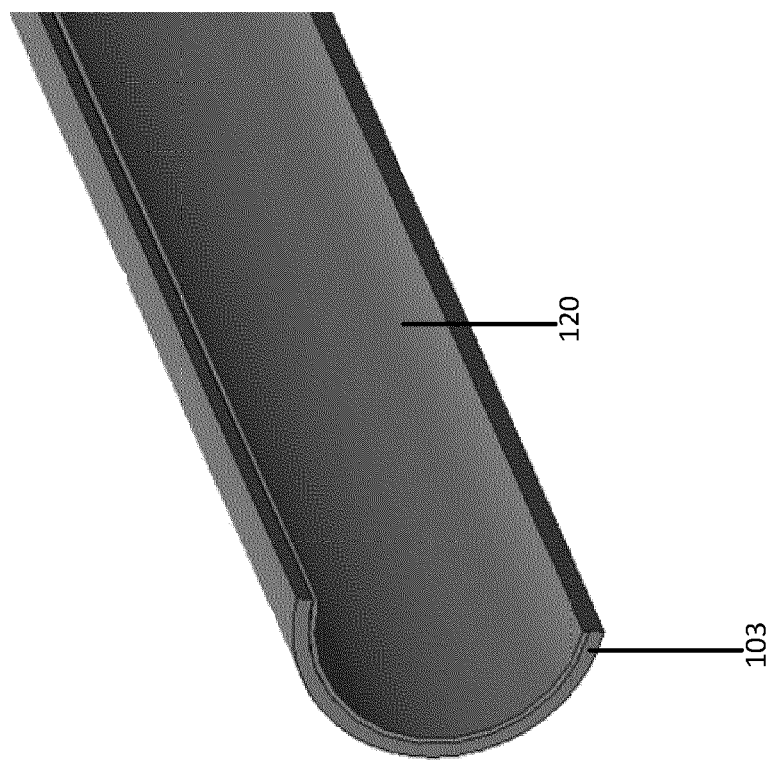
FIG. 13 illustrates another example of a method for disposing the heat transfer structure within a reactor tube.
Figure 14:
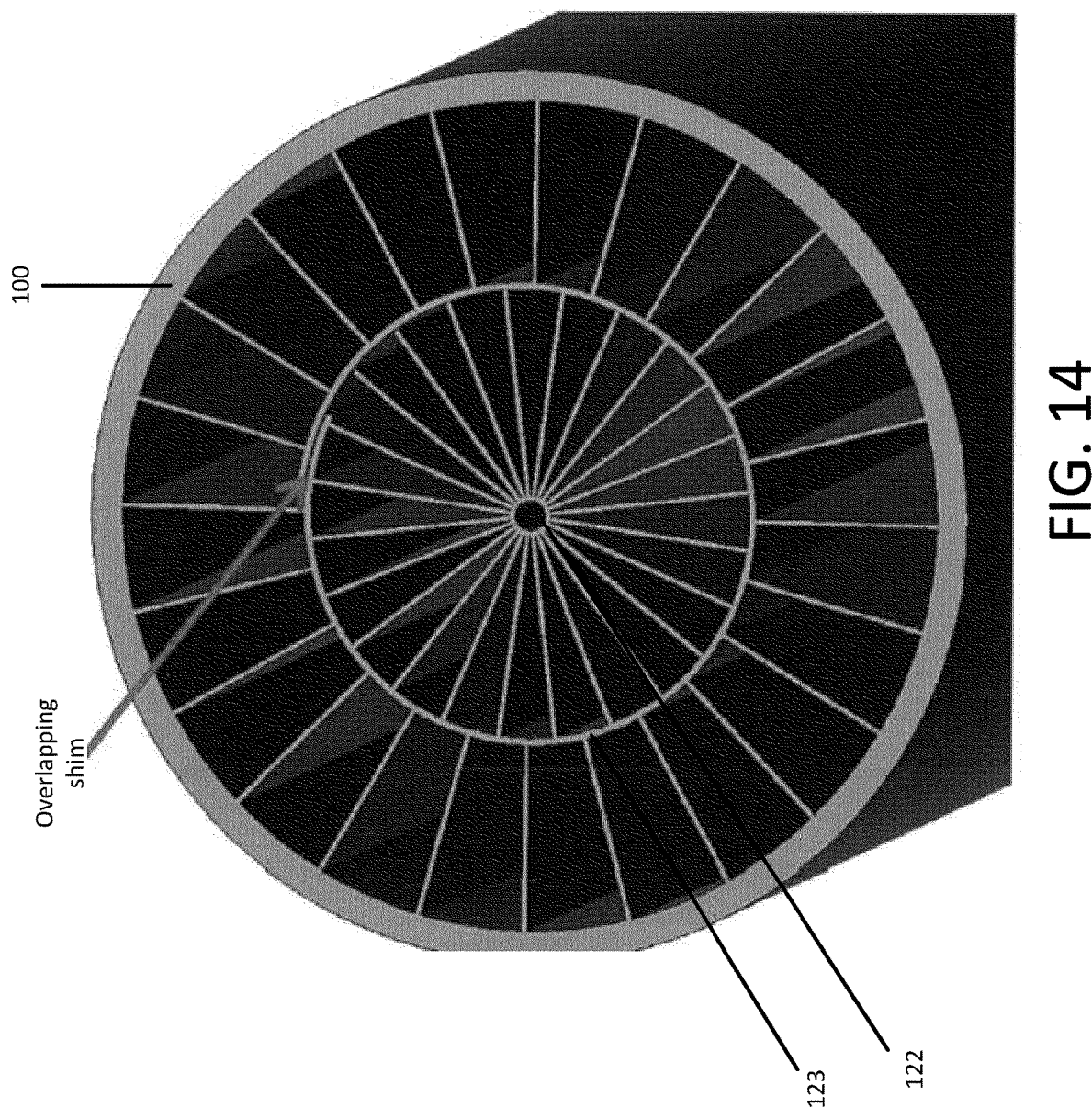
FIG. 14 illustrates another example of a method for disposing the heat transfer structure within a reactor tube.

Referring to FIG. 10, the catalyst 110 may be provided in one section of the reactor tube 100, or in two or more sections of the reactor tube 100, spaced apart to define separate reaction zones A-D along at least a partial length of the reactor tube 100. The catalyst 110 may be any catalyst described in this application or any catalyst suitable for use in a tubular reactor. The same or different catalyst 110 may be used in each reaction zone. For example, each reaction zone may differ from another by activity, weight average diameter, average outer surface to volume ratio, diffusion path, form of catalyst 110 (particulate solid, extrudate), etc., or any combination of any two or more thereof. For example, the catalyst of a first reaction zone group may exhibit a higher activity than the catalyst of a second reaction zone. For example, it may be that the activity of the catalyst of the first reaction zone is at least 5% higher, at least 10% higher, at least 20% higher, at least 30% higher, at least 40% higher, or at least 50% higher than the activity of the catalyst of the second reaction zone. When a third reaction zone is employed, the third reaction zone may contain a catalyst with higher activity than the catalyst in the second reaction zone; it may be that the activity of the catalyst of the third reaction zone is at least 5% higher, at least 10% higher, at least 20% higher, at least 30% higher, at least 40% higher, or at least 50% higher than the activity of the catalyst of the second reaction zone. In any example including two or more reaction zones, each reaction zone may include a heat transfer structure 120. For example, a first heat transfer structure may be in contact with a first volume of catalyst and a second heat transfer structure may be in contact a second volume of catalyst, where the first and second heat transfer structures may be identical or different and/or the catalyst of the first volume is the same or different from the catalyst of the second volume.

The heat transfer structure 120 is in conductive thermal contact with a portion of the catalyst 110 and in at least partial conductive thermal contact with the inner tube wall 103 throughout a surface area of the inner tube wall 103 in at least the one more sections of the reactor tube 100 that contain the catalyst 110. The surface area of the inner tube wall 103 containing the catalyst 110 in conductive thermal contact with the heat transfer structure 120 may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or any range including and/or in between any two of these values. Exemplary embodiments providing a more detailed description of the structure of heat transfer structure 120 will be described below.

The tubular reactor 1000 satisfies at least one of the following conditions: 1) a ratio of an effective thermal conductivity of the heat transfer structure and the catalyst with the inner tube wall to a thermal conductivity of the catalyst ($k_{eff}/k_{cat}$) is at least 50:1, or 2) a total combined surface area of the heat transfer structure and inner tube wall containing the catalyst per volume of the catalyst (the "SA/V") is about 500 $m^2/m^3$ to about 4000 $m^2/m^3$. In some examples, only one of condition 1 or condition 2 is satisfied, while in other examples, both condition 1 and condition 2 are satisfied.

The effective thermal conductivity ratio ($k_{eff}/k_{cat}$) may be at least about 50:1, and may be from about 50:1 to about 2,000:1. The $k_{eff}/k_{cat}$ may be about 50:1, about 100:1, about 200:1, about 300:1, about 400:1, about 500:1, about 600:1, about 700:1, about 800:1, about 900:1, about 1,000:1, about 1,100:1, about 1,200:1, about 1,300:1, about 1,400:1, about 1,500:1, about 1,600:1, about 1,700:1, about 1,800:1, about 1,900:1, about 2,000:1, or any range including and/or in between any two of these values.

The total combined surface area of the heat transfer structure 120 and inner tube wall 103 containing the catalyst 110 per volume of the catalyst 110 (the "SA/V") may be from about 500 $m^2/m^3$ to about 4000 $m^2/m^3$. The SAN may be about 500 $m^2/m^3$, about 550 $m^2/m^3$, about 600 $m^2/m^3$, about 700 $m^2/m^3$, about 800 $m^2/m^3$, about 900 $m^2/m^3$, about 1000 $m^2/m^3$, about 1100 $m^2/m^3$, about 1200 $m^2/m^3$, about 1300 $m^2/m^3$, about 1400 $m^2/m^3$, about 1500 $m^2/m^3$, about 1600 $m^2/m^3$, about 1700 $m^2/m^3$, about 1800 $m^2/m^3$, about 1900 $m^2/m^3$, about 2000 $m^2/m^3$, about 2200 $m^2/m^3$, about 2400 $m^2/m^3$, about 2600 $m^2/m^3$, about 2800 $m^2/m^3$, about 3000 $m^2/m^3$, about 3200 $m^2/m^3$, about 3400 $m^2/m^3$, about 3600 $m^2/m^3$, about 3800 $m^2/m^3$, about 4000 $m^2/m^3$, or any range including and/or in between any two of these values.

Figure 15:
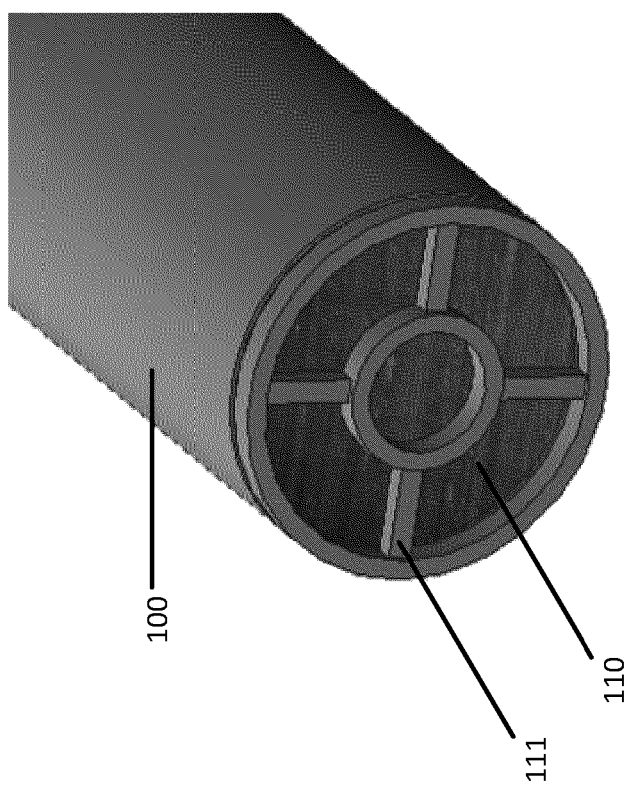
FIG. 15 illustrates an example of a catalyst retention mesh provided at an inlet of the reactor tube.
Figure 28:
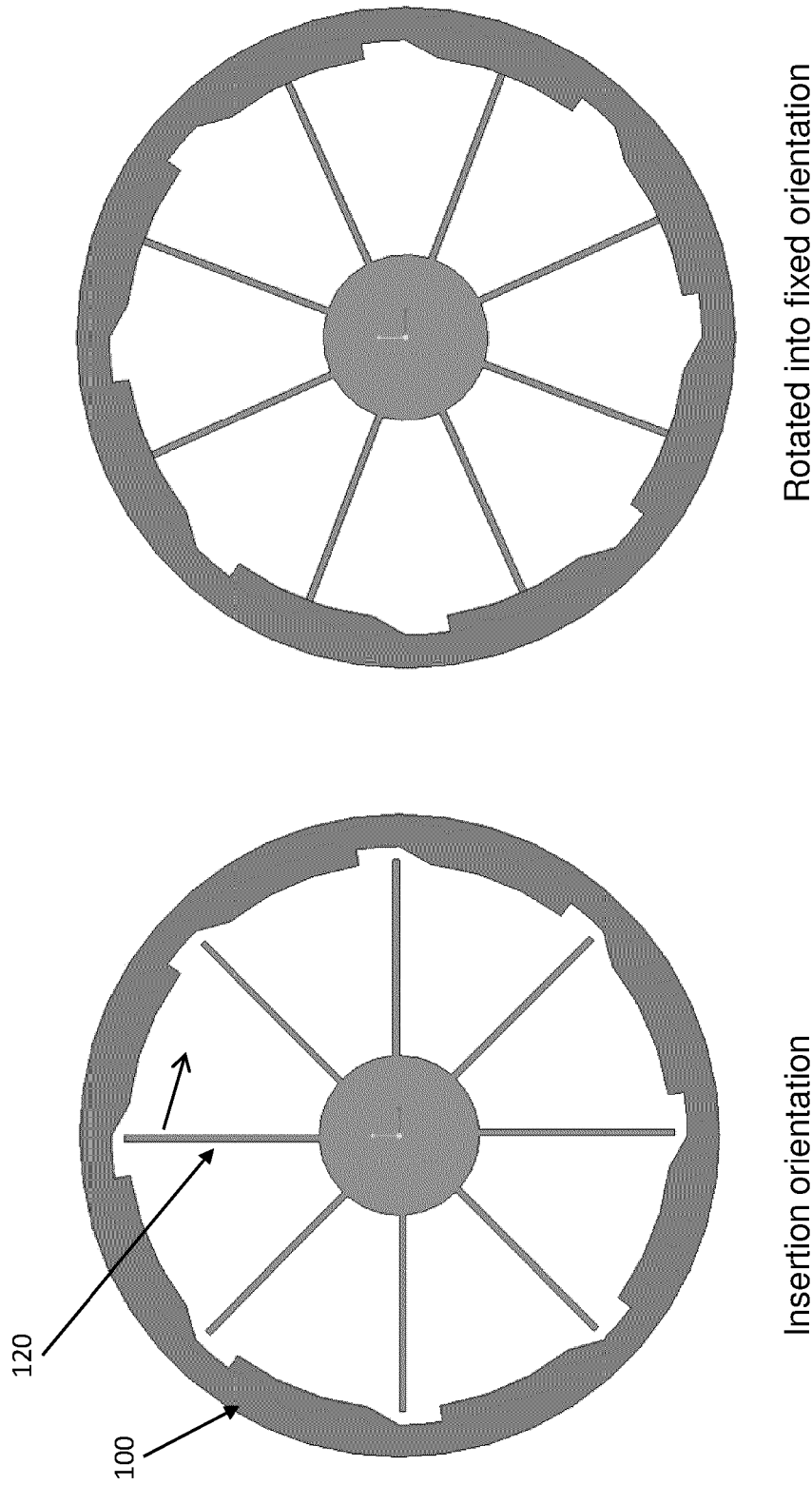
FIG. 28 illustrates an example of a heat transfer structure that is inserted within a reactor tube, rotated, and locked due to a plurality of internal features such as stops, grooves or projections, that limit the rotation of the heat transfer structure.

Referring to FIG. 10, in one example, the reactor tube 100 includes a plurality of heat transfer structures 120 spaced apart from an adjacent heat transfer structure 120 and provided along at least a partial length of the reactor tube 100. The catalyst 110 may be confined within at least one of the plurality of heat transfer structures 120, or provided at an inlet of at least one heat transfer structure 120, for example, within a retainer 111. In examples in which the catalyst 110 is provided within the retainer 111 at the inlet of at least one heat transfer structure 120, the catalyst 110 may also optionally be provided within an additional retainer 111 at an outlet of the heat transfer structure 120. The retainer 111 may be, for example, a wire retention mesh within a retention ring as illustrated in FIGS. 15 and 28, or a flexible mesh wrapped around at least a portion of the heat transfer structure 120 as illustrated in FIG. 9. A size of the voids in the mesh of the retainer 111 is selected such that the catalyst 110 is retained in the voids (i.e., vacant volume) of the retainer 111. In the example of FIG. 9, the flexible mesh may be wrapped around a packed bed including a combination of the catalyst 110 and the heat transfer structure 120.

The heat transfer structure 120 is made of a conductive material, for example, steel, aluminum, copper, an alloy thereof, or a combination of any two or more thereof. For example, the heat transfer structure may include a combination of steel and aluminum, steel and copper, aluminum and copper, or steel, aluminum, and copper.

In some examples, the heat transfer structure 120 includes a single heat conducting surface. In one implementation, as illustrated, for example, in FIG. 13, the heat transfer structure 120 is a coating or cladding disposed on a surface area of the inner tube wall 103, for example, via brazing, physical vapor deposition (PVD), roll bonding, explosive welding, laser cladding, etc. In yet another implementation, the heat transfer structure 120 is an insert provided within the reactor tube 100, where the insert has substantially a same shape as the reactor tube 100 and is concentric with the reactor tube 100.

In other examples, the heat transfer structure 120 is configured to divide the interior of the reactor tube 100 into a plurality of microchannels. See FIGS. 2-6. For example, the heat transfer structure may include an ordered network of heat conducting surfaces, or a random network of heat conducting surfaces. The heat conducting surfaces may be provided in the form of a waveform (see FIG. 2) or a plurality of fins (see FIGS. 3-6) or branches extending from a central support. When provided as a waveform, the heat transfer structure 120 may be a sheet of conductive material bent into an undulating or wave-like pattern and inserted into the reactor tube 100.

In one implementation, the heat transfer structure 120 includes a plurality of fins 121 extending from a central support 122. The central support 122 may be, for example, a metal rod that is concentric with the reactor tube 100 and extends along a length of the reactor tube 100. The central support 122 may include a slight taper at an end thereof to facilitate insertion. The plurality of fins 121 may be evenly spaced from one another, or a distance between a first fin and a second fin may be different from a distance between a third fin and a fourth fin. The plurality of fins 121 may extend from the central support 122 at a 90-degree angle (i.e., orthogonal) with respect to the central support 122 (see FIGS. 3 and 6), or the plurality of fins 121 may extend from the central support 122 at an acute or obtuse angle (i.e., non-orthogonal) with respect to the central support 122 (see FIG. 5). In some examples, the plurality of fins 121 extend from the central support 122 to the inner tube wall 103.

Figure 3:
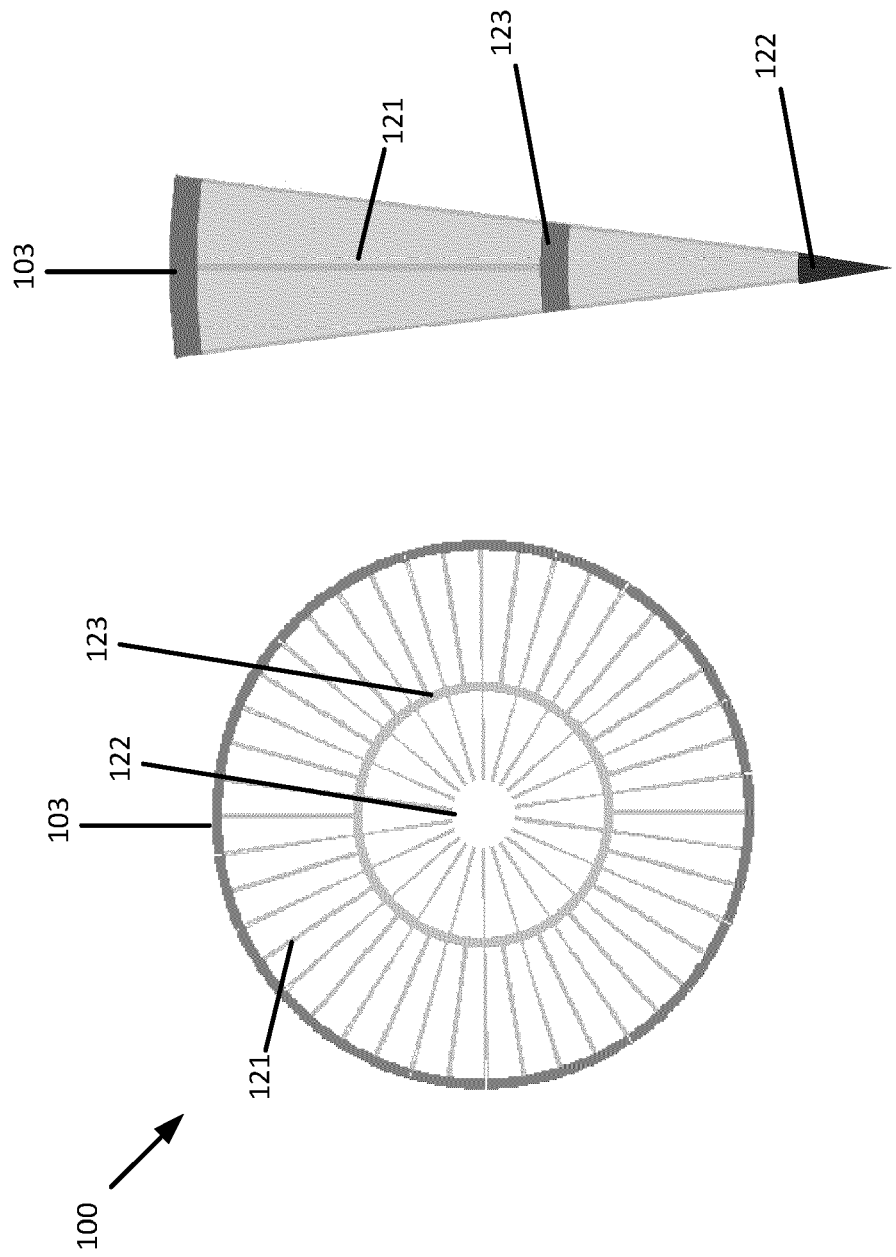
FIG. 3 illustrates an example of a heat transfer structure including a first set of fins formed into a first ring and a second set of fins formed into a second ring. The first ring and the second ring are concentric. A central support is provided in a central opening of the first ring. An inner circumferential wall separates the first ring and the second ring. The first set of fins extend from the central support to the inner circumferential wall. The second set of fins extend from the inner circumferential wall to the inner wall of the reactor tube.

In other examples, the plurality of fins 121 extend from the central support 122 to an internal circumferential wall 123 that defines a first set of microchannels. As seen in FIGS. 3 and 4, a first set of a plurality of fins 121 extend radially from the central support 122 to the internal circumferential wall 123 to define a first set of channels, and a second set of a plurality of fins 121 extend radially from the internal circumferential 123 wall to the inner tube wall 103. Each fin 121 of the second set is in at least partial conductive thermal contact with the inner tube wall 103 to define a second set of channels. The first and second set of fins 121 are concentric. The heat transfer structure 120 may include any number of sets of fins 121, for example, three sets of fins 121, four sets of fins 121 (see FIGS. 25A and 25B), five sets of fins 121, ten sets of fins 121, etc. In such arrangements, the first set of fins 121 extends radially from the central support 122, the last set of fins 121 is at least partially in conductive thermal contact with the inner tube wall 103, and the sets of fins 121 provided between the first set of fins 121 and the last set of fins 121 are separated by an internal circumferential wall. The heat transfer structure 120 is joined, fastened or in compressive force against the inner tube wall 103 to ensure conductive thermal contact.

Figure 7:
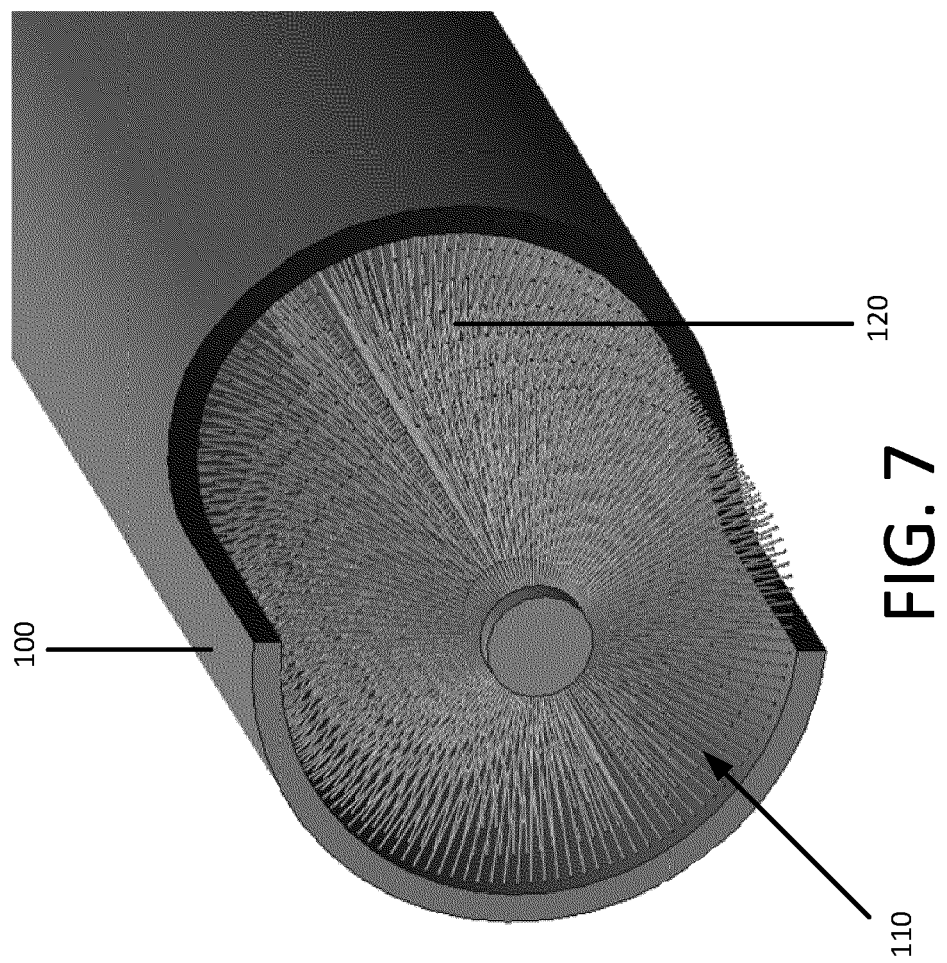
FIG. 7 illustrates an example of a heat transfer structure in the form of a brush including a plurality of bristles.
Figure 8:
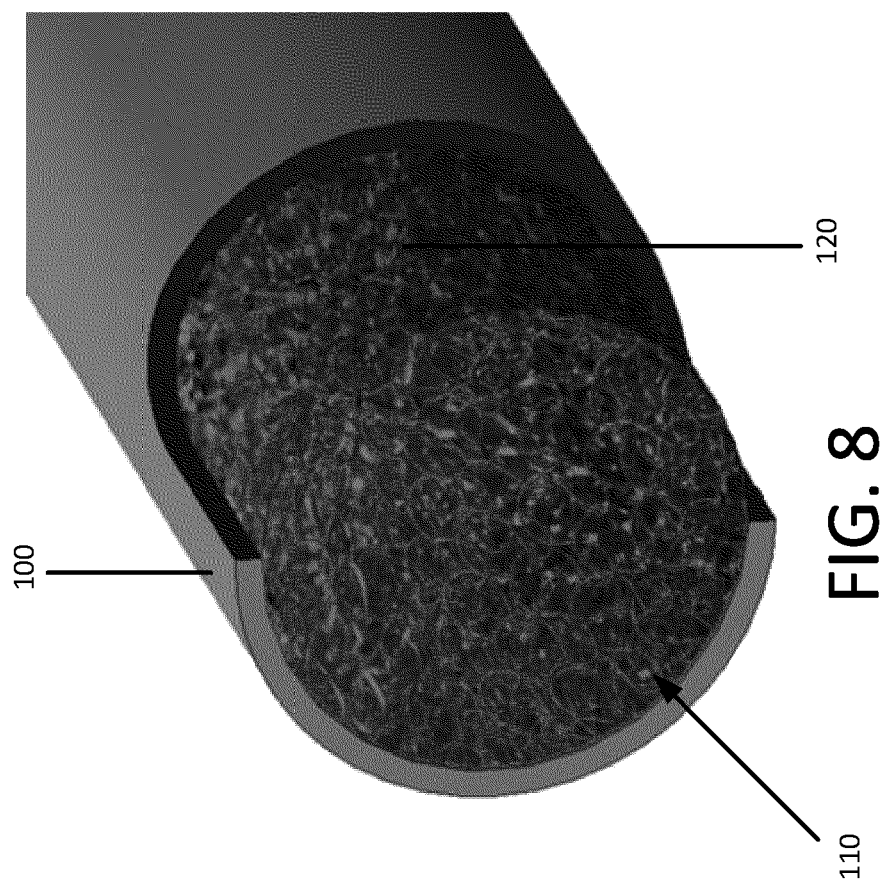
FIG. 8 illustrates an example of a heat transfer structure formed of an unstructured 3D mesh.

In additional examples, as illustrated, for example, in FIG. 16, the heat transfer structure 120 is an insert having a heat conducting surface 124 formed into a spiral conducting surface. A plurality of fins 121 extend from the heat conducting surface 124. Tightly winding the spiral creates contact between fins 121 and the heat conducting surface 124 at the ends of the fins 121 that are not connected to the heat conducting surface 124.

Where the heat transfer structure 120 may be a disordered/random 3D mesh (e.g., a Brillo pad-type structure or the like) as illustrated in FIG. 8, or a brush insert including a plurality of bristles as illustrated in FIG. 7, the catalyst 110 is present in the voids (i.e., vacant volume) of the heat transfer structure 120 in FIGS. 7 & 8. A catalyst retainer structure, and optionally the inner tube wall, contain the material in the catalyst/heat transfer structure volume.

A method of manufacturing the tubular reactor 1000 will now be described. In general, the method includes the steps of providing one or more reactor tubes 100 in fluid communication with a reactor inlet 1001 and a reactor outlet 1002, disposing a volume of a catalyst 110 within the interior of the one or more reactor tubes 100, and disposing a heat transfer structure 120 within the interior of the one or more reactor tubes 100. In some examples, the heat transfer structure 120 is inserted within the interior of the one or more reactor tubes 100 before the catalyst 110 is inserted. In other examples, the heat transfer structure 120 and the catalyst 110 are prepared as a unit outside of the one or more reactor tubes 100, and then simultaneously inserted within the one or more reactor tubes 100 as a unit. After the catalyst 110 and the heat transfer structure 120 are inserted within the one or more reactor tubes 100, the heat transfer structure 120 is in conductive thermal contact with a portion of the catalyst 110 and in at least partial conductive thermal contact with the inner tube wall 103 throughout a surface area of the inner tube wall 103 in the sections containing the catalyst 110. After the catalyst 110 and the heat transfer structure 120 are inserted within the one or more reactor tubes 100, the tubular reactor 1000 satisfies at least one of the following conditions: 1) a ratio of an effective thermal conductivity of the heat transfer structure 120 and the catalyst 110 with the inner tube wall 103 to a thermal conductivity of the catalyst 110 ($k_{eff}/k_{cat}$) is at least 50:1, or 2) a total combined surface area of the heat transfer structure and inner tube wall containing the catalyst per volume of the catalyst (the "SA/V") is about 500 $m^2/m^3$ to about 4000 $m^2/m^3$.

One method of disposing the heat transfer structure 120 within the interior of the one or more reactor tubes 100 includes forming the reactor tube 100 around the heat structure 120. In particular, referring to FIG. 11, the heat transfer structure 120 is provided within a discontinuous perimeter of the reactor tube 100. The perimeter of the reactor tube 100 is discontinuous in that the reactor tube 100 includes an opening extending along a length thereof. The reactor tube 100 is compressed to close the opening and form a seam along the length thereof. The seam is then welded or otherwise connected/sealed such that the heat transfer structure 120 is in at least partial conductive thermal contact with the inner tube wall 103 throughout the surface area of the inner tube wall 103 in sections containing the catalyst.

Figure 29:
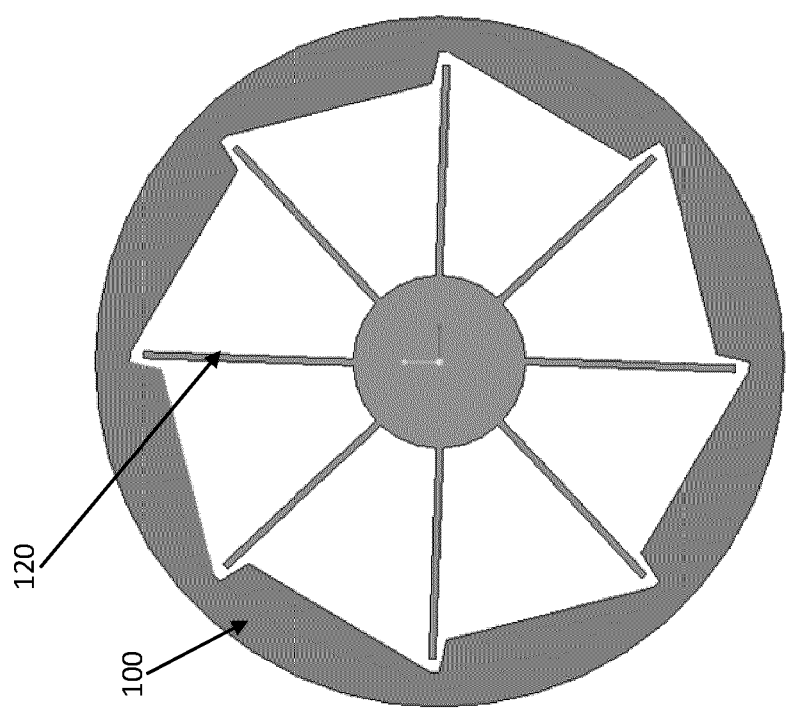
FIG. 29 illustrates another example of a heat transfer structure that is inserted within a reactor tube, rotated, and locked due to a plurality of internal features such as stops, grooves or projections, that limit the rotation of the heat transfer structure.

Referring to FIGS. 28 and 29, another method of disposing the heat transfer structure 120 within the interior of the one or more reactor tubes 100 includes inserting the heat transfer structure 120 within the reactor tube 100, and rotating the heat transfer structure 120 to lock the heat transfer structure 120 in place. The inner tube wall 103 of the reactor tubes 100 may include a plurality of internal features, such as stops, grooves or projections, that limit the rotation of the heat transfer structure 120. Alternatively, the inner tube wall 103 may be a standard reactor tube wall, and a separate locking surface having a plurality of internal features, such as stops, grooves or projections, that limit the rotation of the heat transfer structure 120 may be supplied as part of an insert kit.

Another method of disposing the heat transfer structure 120 within the interior of the one or more reactor tubes 100 includes forming a plurality of fins 121 in a shape of a ring having a central space therein, inserting the ring within the reactor tube 100, and subsequently inserting a central support 122 with the central space of the ring. Insertion of the central support 122 causes the first set of fins 121 to be pushed against the reactor inner tube wall 103. In other words, the ring expands and the central support 122 holds all of the fins 121 in place under compression between the central support 122 and the inner tube wall 103, thereby ensuring conductive thermal contact between the fins 121 and the inner tube wall 103.

Another method of disposing the heat transfer structure 120 within the interior of the one or more reactor tubes 100 relates to the insertion of concentric rings or sets of fins 121. In this method, a plurality of fins 121 are provided in a shape of a ring having a central space therein to define an inner ring of fins 121, and a plurality of fins 121 are provided in a shape of a ring having a central space therein to define a outer ring of fins 121. The outer ring of fins 121 is inserted into the reactor tube 100 before the inner ring of fins 121. The outer ring of fins 121 may be inserted via any of the methods discussed above. One end of each fin in the inner ring of fins 121 contacts or is connected to a sheet of material, where the sheet of material is configured to form an internal circumferential wall between the first and second set of fins 121 when the first set of fins 121 is inserted into the reactor tube 100. The first set of fins 121 is inserted into the reactor tube 100 within the central space of the outer ring of fins 121. The internal circumferential wall includes a shim having a first end in contact with at least one fin in the first set of fins 121, and a second end overlapping the first end along a perimeter of the internal circumferential wall. See FIG. 14. Upon insertion of the inner ring of fins 121 (i.e., the internal circumferential wall and the first set of fins 121) into the central opening of the outer ring of fins 121, the internal circumferential wall expands, and the internal circumferential wall is held in place by friction fit between the first and second set of the plurality of fins 121. Upon expansion of the internal circumferential wall, the first end and the second end of the shim may no longer be overlapping or may be overlapping to a lesser degree than a degree of overlap prior to insertion of the inner ring of fins 121. A central support 122 may optionally be inserted within the central space of the inner ring.

In some of the examples described above, the heat transfer structure 120 is an insert concentric with the reactor tube 100. The insert is formed of a conductive material, for example, a metal such as steel, aluminum, copper, an alloy thereof, or a combination of any two or more thereof. In these examples, one method of disposing the heat transfer structure 120 within the interior of the one or more reactor tubes 100 includes inserting an insert having substantially a same shape as the reactor tube 100 such that the heat transfer structure 120 is held in place via friction fit.

In another example, the reactor tube 100 has an internal diameter, and the heat transfer structure 120 is an insert having an external diameter smaller than the internal diameter of the reactor tube 100. The insert is formed of a conductive material, for example, a metal such as steel, aluminum, copper, an alloy thereof, or a combination of any two or more thereof. In this example, one method of disposing the heat transfer structure 120 within the interior of the one or more reactor tubes 100 (see FIG. 12) includes inserting the insert within the reactor tube 100, sealing one end of the reactor tube inlet or the reactor tube outlet, and applying a predetermined pressure to an unsealed end of the reactor tube 100 to expand the insert such that the insert is in at least partial conductive thermal contact with the inner tube wall 103 of the reactor tube. The insert may be inserted within the reactor tube 100 in an at least partially collapsed state, and expanded to a shape corresponding to a shape of the reactor tube due to the applied predetermined pressure. For example, the insert may be inserted in a conical, collapsed state, and then expanded to a cylindrical shape corresponding to the shape of the reactor tube.

In any embodiment described above of a method of disposing the heat transfer structure 120 within the interior of the one or more reactor tubes 100, the heat transfer structure 120 and the catalyst 110 are prepared as a unit outside of the one or more reactor tubes 100, and then simultaneously inserted within the one or more reactor tubes 100 as a unit, wherein the unit includes a wax entraining the catalyst 110 within the heat transfer structure. Such wax may include one or more compounds selected from $C_1$ to $C_{100}$ hydrocarbons, $C_1$ to $C_{100}$ oxygenated hydrocarbons, or a combination thereof, or any range including and in between any carbon number between $C_1$ and $C_{100}$, as described more fully infra. After disposing the unit with the one or more reactor tubes, the wax may be removed. One non-limiting example of such wax removal includes the periodic wax removed step described infra.

Another method of disposing the heat transfer structure 120 within the interior of the one or more reactor tubes 100 includes forming disposing a conductive material on a surface of the inner tube wall. See FIG. 13. The layer of conductive material comprises the heat transfer structure 120. The conductive material may be disposed on the surface of the inner tube wall via brazing or physical vapor deposition. The conductive material may be a metal, for example, steel, aluminum, copper, an alloy thereof, or a combination of any two or more thereof. For ease of application, the conductive material may be disposed on the surface of the inner tube wall in a state in which the reactor tube has a discontinuous. perimeter. The perimeter of the reactor tube 100 is discontinuous in that the reactor tube 100 includes an opening extending along a length thereof. After the conductive material is disposed on the surface of the inner tube wall, the reactor tube 100 may be compressed to close the opening and form a seam along the length thereof. The seam is then welded.

In any of the examples described above, the heat transfer structure 120 can be retrofit to one or more reactor tubes of an existing tubular reactor. Alternatively, the reactor tubes of an existing tubular reactor may be removed and replaced with new reactor tubes that contain the catalyst 110 and/or the heat transfer structure 120 described in the examples above. In addition, each of the heat transfer structures within a single reactor tube may be removed independent of the remaining heat transfer structures. Removal of the heat transfer structure is reversible and repeatable.

Catalyst Rejuvenation and Regeneration

In any aspect or embodiment involving a Fischer-Tropsch catalyst, the processes may include a periodic catalyst rejuvenation step. In the periodic catalyst regeneration step, the contacting step is discontinued for the duration of the catalyst rejuvenation step. "Periodic" as used herein will be understood to mean occurring after the activity of the Fischer-Tropsch catalyst has decreased and/or there is a particular increase in temperature of the contacting step to maintain about a constant percent conversion of CO by the Fischer-Tropsch catalyst. The particular increase in temperature may be about 5° C. as compared to a temperature previously employed for the same percent conversion of CO. The particular increase in temperature may be about 5° C., or about 10° C., or about 15° C., or about 20° C., or an increase in temperature greater than any one of these values. The rejuvenation step involves flowing a rejuvenation gas including $H_2$ over the Fischer-Tropsch catalyst, and may involve a temperature of about 200° C. to about 400° C., or any range including and in between any two integers between these two values, preferably about 350° C. Such a rejuvenation step strips off a portion of poisons that may become associated with the Fischer-Tropsch catalyst (e.g., NH$_3$) during the contacting step.

The process may include a periodic wax removal step to remove accumulated hydrocarbons from the surfaces of catalyst and the annular spaces in the reactor in order to maintain pressure drop at a manageable level, and may also be performed prior to a rejuvenation step or a regeneration step as described herein, or prior to shut down the reactor for extended periods, or prior to removal of catalyst carriers. The periodic wax removal step may include flowing a dewaxing fluid, such as hydrogen or nitrogen through the reactor tubes where the reactor tubes are at an initial temperature of about 20° C. to about 170° C. (or any range including and between any two integers thereof). Flowing the dewaxing fluid may include flowing the dewaxing fluid at a gas hourly space velocity of about 1,000 h$^{-1}$ to about 20,000 h$^{-1}$. The GHSV may preferably be up to about 10,000 h$^{-1}$, more preferably about 5,000 h$^{-1}$, and even more preferably about 1,000 h$^{-1}$. The wax removal may be performed at pressures of about 1 barg to about 15 barg (or any range including and between any two integers thereof), preferably from about 5 barg to about 15 barg. Such pressures facilitate recycling of the dewaxing fluid via use of a compressor. The reactor tubes are then heating to a hold temperature of about 250° C. to about 450° C. at a rate of about 1° C. per hour to about 60° C. per hour. The temperature of the reactor tube is then maintained at the hold temperature for about 2 hours to about 72 hours, whereupon the reactor tube is subsequently brought to a final temperature of about 20° C. to about 170° C. at a rate of about 1° C. per hour to about 60° C. per hour. The final temperature used will depend upon whether the reactor will be shut down, whether conversion of synthesis gas will resume, or whether a rejuvenation step or regeneration step will be performed. Upon reaching the final temperature, the flow of dewaxing fluid may be discontinued. Optionally, at this stage, a heated inert gas (such as nitrogen or argon) may be flowed through the reactor tube to further remove hydrocarbons, where the heated inert gas may be flowed at a gas hourly space velocity of about 1,000 h$^{-1}$ to about 20,000 h$^{-1}$. The GHSV may preferably be up to about 10,000 h$^{-1}$, more preferably about 5,000 h$^{-1}$, and even more preferably about 1,000 h$^{-1}$. The temperature of the inert gas may be about 250° C. to about 450° C.

The processes involving Fischer-Tropsch catalysts may include a periodic catalyst regeneration step. A person of skill in the art understands it is sometimes desirable to perform a rejuvenation step rather than a regeneration step, or vice versa, and understands when to perform one versus the other. In the periodic catalyst regeneration step, the contacting step is discontinued for the duration of the catalyst regeneration step. Such synthesis catalyst regeneration is well known in the art and as recommended by catalyst suppliers for the particular Fischer-Tropsch catalyst to be regenerated. In any of the above embodiments, the catalyst regeneration step may involve:

(1) a dewaxing step involving flowing a dewaxing gas including H$_2$ over the Fischer-Tropsch catalyst, (2) an oxidation step involving flowing an oxidation gas over the Fischer-Tropsch catalyst, and (3) a reduction step involving exposing the Fischer-Tropsch catalyst to a reducing gas that includes H$_2$.

The temperature dewaxing step, the oxidation step, and the reduction step may each independently be from about 200° C. to about 400° C., or any range including and in between any two integers between these two values, and preferably is about 350° C. The oxidation gas may include one or more of air and N$_2$-diluted air. The dewaxing step typically involves breaking down product associated with the Fischer-Tropsch catalyst; the oxidation step typically involves combusting residual hydrocarbons and/or oxygenated hydrocarbons and oxidizes the Fischer-Tropsch catalyst; and the reduction step typically involves reducing the oxidized Fischer-Tropsch catalyst back to its active form.

The Synthetic Product Provided by the Present Technology and Optional Further Processing The term "synthetic product" as used herein in regard to the presently disclosed technology includes hydrocarbons, oxygenated hydrocarbons, or combinations thereof. Oxygenated hydrocarbons include, but are not limited to, alkanes, alkenes, and alkynes that are each substituted with one or more of an epoxy, hydroxyl, or a carbonyl group. Exemplary carbonyl-containing groups include, but are not limited to an aldehyde, a ketone, a carboxylic acid, a carboxylic acid anhydride, or an ester. Thus, the synthetic product of the present technology includes one or more compounds selected from $C_1$ to $C_{100}$ hydrocarbons, $C_1$ to $C_{100}$ oxygenated hydrocarbons, or a combination thereof, or any range including and in between any carbon number between $C_1$ and $C_{100}$; for example, the synthetic product may include $C_{10}$-$C_{14}$ hydrocarbons. In any of the embodiments described herein, the synthetic product may predominantly include one or more compounds selected from $C_1$ to $C_{50}$ hydrocarbons, $C_1$ to $C_{50}$ oxygenated hydrocarbons, or combinations thereof. "Predominantly" as used herein means at least about 51 weight percent ("wt %") of the synthetic product. The product may include $C_5$+ hydrocarbons (i.e., hydrocarbons with 5 or more carbon atoms). The synthetic product of the present technology may include one or more compounds selected from $C_1$ to $C_{50}$ hydrocarbons, $C_1$ to $C_{50}$ oxygenated hydrocarbons, or combinations thereof in an amount of about 51 wt % to about 100 wt %, or any range including and in between any integer between these two values. Thus, the synthetic product may include 40 wt % of $C_{14}$-$C_{18}$ hydrocarbons; the synthetic product may include 70 wt % of $C_1$-$C_4$ monohydroxyalkanes (i.e., monohydric alcohols).

Hydrocarbons of the synthetic product of any aspect and embodiment described herein may further be reacted to provide a desired product.

For example, the hydrocarbons may be directed to a hydrocracking reaction. Hydrocracking catalysts suitable for such reactions may include zeolite catalysts. Zeolite catalysts include, but are not limited to, beta zeolite, omega zeolite, L-zeolite, ZSM-5 zeolites and Y-type zeolites. The hydrocracking catalyst may also include one or more pillared clays, MCM-41, MCM-48, HMS, or a combination of any two or more thereof. The hydrocracking catalyst may include Pt, Pd, Ni, Co, Mo, W, or a combination of any two or more thereof. The hydrocracking catalyst may further include a refractory inorganic oxide such as alumina, magnesia, silica, titania, zirconia, silica-alumina, or combinations of any two or more thereof. The hydrocracking catalyst may further include a hydrogenation component. Examples of suitable hydrogenation components include, but are not limited to, metals of Group IVB and Group VIII of the Periodic Table and compounds of such metals. For example, molybdenum, tungsten, chromium, iron, cobalt, nickel, platinum, palladium, iridium, osmium, rhodium, ruthenium, or combinations of any two or more thereof may be used as the hydrogenation component. Exemplary catalysts are described in U.S. Pat. No. 6,312,586, which is incorporated herein by reference in its entirety for any and all purposes.

The hydrocarbons may be directed to a hydrotreating, where the hydrotreating involves a hydrotreating catalyst. The hydrotreating catalyst may include Ni, Mo, Co, W, or combinations of any two or more thereof. The hydrotreating catalyst may be a supported catalyst, such as a hydrotreating catalyst supported on alumina. In some embodiments, the catalyst may include Mo—W/$Al_2O_3$.

It may be that the hydrocarbons are directed to a hydrocarbon oxidation involving an oxidation catalyst. The oxidation catalyst may include a metal, metal oxide, or mixed metal oxide of Mo, W, V, Nb, Sb, Sn, Pt, Pd, Cs, Zr, Cr, Mg, Mn, Ni, Co, Ce, or a combination of any two or more thereof. These catalysts may further include one or more alkali metals or alkaline earth metals or other transition metals, rare earth metals or lanthanides. Elements such as P and Bi may be present. The catalyst may be supported and, if so, useful support materials include metal oxides (e.g. alumina, titania, zirconia), silica, mesoporous materials, zeolites, refractory materials, or combinations of two or more thereof.

In any of the aspects and embodiments described herein, it may be that the hydrocarbons are directed to a hydrocracking, a hydrotreating, or combination thereof.

Alkylene Oxide Production

In a related aspect, a process is provided for the production of an alkylene oxide. The process includes contacting in a tubular reactor a gaseous stream comprising a $C_2$-$C_4$ alkylene and an oxygen source with an alkylene oxidation catalyst to produce a synthetic product comprising the alkylene oxide. The tubular reactor includes (a) a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the alkylene oxidation catalyst within the reactor tube; (b) a reactor outlet located downstream of the reactor inlet in fluid communication with the one or more reactor tubes; and (c) a cooling medium in contact with the one or more reactor tubes. In the process, the diameter of the inner tube wall is from 20 mm to 120 mm; the heat transfer structure comprises a network of heat conducting surfaces in conductive thermal contact with a portion of the alkylene oxidation catalyst and wherein the heat transfer structure is in at least partial conductive thermal contact throughout the surface area of the inner tube wall containing the alkylene oxidation catalyst. The process further includes at least one of the following:

(1) a ratio of effective thermal conductivity of the heat transfer structure and the alkylene oxidation catalyst with the inner tube wall over thermal conductivity of the alkylene oxidation catalyst ($k_{eff}/k_{cat}$) of at least about 50:1; and (2) a total combined surface area of the heat transfer structure and inner tube wall containing the alkylene oxidation catalyst per volume of the alkylene oxidation catalyst (the "SA/V") from about 500 $m^2/m^3$ to about 4000 $m^2/m^3$.

The network of heat conducting surfaces themselves and/or in combination with the inner tube wall define a plurality of channels within the reactor tube containing the alkylene oxidation catalyst. The channels may be of any cross-sectional shape, such as circular, oval, square, rhomboid, triangular, etc. The largest measurable span of the cross-sectional shape of a channel is taken to be the "channel diameter." The channels each independently have a channel diameter from about 0.01 mm to about 10 mm; thus, each channel may independently have a channel diameter of about 0.01 mm, about 0.02 mm, about 0.04 mm, about 0.06 mm, about 0.08 mm, about 0.1 mm, about 0.2 mm, about 0.4 mm, about 0.6 mm, about 0.8 mm, about 1 mm, about 1.5 mm, about 2 mm, about 2.5 mm, about 3 mm, about 3.5 mm, about 4 mm, about 5 mm, about 6 mm, about 7 mm, about 8 mm, about 9 mm, about 10 mm, or any range including and/or in between any two of these values.

The $k_{eff}/k_{cat}$ may be at least about 50:1, and may be from about 50:1 to about 2,000:1. The $k_{eff}/k_{cat}$ may be about 50:1, about 100:1, about 200:1, about 300:1, about 400:1, about 500:1, about 600:1, about 700:1, about 800:1, about 900:1, about 1,000:1, about 1,100:1, about 1,200:1, about 1,300:1, about 1,400:1, about 1,500:1, about 1,600:1, about 1,700:1, about 1,800:1, about 1,900:1, about 2,000:1, or any range including and/or in between any two of these values.

The gaseous stream in the process may include one or more of the following:
(1) the $C_2$-$C_4$ alkylene to oxygen source mole ratio in the gaseous stream may be from about 0.2:1 to about 4:1;
(2) a diluent concentration in the gaseous stream may be less than about 50% by volume; and
(3) the gaseous stream may include the oxygen source at a concentration of at least about 8% by volume.

The total combined surface area of the heat transfer structure and inner tube wall containing the alkylene oxidation catalyst per volume of the alkylene oxidation catalyst (the "SA/V") may be from about 500 $m^2/m^3$ to about 4000 $m^2/m^3$. The SA/V may be about 500 $m^2/m^3$, about 550 $m^2/m^3$, about 600 $m^2/m^3$, about 700 $m^2/m^3$, about 800 $m^2/m^3$, about 900 $m^2/m^3$, about 1000 $m^2/m^3$, about 1100 $m^2/m^3$, about 1200 $m^2/m^3$, about 1300 $m^2/m^3$, about 1400 $m^2/m^3$, about 1500 $m^2/m^3$, about 1600 $m^2/m^3$, about 1700 $m^2/m^3$, about 1800 $m^2/m^3$, about 1900 $m^2/m^3$, about 2000 $m^2/m^3$, about 2200 $m^2/m^3$, about 2400 $m^2/m^3$, about 2600 $m^2/m^3$, about 2800 $m^2/m^3$, about 3000 $m^2/m^3$, about 3200 $m^2/m^3$, about 3400 $m^2/m^3$, about 3600 $m^2/m^3$, about 3800 $m^2/m^3$, about 4000 $m^2/m^3$, or any range including and/or in between any two of these values.

In any embodiment herein, it may be at least about 5% of the surface area of the inner tube wall containing the alkylene oxidation catalyst is in conductive thermal contact with the heat transfer structure. The surface area of the inner tube wall containing alkylene oxidation catalyst in conductive thermal contact with the heat transfer structure may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or any range including and/or in between any two of these values.

The gaseous stream may include one or more diluents. Diluents include, but are not limited to, molecular nitrogen, helium, methane, natural gas, carbon dioxide, liquid water, steam, argon, and the like, as well as any mixture of any two or more thereof. The diluent may be included from zero (i.e., no diluent is included) to about 75% by volume of the gaseous stream. Thus, the volume of diluent included in the gaseous stream may be none (i.e., 0%), about 0.1%, about 1%, about 5%, about 10%, about 15%, about 20%, about 25%, about 30%, about 35%, about 40%, about 45%, about 50%, about 55%, about 60%, about 65%, about 70%, about 75%, or any range in between and/or including any two of these values. However, an advantage of the present technology is that the process may be performed without the use of such diluents, thus a more efficient and compact process may be provided.

The process of the present technology utilizes an enhanced capacity for heat removal, and as a result there may be little need for diluent gases or excess $C_2$-$C_4$ alkylene to limit temperature excursions. Thus, while unreacted $C_2$-$C_4$ alkylene and/or oxygen source may be separated from the alkylene oxide in the synthetic product using conventional or microchannel techniques and recycled back through the process, the process may be run with a gaseous stream that includes a relative proportion of $C_2$-$C_4$ alkylene and oxygen source that is much closer to stoichiometric. This may shrink the recycle stream significantly, resulting in a savings on power and an increase in capacity. In fact, the conversion may be sufficient to eliminate recycle altogether, which would result in an even greater savings and enhanced economics compared to tubular processes of the prior art.

In any embodiment of the process, the contacting step may include maintaining at least about 1% alkylene conversion per pass in the one or more reactor tubes, where per pass conversion of alkylene is defined by the difference between the inlet and outlet moles of alkylene divided by the inlet number of moles of alkylene. The alkylene per pass conversion may be at least about 1%, at least about 5%, at least about 10%, at least about 15%, at least about 20%, at least about 25%, at least about 30%, at least about 35%, at least about 40%, at least about 45%, at least about 50%, or any range including and/or in between any two of these values. A low per pass yield may create a need for a downstream separation and recycle of ethylene. Because the present technology allows for greater heat transfer, higher per pass yields may be realized thus lowering the cost of any downstream separation and alkylene recycle.

The $C_2$-$C_4$ alkylene may include ethylene, propylene, 1-butene, 2-butene, or mixtures of any two or more thereof. The gaseous stream may include from about 10% to about 75% by volume $C_2$-$C_4$ alkylene. Thus, the volume of $C_2$-$C_4$ alkylene in the gaseous stream may be about 10%, about 15%, about 20%, about 25%, about 30%, about 35%, about 40%, about 45%, about 50%, about 55%, about 60%, about 65%, about 70%, about 75%, or any range in between and/or including any two of these values.

The level of selectivity to the alkylene oxide in the process may be at least about 40%. The term "selectivity to alkylene oxide" refers to the moles of alkylene oxide produced divided by the sum of the moles of alkylene oxide produced and the moles of other products (e.g., CO, $CO_2$) produced where each product in the denominator is multiplied by its respective stoichiometric factor in the reaction. For example, for the oxidation of ethylene to ethylene oxide with carbon dioxide as an unwanted side product, the production of one mole of ethylene oxide and one mole of carbon dioxide would correspond to a selectivity of 67% (i.e., 100×(1/(1+0.5))=67%). The level of selectivity to alkylene oxide (e.g., ethylene, propylene, 1-butene, 2-butene, or mixtures of any two or more thereof) in the process may be at least about 40%, at least about 50%, at least about 60%, at least about 70%, at least about 80%, at least about 90%, at least about 95%, at least about 99%, or any range including and/or in between any two of these values.

The oxygen source may include, but is not limited to, molecular oxygen and/or other oxidants such as nitrogen oxides (e.g., NO, $N_2O$) which may function as sources of oxygen, as well as mixtures of any two or more thereof. For example, oxygen enriched air may be included in the process to provide an oxygen source (in this example, molecular oxygen). The gaseous stream may include the oxygen source in a volume from about 5% to about 50%; the volume of the oxygen source in the gaseous stream may be about 5%, about 10%, about 15%, about 20%, about 25%, about 30%, about 35%, about 40%, about 45%, about 50%, or any range in between and/or including any two of these values.

The $C_2$-$C_4$ alkylene to oxygen source mole ratio in the gaseous stream may be from about 0.2:1 to about 10:1. The mole ratio of $C_2$-$C_4$ alkylene to oxygen source in the gaseous stream may be about 0.2:1, about 0.4:1, about 0.6:1, about 0.8:1, about 1:1, about 1.5:1, about 2:1, about 2.5:1, about 3:1, about 3.5:1, about 4:1, about 4.5:1, about 5:1, about 6:1, about 7:1, about 8:1, about 9:1, about 10:1, or any range in between and/or including any two of these values.

The gaseous stream may include one or more organic halides. Such organic halides include one or more $C_1$-$C_5$ alkyl halides and/or $C_2$-$C_5$ alkenyl halides, for example, ethyl chloride and/or vinyl chloride, and the like. Such organic halides may be used as promoters for the conversion of $C_2$-$C_4$ alkylene and the oxygen source to alkylene oxide. The halides may include chloride, bromide, and/or iodide. The gaseous stream may include about 100 parts per million (ppm) of less by volume of one or more organic halides. The amount of the one or more organic halides in the gaseous stream may be about 0.3 ppm, about 0.5 ppm, about 1 ppm, about 5 ppm, about 10 ppm, about 15 ppm, about 20 ppm, about 25 ppm, about 30 ppm, about 35 ppm, about 40 ppm, about 50 ppm, about 60 ppm, about 70 ppm, about 80 ppm, about 90 ppm, about 100 ppm, or any range in between and/or including any of two of these values.

In general, while the purity of the components of the gaseous stream may not be critical, it is desirable to avoid the presence of compounds which may poison the alkylene oxidation catalyst.

The process described herein may include a catalyst gas hourly space velocity (GHSV) of the gaseous stream in the tubular reactor from about 100 $hr^{-1}$ to about 2,000,000 $hr^{-1}$. It may be that the catalyst gas hourly space velocity is about 500 $hr^{-1}$, about 750 $hr^{-1}$, about 1,000 $hr^{-1}$, about 2,000 $hr^{-1}$, about 3,000 $hr^{-1}$, about 4,000 $hr^{-1}$, about 5,000 $hr^{-1}$, about 6,000 $hr^{-1}$, about 7,000 $hr^{-1}$, about 8,000 $hr^{-1}$, about 9,000 $hr^{-1}$, about 10,000 $hr^{-1}$, about 11,000 $hr^{-1}$, about 12,000 $hr^{-1}$, about 13,000 $hr^{-1}$, about 14,000 $hr^{-1}$, about 15,000 $hr^{-1}$, about 16,000 $hr^{-1}$, about 17,000 $hr^{-1}$, about 18,000 $hr^{-1}$, about 19,000 $hr^{-1}$, about 20,000 $hr^{-1}$, about 25,000 $hr^{-1}$, about 50,000 $hr^{-1}$, about 75,000 $hr^{-1}$, about 100,000 $hr^{-1}$, about 150,000 $hr^{-1}$, about 200,000 $hr^{-1}$, about 250,000 $hr^{-1}$, about 500,000 $hr^{-1}$, about 750,000 $hr^{-1}$, about 1,000,000 $hr^{-1}$, about 1,500,000 $hr^{-1}$, about 2,000,000 $hr^{-1}$, or any range including and between any two of these values.

The temperature of the gaseous stream at the reactor inlet may be about 150° C. to about 1,000° C. Thus, the temperature of the gaseous stream at the reactor inlet may be about 150° C., about 200° C., about 250° C., about 300° C., about 350° C., about 400° C., about 450° C., about 500° C., about 550° C., about 600° C., about 650° C., about 700° C., about 750° C., about 800° C., about 850° C., about 900° C., about 950° C., about 1,000° C., or any range including and/or in between any two of these values.

As described above, the cooling medium is in contact with the one or more reactor tubes. The cooling medium temperature may be from about −70° C. to about 350° C.; the cooling medium temperature may therefore be about −70° C., about −60° C., about −50° C., about −40° C., about −30° C., about −20° C., about −10° C., about 0° C., about 10° C., about 20° C., about 30° C., about 40° C., about 50° C., about 60° C., about 70° C., about 80° C., about 90° C., about 100° C., about 125° C., about 150° C., about 175° C., about 200° C., about 225° C., about 250° C., about 275° C., about 300°

C., about 325° C., about 350° C., or any range including and/or in between any two of these values.

In regard to the reactor tube(s), each reactor tube may independently be from about 0.3 meters (m) to about 5 m in length; thus, each reactor tube may independently be about 0.3 m, about 0.4 m, about 0.5 m, about 0.6 m, about 0.7 m, about 0.8 m, about 0.9 m, about 1 m, about 1.5 m, about 2 m, about 2.5 m, about 3 m, about 3.5 m, about 4 m, about 4.5 m, about 5 m, or any range including and/or in between any two of these values. It may be each reactor tube is independently less than about 5 m. The diameter of the inner tube wall of the one or more reactor tubes is independently in each tube about 20 mm to about 120 mm. Thus, the one or more reactor tubes may each independently have an inner tube wall diameter of about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 110 mm, about 120 mm, or any range including and/or in between any two of these values. In some embodiments the diameter of the inner tube wall of the one or more reactor tubes is about 20 mm to about 80 mm.

The tubular reactor may contain from 1 to about 30,000 reactor tubes. It may be the tubular reactor includes at least 100 reactor tubes. The tubular reactor may preferably include less than about 20,000 reactor tubes. The tubular reactor may preferably include less than about 10,000 reactor tubes, more preferably less than about 5,000 reactor tubes, and even more preferably less than about 2,000 reactor tubes.

Alkylene oxidation catalysts include, but are not limited to, any olefin epoxidation catalyst useful for converting a $C_2$-$C_4$ alkylene and an oxygen source to an alkylene oxide. The alkylene oxidation catalyst may include a metal, metal oxide, or mixed metal oxide. The metal may include Ag, Mo, Re, W, V, Nb, Sb, Sn, Pt, Pd, Cs, Zr, Cr, Mg, Mn, Ni, Co, Ce, an oxide of any one or more of these metals, or a mixture of any two or more thereof. For example, the alkylene oxidation catalyst may include Ag or an oxide thereof. The alkylene oxidation catalyst may include a Ag loading from about 10 wt % to about 50 wt % of the alkylene oxidation catalyst; thus the alkylene oxidation catalyst may include a Ag loading of about 10 wt %, about 15 wt %, about 20 wt %, about 25 wt %, about 30 wt %, about 35 wt %, about 40 wt %, about 45 wt %, about 50 wt %, or any range including and/or in between any two of these values. Alkylene oxidation catalysts may also include one or more alkali metals, alkaline earth metals, transition metals, rare earth metals, lanthanides, or mixtures of any two or more thereof. The alkali metal may include lithium, cesium, or a mixture thereof. Additionally P, S, Bi, oxides thereof, or combinations of any two or more thereof may be included. The catalyst may be supported, and if so, useful support materials include metal oxides (e.g., alumina, titania, zirconia), silica, mesoporous materials, zeolites, refractory materials, and combinations of any two or more thereof. The alkylene oxidation catalyst may include sulfur or an oxide thereof. Illustrative alkyene oxidation catalysts are disclosed U.S. Pat. Nos. 8,524,927, 4,908,343; 5,597,773; 5,703,253; 5,705,661; 6,762,311; EP 0266015 B1, EP 0496470 B1, and EP 1292587 B1, each of which is incorporated herein by reference.

The alkylene oxidation catalyst may have any size and geometric configuration that fits within the process microchannels. The alkylene oxidation catalyst may be in the form of particulates such as particulate solids (e.g., pellets, powder, fibers, and the like) as well as extrudates. Extrudates may have a shape that includes at least one of cylindrical, tubular, polylobular, fluted, or ridged. Particulate alkylene oxidation catalysts may have a weight average diameter from about 100 micrometers (μm) to about 1 millimeter (mm). Thus, the alkylene oxidation catalyst may be a particulate catalyst with a weight average diameter of about 100 μm, about 150 μm, about 200 μm, about 250 μm, about 300 μm, about 350 μm, about 400 μm, about 450 μm, about 500 μm, about 600 μm, about 700 μm, about 800 μm, about 900 μm, about 1 mm, or any range including and/or in between any two of these values. In any embodiment herein, the alkylene oxidation catalyst may be a particulate catalyst having an average outer surface to volume ratio from about 3.0 $mm^{-1}$ to about 50.0 $mm^{-1}$, where such catalysts are preferably extrudates. Thus, the particulate catalyst may have an average outer surface to volume ratio of about 3.0 $mm^{-1}$, about 3.5 $mm^{-1}$, about 4.0 $mm^{-1}$, about 4.5 $mm^{-1}$, about 5.0 $mm^{-1}$, about 5.5 $mm^{-1}$, about 6.0 $mm^{-1}$, about 6.5 $mm^{-1}$, about 7.0 $mm^{-1}$, about 7.5 $mm^{-1}$, about 8.0 $mm^{-1}$, about 8.5 $mm^{-1}$, about 9.0 $mm^{-1}$, about 9.5 $mm^{-1}$, about 10.0 $mm^{-1}$, about 11 $mm^{-1}$, about 12 $mm^{-1}$, about 13 $mm^{-1}$, about 14 $mm^{-1}$, about 15 $mm^{-1}$, about 16 $mm^{-1}$, about 17 $mm^{-1}$, about 18 $mm^{-1}$, about 19 $mm^{-1}$, about 20 $mm^{-1}$, about 21 $mm^{-1}$, about 22 $mm^{-1}$, about 23 $mm^{-1}$, about 24 $mm^{-1}$, about 25 $mm^{-1}$, about 26 $mm^{-1}$, about 27 $mm^{-1}$, about 28 $mm^{-1}$, about 29 $mm^{-1}$, about 30 $mm^{-1}$, about 31 $mm^{-1}$, about 32 $mm^{-1}$, about 33 $mm^{-1}$, about 34 $mm^{-1}$, about 35 $mm^{-1}$, about 36 $mm^{-1}$, about 37 $mm^{-1}$, about 38 $mm^{-1}$, about 39 $mm^{-1}$, about 40 $mm^{-1}$, about 42 $mm^{-1}$, about 44 $mm^{-1}$, about 46 $mm^{-1}$, about 48 $mm^{-1}$, about 50 $mm^{-1}$, or any range including and/or in between any two of these values. In any embodiment herein, the alkylene oxidation catalyst may be a particulate catalyst having a diffusion path from about 50 μm to about 500 μm; the diffusion path may be about 50 μm, about 100 μm, about 150 μm, about 200 μm, about 250 μm, about 300 μm, about 350 μm, about 400 μm, about 450 μm, about 500 μm, or any range including and/or in between any two of these values. In any embodiment herein, it may be the alkylene oxidation catalyst is in the form of a bed of particulate solids, for example, a fixed bed of particulate solids.

The alkylene oxidation catalyst may include a porous support, such as a foam, felt, wad, or a combination of any two or more thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The porous support may have a porosity of at least about 5% as measured by mercury porosimetry and an average pore diameter (sum of pore diameters divided by number of pores) of about 1 μm to about 1000 μm. The porous support may be a porous ceramic or a metal foam. Other porous supports that may be used include carbides, nitrides, and composite materials. The porous support may have a porosity of about 30% to about 99%, or about 60% to about 98%. The porous support may be a metal foam with open pores, where the metal foam has from about 20 pores per inch (ppi) to about 3000 ppi. Thus, the metal foam may have from about 20 ppi to about 1000 ppi, or about 40 to about 120 ppi. The term "ppi" refers to the largest number of pores per inch (in isotropic materials the direction of the measurement is irrelevant; however, in anisotropic materials, the measurement is done in the direction that maximizes pore number).

The alkylene oxidation catalyst may be positioned in a reactor tube upstream and/or downstream of a bed of inert particulates. A bed of inert particulates upstream of the alkylene oxidation catalyst may be used to modify the temperature and/or flow characteristics of the gaseous stream entering the alkylene oxidation catalyst. A bed of inert particulates downstream of the alkylene oxidation catalyst may be used to modify the temperature and/or flow characteristics of the synthetic product flowing out of the alkylene oxidation catalyst. For example, the alkylene oxidation catalyst may be in the form of a bed of particulate solids, and a first bed of inert particulates may be positioned upstream of the alkylene oxidation catalyst and a second bed of inert particulates may be positioned downstream of the alkylene oxidation catalyst. The inert particulates may include, but are not limited to, silicon carbide, steatite, alumina, doped alumina, or a mixture of any two or more thereof. The inert particulates may have a weight average diameter from about 1 μm to about 1000 μm; thus, the inert particulates may have a weight average diameter of about with a weight average diameter of about 1 μm, about 10 μm, about 50 μm, about 100 μm, about 150 μm, about 200 μm, about 250 μm, about 300 μm, about 350 μm, about 400 μm, about 450 μm, about 500 μm, about 600 μm, about 700 μm, about 800 μm, about 900 μm, about 1000 μm, or any range including and/or in between any two of these values.

EXAMPLES

The examples herein are provided to illustrate advantages of the present technology and to further assist a person of ordinary skill in the art with preparing or using the processes of the present technology. The examples herein are also presented in order to more fully illustrate the preferred aspects of the present technology. The examples should in no way be construed as limiting the scope of the present technology, as defined by the appended claims. The examples can include or incorporate any of the variations, embodiments, or aspects of the present technology described above. The variations, embodiments, or aspects described above may also further each include or incorporate the variations of any or all other variations, embodiments, or aspects of the present technology.

The reactor model used in the following examples utilize Fischer-Tropsch reaction kinetics for a catalyst (which includes cobalt) described as Catalyst A in Example 1 of U.S. Pat. Publ. No. 2015/0018439. Such reaction kinetics are readily determined by a person of ordinary skill in the art. The reaction equations utilized in the models were solved simultaneously with heat, mass, and momentum balance equations to determine temperature and pressure profile within the reactor as well as outputs from the reactor model (e.g., CO conversion, methane selectivity, $C_5+$ selectivity).

Figure 17A:
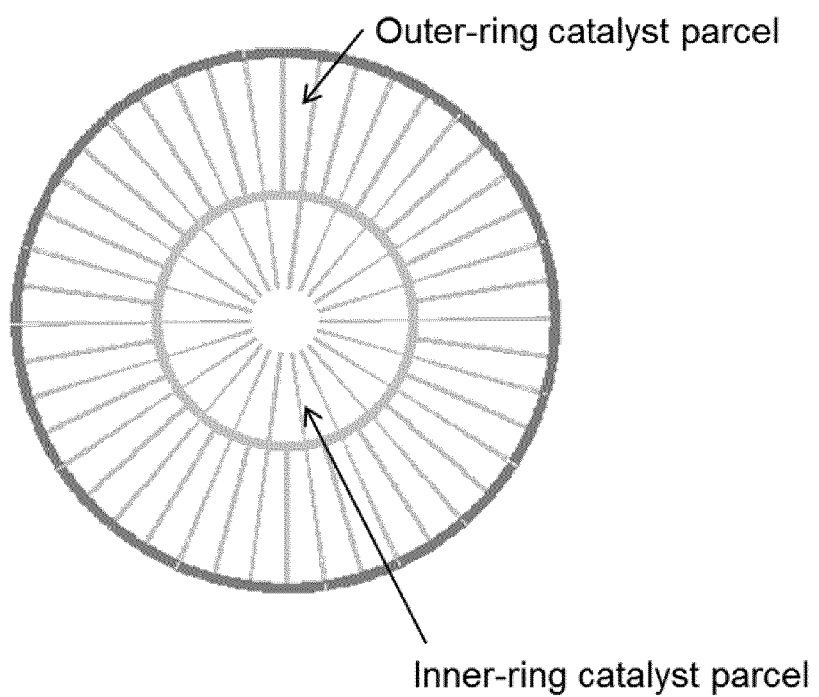
FIGS. 17A-B provide a cross-section (FIG. 17A) and a zoom-in view (FIG. 17B) of a copper heat transfer structure of the present technology in a reactor tube, according to the working examples.
Figure 17B:
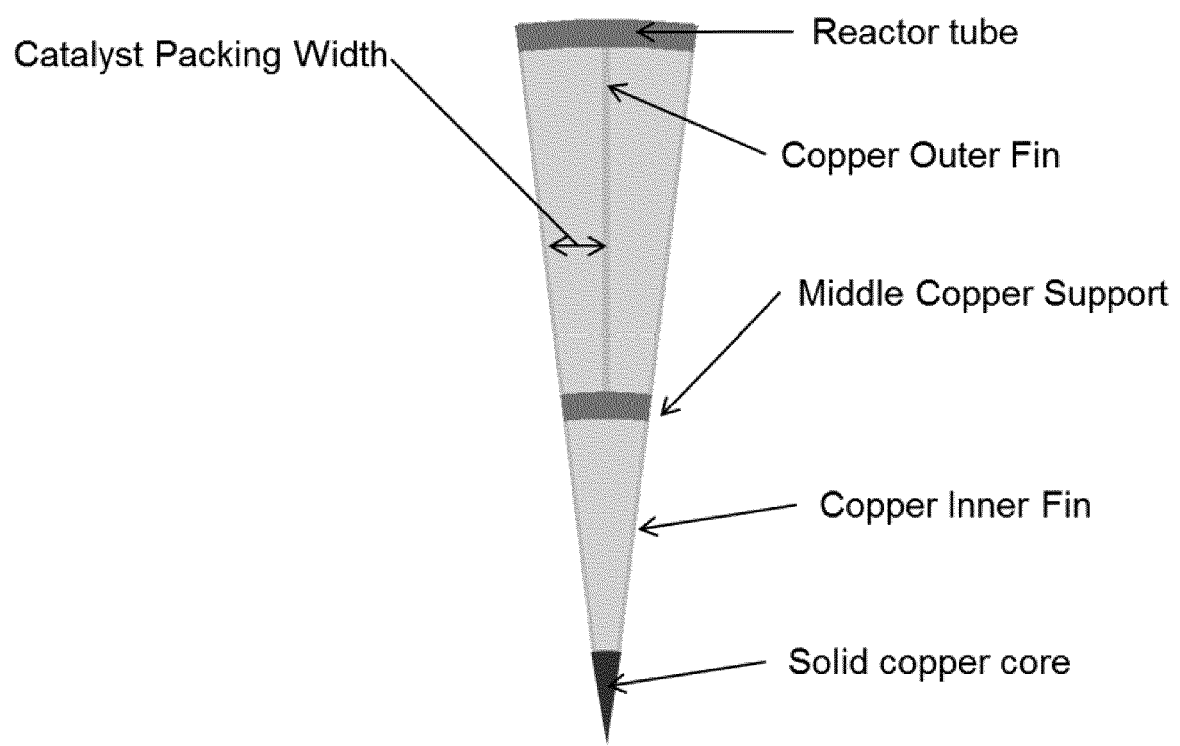
Figure 18A:
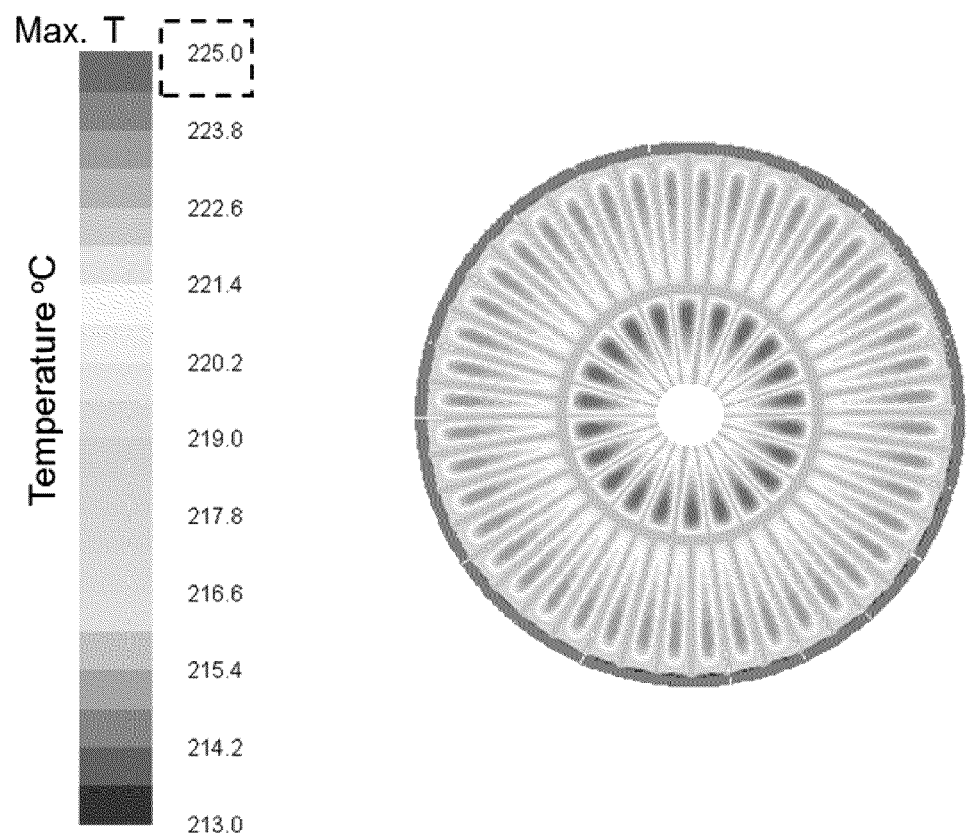
FIGS. 18A-B illustrate reactor modeling results for a particular embodiment of the present technology, where
Figure 18B:
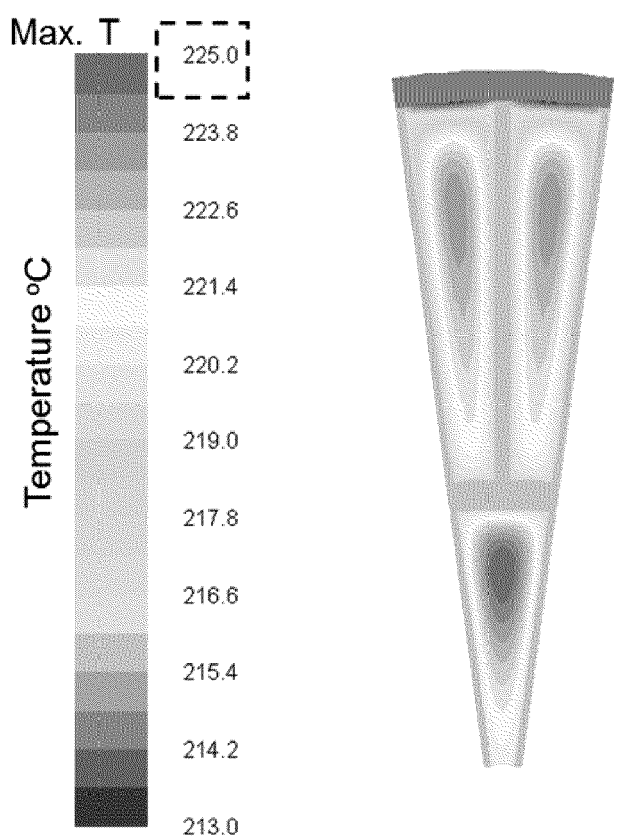
Figure 19:
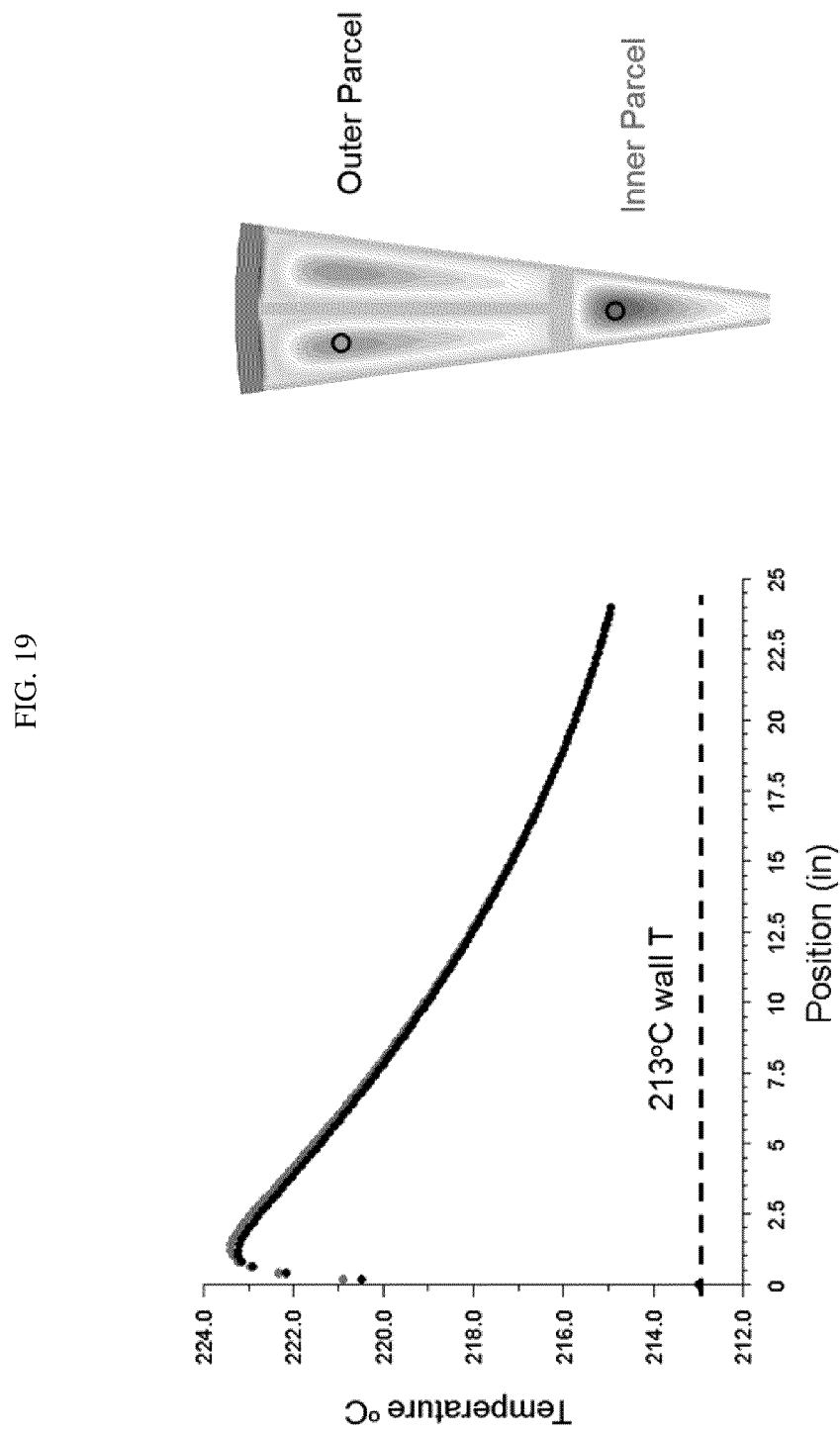
FIG. 19 is a graph illustrating the temperature along the length of the catalyst bed provided in the same modeling results as for FIGS. 18A-B, according to the working examples.
Figure 20A:
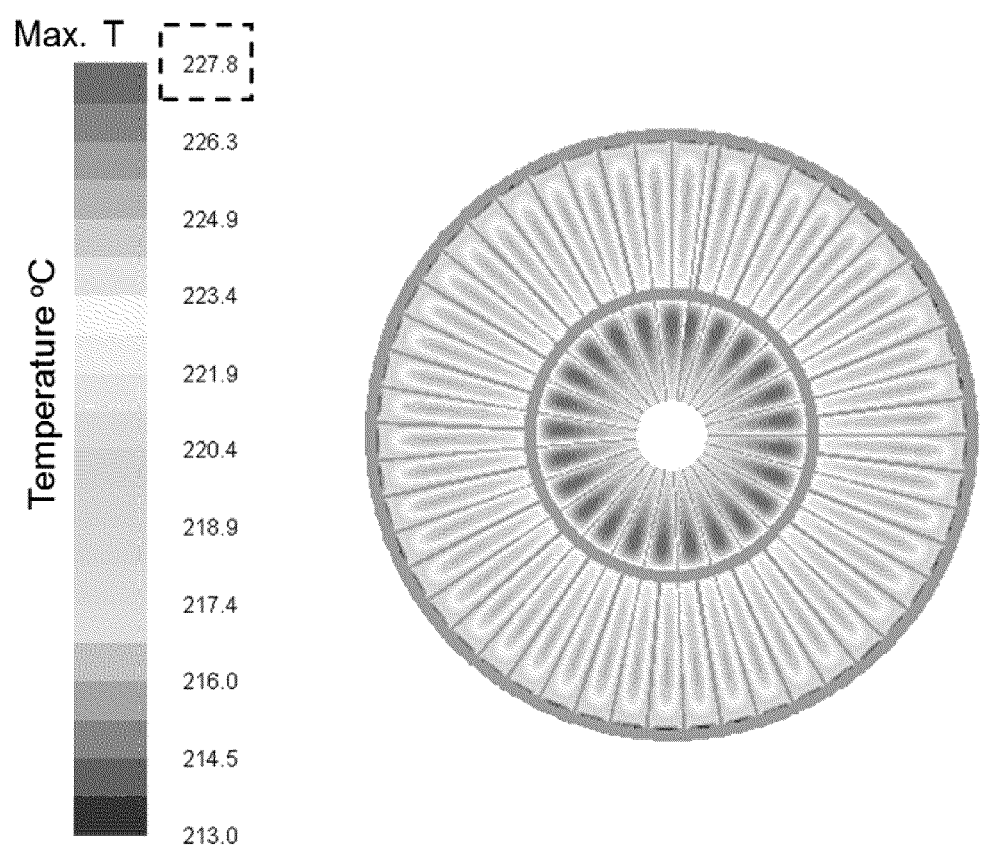
FIGS. 20A-B illustrate reactor modeling results for a particular embodiment of the present technology different than illustrated in FIGS. 18A-B, where
Figure 20B:
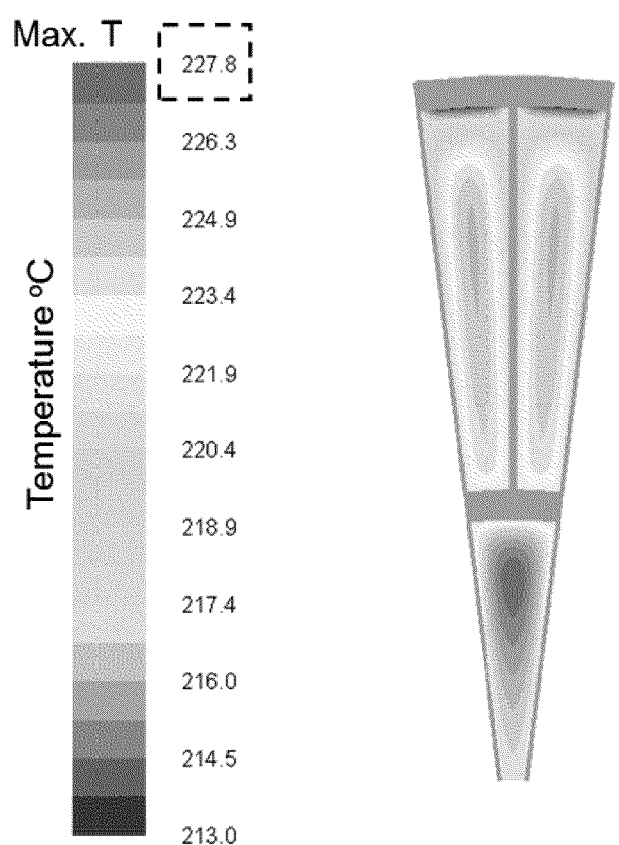
Figure 21:
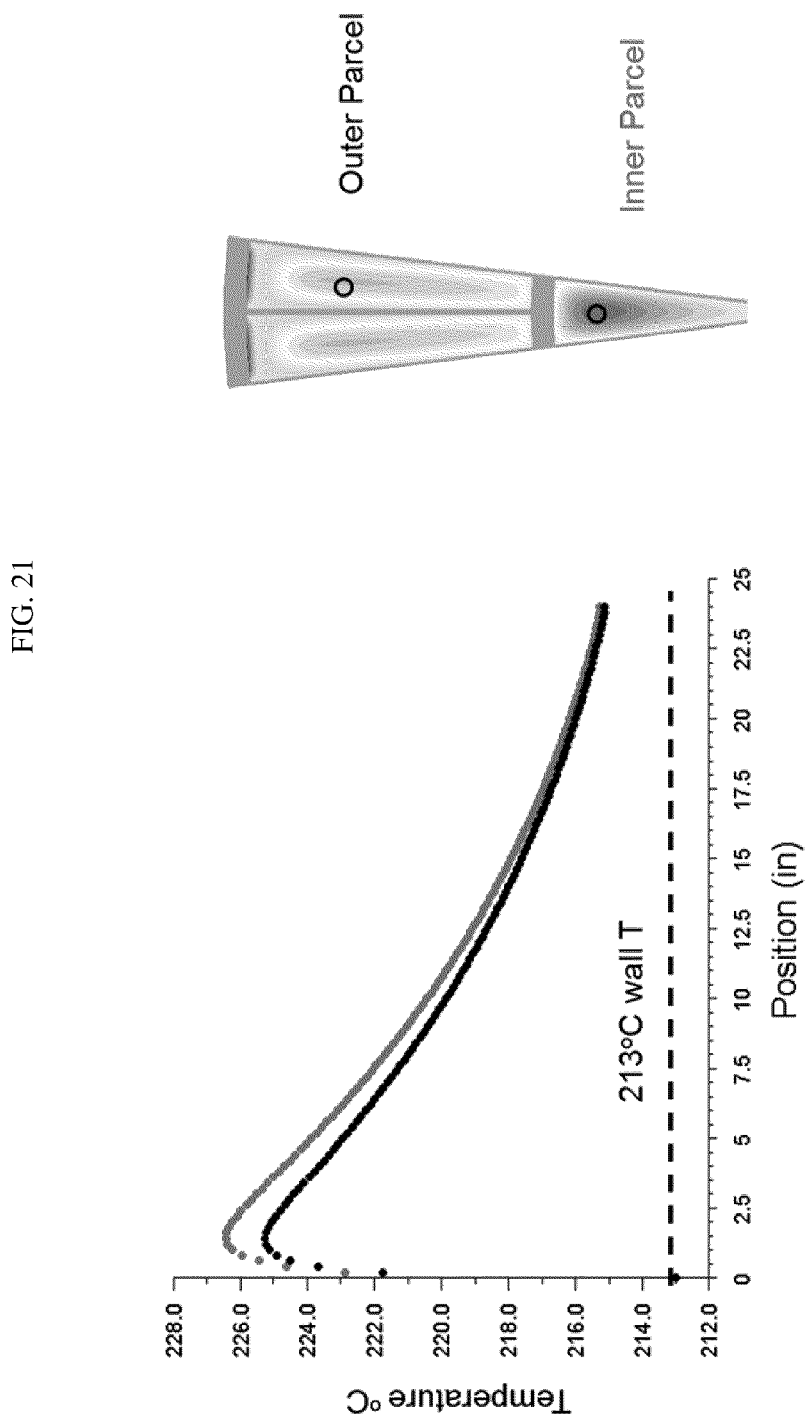
FIG. 21 is a graph illustrating the temperature along the length of the catalyst bed provided in the same modeling results as for FIGS. 20A-B, according to the working examples.

FIGS. 17A-B provide a cross-section (FIG. 17A) and a zoom-in view (FIG. 17B) of a copper heat transfer structure of the present technology in a reactor tube. This heat transfer structure is employed in the reactor model utilizing a $H_2/CO$ ratio of 1.73, 30.7% inerts in the gaseous stream, a catalyst gas hourly space velocity ("GHSV") of 12,650 $hr^{-1}$, an inlet temperature of the gaseous stream of 213° C., and an inlet pressure of 350 psig. The length of the heat transfer structure and the tube length were modeled to be the same value: 24 inches. The activity of the carbon monoxide hydrogenation catalyst used was 75. As indicated in FIG. 17A, each radial fin of the outer ring is in conductive thermal contact with the inner tube wall. Table 1 provides initial parameters explored, while Table 2 and FIGS. 18A-B, 19, 20A-B, & 21 provide the results of this initial study. FIGS. 18A-B & 19 provide the results from Configuration #2, and FIGS. 20A-B & 21 provide the results from Configuration #1.

TABLE 1

| Dimensions | Configuration #1 | Configuration #2 |
|---|---|---|
| Radial fin thickness (in) | 0.006 | 0.01 |
| Inner Tube Wall Diameter (in) | 1 | 1 |
| Tube Length (in) | 24 | 24 |
| Outer Cu Fin height (in) | 0.25 | 0.25 |
| Inner Cu Fin height (in) | 0.17 | 0.15 |
| Middle Cu Support thickness (in) | 0.02 | 0.02 |
| Diameter of Inner Core (in) | 0.12 | 0.16 |
| Number of catalyst parcels-outer ring | 46 | 42 |
| Number of catalyst parcels-inner ring | 23 | 21 |
| Catalyst packing width (in) | 0.011-0.061 | 0.014-0.065 |
| % Catalyst volume | 82 | 77 |
| SA/V ($m^2/m^3$) | 2270 | 2090 |
| Effective Thermal Conductivity Ratio ($k_{eff}/k_{cat}$) | 290 | 314 |
| Percent Surface Area of Inner Tube Wall in Conductive Thermal Contact with Heat Transfer Structure | 9% | 13% |

TABLE 2

| | Catalyst Temp. (° C.) | | Volume | Performance | | | Heat |
|---|---|---|---|---|---|---|---|
| | Maximum | Average Temp. | | CO Conv. | $CH_4$ Selectivity | $C_5+$ Selectivity | flux $Kw/m^2$ |
| Configuration #1 | 227.8 | 218.4 | | 72.2 | 8.3 | 84.3 | 24.5 |
| Configuration #2 | 225.0 | 217.4 | | 71.6 | 7.9 | 85.0 | 22.9 |

Configuration #2 has a SA/V of about 2090 $m^2/m^3$. As illustrated in FIGS. 18A-B, for the 0.01 inch thick copper heat transfer structure of Configuration #2 the catalyst temperature varied from about 213° C. to about 225° C., where FIG. 18A is a cross-section at the highest temperature location in the reactor and FIG. 18B is a zoom-in view of the cross-section. The model also indicated the peak temperature location is about 1.5 inches from the beginning of the catalyst bed in the tube (FIG. 19), where temperature distribution is similar for both the inner and outer catalyst parcels. These data illustrate that thermally stable operation is expected from using a 0.01 inch thick heat transfer structure of this configuration.

Thermally stable operation is similarly expected for Configuration #1 based on the acquired data. Configuration #1 has a SAN of about 2270 $m^2/m^3$. As illustrated in FIGS. 20A-B, for the 0.006 inch thick copper heat transfer structure of Configuration #1 the catalyst temperature varied from about 213° C. to about 227.8° C., where FIG. 20A is a cross-section at the highest temperature location in the reactor and FIG. 20B is a zoom-in view of this cross-section. Similar to Configuration #2, the model indicated the peak temperature location is about 1.5 inches from the beginning of the catalyst bed in the tube (FIG. 21), where the temperature is slightly higher in the inner catalyst parcels.

Comparative Prior Art Tubular Reactor with Low SAN

Figure 22:
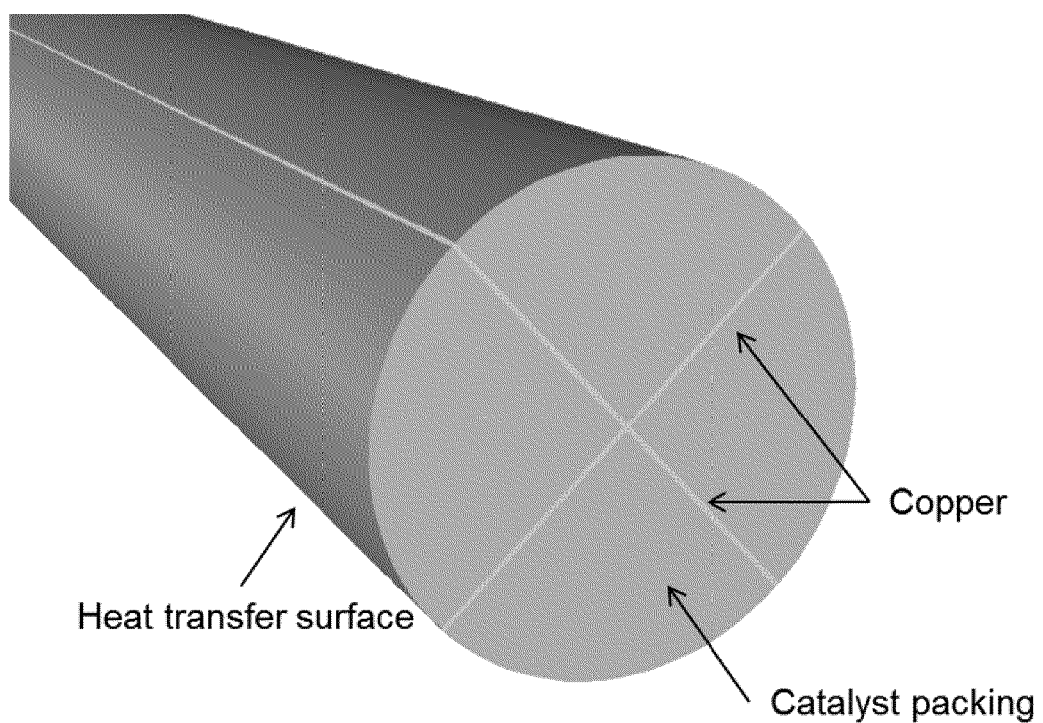
FIG. 22 illustrates a prior art configuration, provided for comparison with the examples according to the present technology.

Two prior art configurations were studied in comparison with the above examples: one with a simple heat transfer structure as illustrated in FIG. 22 (where the inner tube wall is omitted) to provide a SA/V of 358 m²/m³ where the SA/V and another without a heat transfer structure. Modeling parameters included an inner tube diameter of 1 inch, and utilized a gaseous stream with a H$_2$/CO ratio of 1.73 with 30.7% by volume inerts with an inlet temperature of 213° C. and an inlet pressure of 350 psig. The reactor tube length was varied from 197 inches to 24 inches, the catalyst activity (as described previously in this application, i.e., in paragraph [0062]) was varied from about 7.5 to about 37.5, and a catalyst gas hourly space velocity ("GHSV") ranging from 1,000 hr$^{-1}$ to 10,000 hr$^{-1}$. The results of this study are provided in Table 3, where thermal excursion is defined as an uncontrolled increase in the maximum catalyst temperature of 300° C. or above.

TABLE 3

| | | Case | | | |
|---|---|---|---|---|---|
| Row number | Reactor length (in) | Heat Transfer Structure? | Catalyst Activity | GHSV (hr$^{-1}$) | Conclusion Thermal excursion? |
| 1 | 197 | No | 7.5-37.5 | 1,000-10,000 | Yes |
| 2 | 197 | Yes | 7.5-37.5 | 1,000-10,000 | Yes |
| 3 | 24 | Yes | 7.5 | 5,000-10,000 | Yes |
| 4 | 24 | Yes | 7.5 | 1,000 | No |

Row 1 in Table 3 indicates that, for a range of catalyst activities envisaged for the present technology, it is not possible to control the reaction heat generated in a 5 meter (197 inch) long tube for a conventional tubular fixed bed reactor when using 1 inch tubes. The range of space velocities investigated corresponds to those typically considered for fixed bed reactor applications with catalysts less active than 7.5. The present invention seeks to use catalyst activities at 30 or above with space velocities above the range considered for Row 1. Row 2 shows that the reaction remains uncontrollable when a prior art insert is used in the tubes. Row 3 shows that shorter tubes, with space velocities at the more commercially attractive end of the range, are still not feasible due to the uncontrolled temperature excursion. The temperature is found to be controllable at a very low and undesirable space velocity of 1000 h$^{-1}$ when using prior art inserts, as shown in Row 4. This example illustrates that high activity catalysts (with an activity of at least 30 and typically above about 75), as used in the present technology, would simply not be feasible for a tubular reactor using a prior art insert design at high catalyst gas hourly space velocities (i.e., above 10,000 h$^{-1}$).

Figure 23:
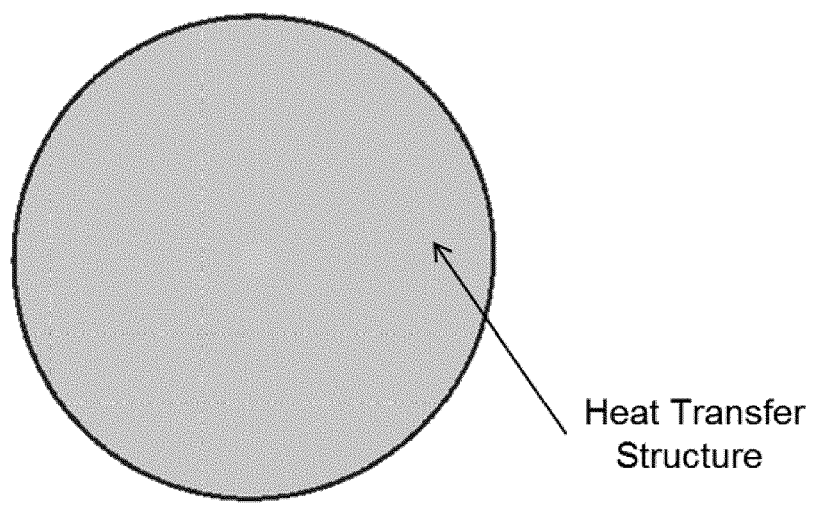
FIG. 23 illustrates a heat transfer structure used in additional modeling studies, according to the working examples.

Advantages of the Present Technology Using Catalysts with Low Thermal Conductivity To further illustrate the advantages of the present technology, a reactor model was studied with the heat transfer structure illustrated in FIG. 23 as well as without a heat transfer structure. In the heat transfer structure of FIG. 23, the heat transfer structure includes a first set of a plurality of fins extending radially from a central support to a first internal circumferential wall of the heat transfer structure to define a first set of channels, a second set of a plurality of fins extending radially from the first internal circumferential wall to a second internal circumferential wall of the heat transfer structure to define a second set of channels, and a third set of a plurality of fins extending radially from the second internal circumferential wall to the inner tube wall where the second internal circumferential wall, the third set of fins, and the inner tube wall define a third set of channels. The thickness of the components are the same as for Configuration #2. A variety of different materials for the composition of Configuration #2 was used in the models in conjunction with a variety of catalysts with different thermal conductivities. These studies were performed in 1 inch and 2 inch diameter tubes.

The results of these surveys are provided in Table 4 (for a reactor with a 1 inch inner tube diameter) and Table 5 (for a reactor with a 2 inch inner tube diameter). Tables 4 & 5 also provide the ratio of the effective thermal conductivity ($k_{eff}$) over the thermal conductivity of the catalyst ($k_{cat}$).

TABLE 4

Thermal conductivity studies with a 1-inch inner tube diameter

| | | Thermal conductivity (W/m-K) | | Effective thermal conductivity (W/m-K) | |
|---|---|---|---|---|---|
| HTS? | HTS material | Catalyst | HTS | $k_{eff}$ | X = $k_{eff}/k_{cat}$ |
| No HTS | N/A | 0.3 | N/A | 0.3 | 1 |
| HTS | Cu | 0.3 | 387 | 94.1 | 314 |
| HTS | Al | 0.3 | 202 | 49.4 | 165 |
| HTS | SS | 0.3 | 19 | 4.9 | 16 |
| No insert | N/A | 1.0 | N/A | 1.0 | 1 |
| HTS | Cu | 1.0 | 387 | 94.9 | 95 |
| HTS | Al | 1.0 | 202 | 50.1 | 50 |
| HTS | SS | 1.0 | 19 | 5.6 | 6 |
| No insert | N/A | 0.1 | N/A | 0.1 | 1 |
| HTS | Cu | 0.1 | 387 | 93.9 | 940 |
| HTS | Al | 0.1 | 202 | 49.1 | 490 |
| HTS | SS | 0.1 | 19 | 4.7 | 47 |

HTS = heat transfer structure of FIG. 23
SS = stainless steel

TABLE 5

Thermal conductivity studies with a 2-inch inner tube diameter

| | | Thermal conductivity (W/m-K) | | Effective thermal conductivity (W/m-K) | |
|---|---|---|---|---|---|
| HTS? | HTS material | Catalyst | HTS | $k_{eff}$ | $k_{eff}/k_{cat}$ |
| No HTS | N/A | 0.3 | N/A | 0.3 | 1 |
| HTS | Cu | 0.3 | 387 | 116.9 | 390 |
| HTS | Al | 0.3 | 202 | 61.5 | 205 |
| HTS | SS | 0.3 | 19 | 6.1 | 20 |
| No HTS | N/A | 1.0 | N/A | 1.0 | 1 |
| HTS | Cu | 1.0 | 387 | 117.6 | 118 |
| HTS | Al | 1.0 | 202 | 62.2 | 62 |
| HTS | SS | 1.0 | 19 | 6.7 | 7 |
| No HTS | N/A | 0.1 | N/A | 0.1 | 1 |
| HTS | Cu | 0.1 | 387 | 116.7 | 1167 |
| HTS | Al | 0.1 | 202 | 61.3 | 613 |
| HTS | SS | 0.1 | 19 | 5.9 | 59 |

HTS = heat transfer structure of FIG. 23
SS = stainless steel

As illustrated by these data, when using catalysts with low thermal conductivity but with high activity, the $k_{eff}/k_{cat}$ is dramatically increased by utilizing heat transfer structures of the present technology. This is important, as heat removal from high activity catalysts is imperative for desirable output. It also indicates that aluminum, copper, and alloys including aluminum or copper would provide for higher $k_{eff}/k_{cat}$. Thus, this example further illustrates that the present technology allows for use of high activity catalysts with low thermal conductivity by dramatically increasing the thermal conductivity of the system. Exemplary high activity catalysts that may benefit from the present technology include, but are not limited, to those described in U.S. Pat. Publ. No. 2015/0018439.

Conductive Thermal contact between the Inner Tube Wall and the Heat Transfer Structure The advantages of the present technology are further illustrated by analysis of the conductive thermal contact between the inner tube wall containing the carbon monoxide hydrogenation catalyst and the heat transfer structure.

1-Inch Inner Tube Wall Diameter Studies

Figure 24A:
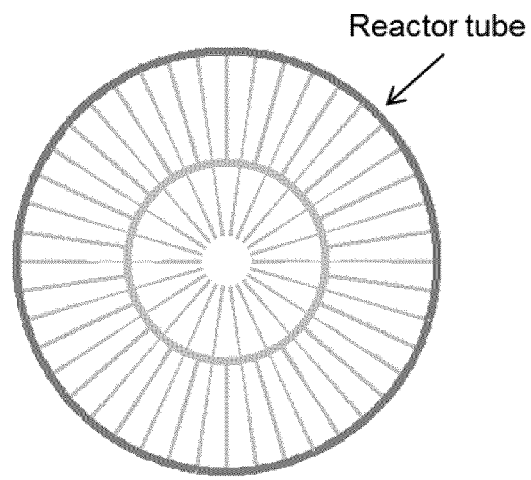
FIGS. 24A-D illustrate the points of conductive thermal contact by several heat transfer structures with the inner tube wall. The surface area of the inner tube wall in conductive thermal contact with the different heat transfer structures is 13% (FIG. 24A), 6.5% (FIG. 24B), 50% (FIG. 24C), and 100% (FIG. 24D).
Figure 24B:
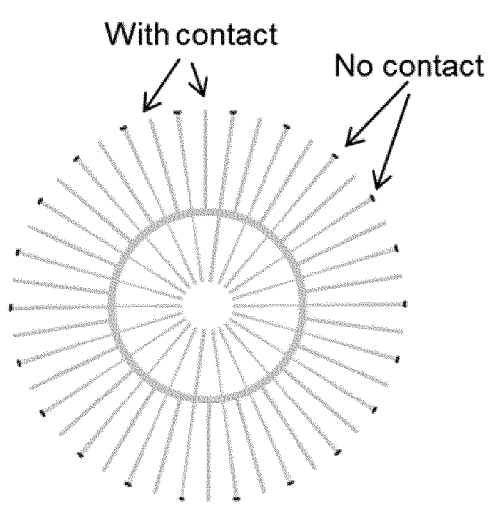
Figure 24C:
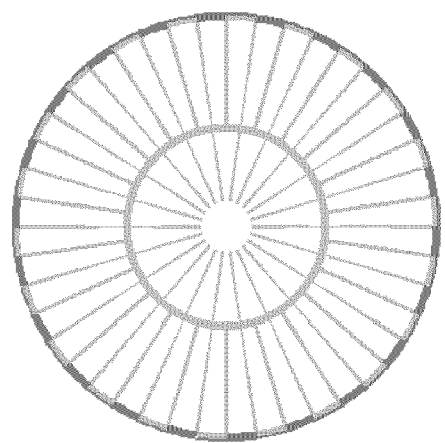
Figure 24D:
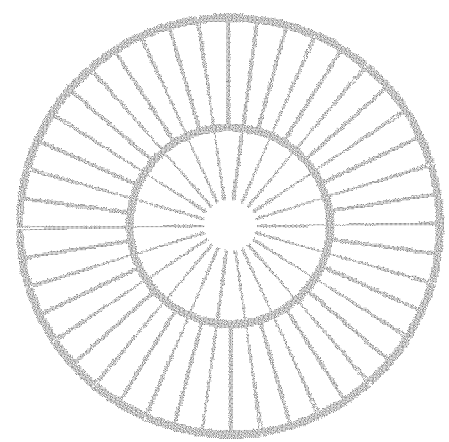

The copper heat transfer structure of Configuration #2 was compared against nearly identical variants where the percentage of the inner tube surface area in conductive thermal contact was varied. FIGS. 24A-D illustrates the points of conductive thermal contact by the heat transfer structure with the inner tube wall. For Configuration #2 (FIG. 24A), 13% of the surface area of the inner tube wall is in conductive thermal contact via the contact between the tips of the outer radial fins with the inner tube wall. FIG. 24B illustrates a variant of Configuration #2 where every other outer radial fin is in conductive thermal contact with the inner tube wall such that 6.5% of the surface area of the inner tube wall is in contact. FIG. 24C illustrates a variant of Configuration #2 with 50% conductive thermal contact. FIG. 24D is a variant of Configuration #2 that includes an external circumferential wall (i.e., external to the remainder of the heat transfer structure) that ensures 100% of the inner tube wall containing the catalyst is in physical and conductive thermal contact with the heat transfer structure.

These variants were modeled using the same reactor parameters (a 24 inch long reactor tube with a 1 inch inner tube diameter) and reaction conditions as used to evaluate Configuration #2. The results of this study for the variants alongside Configuration #2 are provided in Table 6 below.

TABLE 6

| Surface Area of Inner Tube Wall Contacted (%) | Catalyst Temp. (° C.) | | Performance | | |
|---|---|---|---|---|---|
| | Maximum | Average Volume Temp. | CO Conv. | CH$_4$ Selectivity | C$_5$+ Selectivity |
| 100% | 221.0 | 215.6 | 70.1 | 7.3 | 85.9 |
| 50% | 222.3 | 216.2 | 70.8 | 7.3 | 85.2 |
| 13% (Conf. #2) | 225.0 | 217.4 | 71.6 | 7.9 | 85.0 |
| 6.5% | 235.1 | 220.8 | 74.1 | 9.7 | 82.0 |

As illustrated by this data, the process is stable and without danger of thermal runaway for the ranges of conductive thermal contact tested, where higher percentages of conductive thermal contact with the inner tube wall provide for higher C$_5$+ selectivities, translating into higher production of desirable hydrocarbon product in a Fischer-Tropsch reaction.

2-Inch Inner Tube Wall Diameter Studies

Figure 25A:
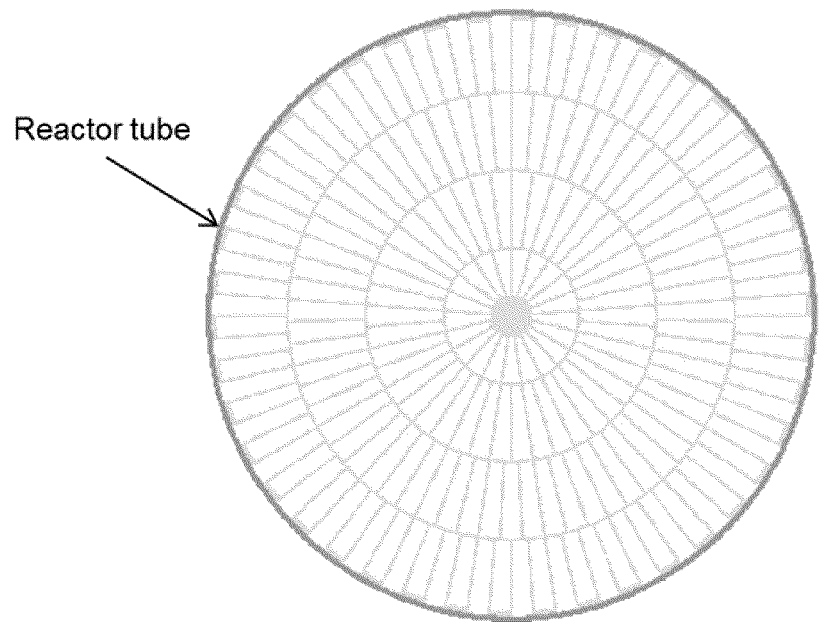
FIGS. 25A-B illustrate further heat transfer structures modeled to illustrate the present technology. The heat transfer structure of FIG. 25B provides for 100% of the surface area of the inner tube wall to be in conductive thermal contact with the heat transfer structure, whereas in FIG. 25A there is a discontinuous external circumferential wall such that 50% of the surface area of the inner tube wall is in conductive thermal contact with the heat transfer structure.
Figure 25B:
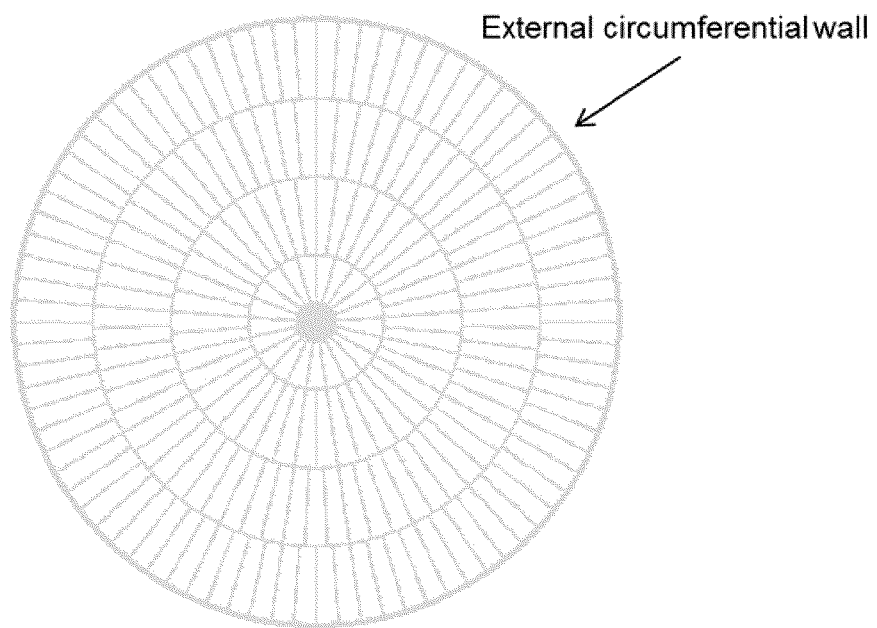

In order to evaluate a reactor tube with a 2 inch inner diameter, copper heat transfer structures illustrated by FIG. 23 above as well those illustrated by FIGS. 25A-B were modeled. The copper heat transfer structure of FIG. 23 provides for 13% of the surface area of the inner tube wall to be in conductive thermal contact with the heat transfer structure. The heat transfer structure of FIG. 25B includes an external circumferential wall such that 100% of the surface area of the inner tube wall is in conductive thermal contact, whereas in FIG. 25A there is a discontinuous external circumferential wall such that 50% of the surface area of the inner tube wall is in conductive thermal contact with the heat transfer structure—an example of at least partial conductive thermal contact throughout the surface area of the inner tube wall containing the carbon monoxide hydrogenation catalyst.

The heat transfer structures illustrated in FIGS. 23 & 25A-B were modeled using the same reactor parameters and reactions conditions as used to evaluate Configuration #2, with the exception that the inner wall diameter was 2 inches. The results of these studies are provided in Table 7.

TABLE 7

| Surface Area of Inner Tube Wall Contacted (%) | Catalyst Temp. (° C.) | | Performance | | |
|---|---|---|---|---|---|
| | Maximum | Average Volume Temp. | CO Conv. | CH$_4$ Selectivity | C$_5$+ Selectivity |
| 100% | 234.5 | 219.2 | 73.0 | 8.8 | 83.4 |
| 50% | 241.1 | 221.3 | 73.8 | 10.2 | 81.2 |
| 13% | 250.5 | 223.7 | 74.9 | 13.0 | 76.8 |

As illustrated in Table 7, under the tested conditions with an inner wall diameter of 2 inches, the heat transfer structure of FIG. 25A provided acceptable results while the heat transfer structure of FIG. 25B provided even more desirable C$_5$+ selectivity while reducing methane selectivity. Thus, this example further illustrates the advantages of the present technology in using high activity carbon monoxide hydrogenation catalysts.

3-Inch Inner Tube Wall Diameter Studies

Figure 26:
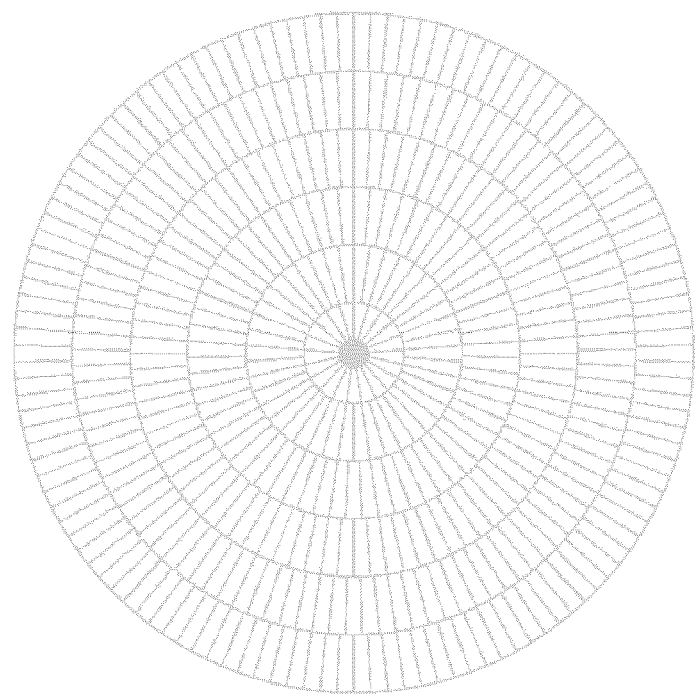
FIG. 26 illustrates yet another heat transfer structure modeled in the working examples. The structure of FIG. 26 includes an external circumferential wall such that 100% of the surface area of the inner tube wall is in conductive thermal contact with the heat transfer structure.

In order to evaluate a reactor tube with a 3 inch inner diameter, a copper heat transfer structure as illustrated by FIG. 26 was modeled. The structure of FIG. 26 includes an external circumferential wall such that 100% of the surface area of the inner tube wall is in conductive thermal contact. The respective physical parameters for the copper heat transfer structure are provided in Table 8 below.

TABLE 8

| Dimensions | Modeled Structure of FIG. 26 |
|---|---|
| Diameter of Inner Copper Core (in) | 0.12 |
| Interior and Exterior Cu Support thicknesses (in) | 0.02 |

| Ring parameters | Number of catalyst parcels | Cu Fin height (in) |
|---|---|---|
| Ring 1 (inner) | 21 | 0.15 |
| Ring 2 | 42 | 0.25 |
| Ring 3 | 63 | 0.25 |
| Ring 4 | 84 | 0.25 |
| Ring 5 | 105 | 0.25 |
| Ring 6 (outer) | 126 | 0.25 |
| Catalyst packing width (in) | 0.014-0.065 | |
| % Catalyst volume | 83 | |
| SA/V (m$^2$/m$^3$) | 1760 | |

TABLE 8-continued

| | |
|---|---|
| Percent Surface Area of Inner Tube Wall in Conductive Thermal Contact with Heat Transfer Structure | 100% |

The model was run using the same reactor parameters and reactions conditions as used to evaluate Configuration #2 (a reactor tube length and heat transfer structure length of 24 inches, etc.), with the exception that the inner wall diameter was 3 inches, where it was found that there was thermal excursion.

The model was then tested using the same reactor parameters and reactions conditions as used to evaluate Configuration #2, with the exception that the inner wall diameter was 3 inches and the tested catalyst activities were 30 and 37.5. The results of these studies are provided in Table 9.

TABLE 9

| | Catalyst Temp. (° C.) | | Performance | | |
|---|---|---|---|---|---|
| Catalyst Activity | Maximum | Volume Average Temp. | CO Conv. | $CH_4$ Selectivity | $C_5+$ Selectivity |
| 30 | 231.4 | 221.0 | 43.4 | 9.2 | 83.8 |
| 37.5 | 238.5 | 222.8 | 53.0 | 10.2 | 82.0 |

As illustrated above, with a catalyst activity of 37.5 acceptable results are realized, and more desirable $C_5+$ selectivity with reducing methane selectivity is exhibited at a catalyst activity of 30.

To explore increasing the CO conversion in 3-inch diameter tubes, a longer tube length of 36 inches was modeled with a catalyst activity of 37.5. The model was run using the same reactor parameters and reactions conditions as used to evaluate Configuration #2, with the exception that the inner wall diameter was 3 inches, the tube length was 36 inches, and the catalyst activity was 37.5. Furthermore, to facilitate higher conversion and prevent thermal runaway in this particular model, the GHSV was set to 8,400 $hr^{-1}$. The result of this model is provided in Table 10 below alongside the 24 inch long, 3 inch diameter results (previously provided in Table 9).

TABLE 10

| Reactor Tube Length (in) | GHSV ($hr^{-1}$) | Catalyst Temp. (° C.) | | Performance | | | Pressure Drop (psi) |
|---|---|---|---|---|---|---|---|
| | | Maximum | Volume Average Temp. | CO Conv. | $CH_4$ Selectivity | $C_5+$ Selectivity | |
| 36 | 8,400 | 243.6 | 221.6 | 70.8 | 10.8 | 80.4 | 47 |
| 24 (Table 9) | 12,650 | 238.5 | 222.8 | 53.0 | 10.2 | 82.0 | 25 |

As illustrated above, a higher CO conversion in the 3-inch diameter reactor tubes may be achieved with a longer tube length but with lower catalyst gas hourly space velocity and increased pressure drop.

Figure 27:
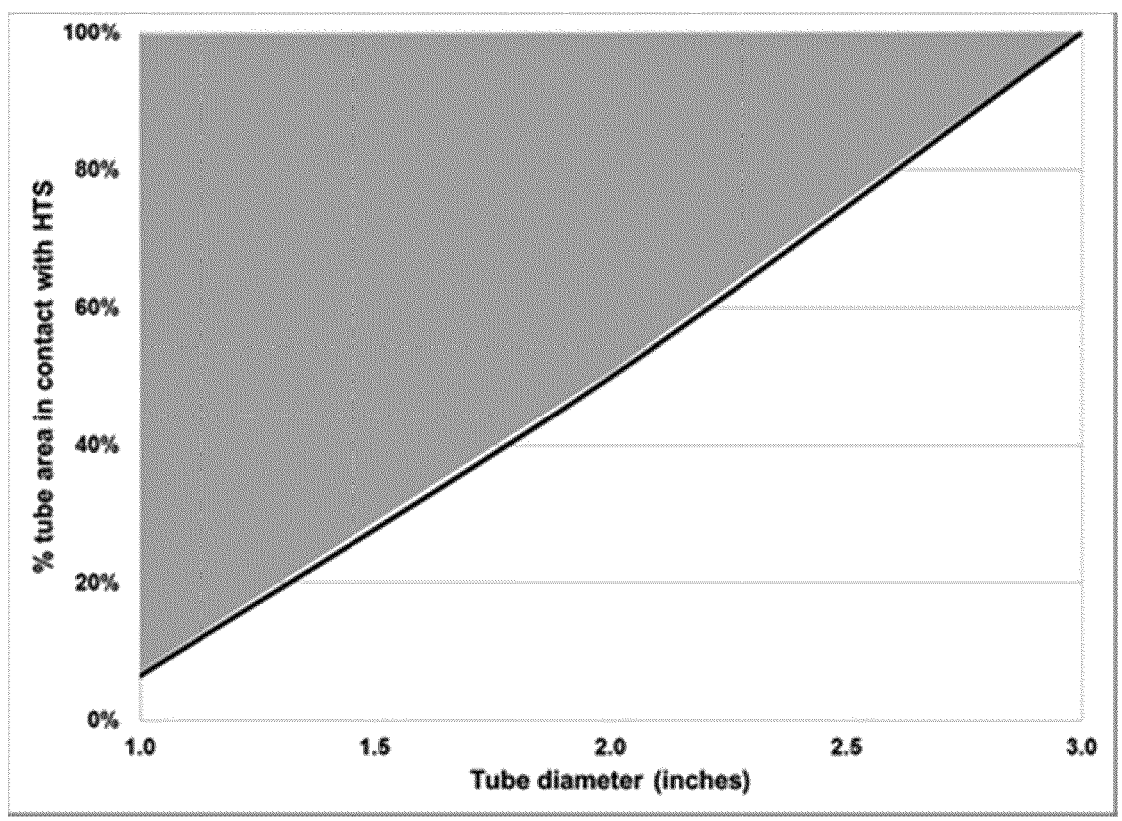
FIG. 27 illustrates a rough correlation between the inner tube diameter and the percent of the surface area of the inner tube wall in conductive thermal contact the heat transfer structure (HTS) for models providing similar $C_5$+ selectivities.

Furthermore, given the data above, a general correlation may be illustrated between the inner tube diameter and the percent of the surface area of the inner tube wall in conductive thermal contact the heat transfer structure (HTS), as provided in Table 11 and graphically in FIG. 27, for models providing similar $C_5+$ selectivities. Notably, for the 3 inch inner tube diameter model, a lower catalyst activity was used than for the examples utilizing a 1 inch and 2 inch inner tube diameter.

TABLE 11

| Inner Tube Diameter (in) | Surface Area of Inner Tube Wall Contacted (%) | Volume Average Catalyst Temp. (° C.) | | Performance | | |
|---|---|---|---|---|---|---|
| | | | | CO Conv. | $CH_4$ Selectivity | $C_5+$ Selectivity |
| 1 (Table 6) | 6.5% | 235.1 | 220.8 | 74.1 | 9.7 | 82.0 |
| 2 (Table 7) | 50% | 241.1 | 221.3 | 73.8 | 10.2 | 81.2 |
| 3 (Table 9) | 100% | 238.5 | 222.8 | 53.0 | 10.2 | 82.0 |

By adjusting the inner tube diameter and/or the percent of the surface area of the inner tube wall in conductive thermal contact the HTS so that the result falls within the shaded area in FIG. 27, it is expected that further enhancements to one or more of CO conversion, methane selectivity, and $C_5+$ selectivity would be achieved. Thus, not only does the present disclosure guide one of ordinary skill in the art on how to modify the percent of the surface area of the inner tube wall in conductive thermal contact the heat transfer structure when modifying tube diameter, the present disclosure also guides one of ordinary skill in the art on how to adjust the activity of the catalyst in view of the parameters provided in the present disclosure.

The present technology is not to be limited in terms of the particular figures and examples described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, or labeled compounds, which can, of course, vary. It is also to be understood that the terminology used herein is for the purpose of describing particular aspects only, and is not intended to be limiting.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A process for the conversion of synthesis gas, the process comprising contacting in a tubular reactor a gaseous stream comprising synthesis gas with a carbon monoxide hydrogenation catalyst to produce a synthetic product; wherein the tubular reactor comprises
 a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube;
 a reactor outlet located downstream of the reactor inlet in fluid communication with the one or more reactor tubes; and
 a cooling medium in contact with the one or more reactor tubes;
 wherein
 the diameter of the inner tube wall is from 20 mm to 80 mm;
 the carbon monoxide hydrogenation catalyst exhibits a conversion rate of at least 30 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm;
 the heat transfer structure comprises a network of heat conducting surfaces in conductive thermal contact with a portion of the carbon monoxide hydrogenation catalyst and wherein the heat transfer structure is in at least partial conductive thermal contact throughout the surface area of the inner tube wall containing the carbon monoxide hydrogenation catalyst; and
 at least one of
  a ratio of effective thermal conductivity of the heat transfer structure and the carbon monoxide hydrogenation catalyst with the inner tube wall over thermal conductivity of the carbon monoxide hydrogenation catalyst of at least about 50:1; and
  a total combined surface area of the heat transfer structure and inner tube wall containing the carbon monoxide hydrogenation catalyst per volume of the carbon monoxide hydrogenation catalyst (the "SA/V") from about 500 $m^2/m^3$ to about 4000 $m^2/m^3$.

B. The process of Paragraph A, wherein at least about 5% of the surface area of the inner tube wall containing the carbon monoxide hydrogenation catalyst is in conductive thermal contact with the heat transfer structure.

C. The process of Paragraph A or Paragraph B, wherein at least about 10% of surface area of the inner tube wall containing the carbon monoxide hydrogenation catalyst is in conductive thermal contact with the heat transfer structure.

D. The process of any one of Paragraphs A-C, wherein the heat transfer structure comprises steel, aluminum, copper, an alloy thereof, or a combination of any two or more thereof.

E. The process of any one of Paragraphs A-D, wherein the heat transfer structure comprises aluminum, copper, an alloy thereof, or a combination of any two or more thereof.

F. The process of any one of Paragraphs A-E, wherein the heat transfer structure comprises a combination of steel and aluminum, steel and copper, aluminum and copper, or steel, aluminum, and copper.

G. The process of any one of Paragraphs A-F, wherein the contacting step further comprises
 maintaining at least about 50% carbon monoxide conversion per pass in the one or more reactor tubes.

H. The process of any one of Paragraphs A-G, wherein a catalyst gas hourly space velocity of the gaseous stream in the tubular reactor is from about 5,000 $hr^{-1}$ to about 20,000 $hr^{-1}$.

I. The process of any one of Paragraphs A-H, wherein the catalyst gas hourly space velocity of the gaseous stream in the tubular reactor is at least about 5,000 $hr^{-1}$.

J. The process of any one of Paragraphs A-I, wherein the temperature of the gaseous stream at the reactor inlet is about 160° C. to about 265° C.

K. The process of any one of Paragraphs A-J, wherein the carbon monoxide hydrogenation catalyst exhibits a conversion rate of about 45 millimoles to about 200 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm.

L. The process of any one of Paragraphs A-K, wherein the carbon monoxide hydrogenation catalyst exhibits a conversion rate of about 100 millimoles to about 175 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm.

M. The process of any one of Paragraphs A-L, wherein the carbon monoxide hydrogenation catalyst comprises Co.

N. The process of any one of Paragraphs A-M, wherein the carbon monoxide hydrogenation catalyst is a particulate catalyst.

O. The process of any one of Paragraphs A-N, wherein the carbon monoxide hydrogenation catalyst is a particulate catalyst having a weight average diameter from about 100 micrometers (μm) to about 1 millimeter (mm).

P. The process of any one of Paragraphs A-O, wherein the carbon monoxide hydrogenation catalyst is a particulate catalyst having an average outer surface to volume ratio from about 3.0 $mm^{-1}$ to about 50.0 $mm^{-1}$.

Q. The process of any one of Paragraphs A-P, wherein the carbon monoxide hydrogenation catalyst is a particulate catalyst having a diffusion path from about 50 μm to about 500 μm.

R. The process of any one of Paragraphs A-Q, wherein the carbon monoxide hydrogenation catalyst comprises a Co loading from about 25 wt % to about 56 wt %.

S. The process of any one of Paragraphs A-R, wherein the carbon monoxide hydrogenation catalyst comprises a particulate Fischer-Tropsch catalyst.

T. The process of any one of Paragraphs A-S, wherein the carbon monoxide hydrogenation catalyst comprises a particulate catalyst fused to a ceramic support.

U. The process of any one of Paragraphs A-T, wherein the synthetic product comprises hydrocarbons.

V. The process of any one of Paragraphs A-U, wherein the synthetic product comprises $C_5$+ hydrocarbons.

W. The process of any one of Paragraphs A-V, wherein the cooling medium temperature is about 160° C. to about 265° C.

X. The process of any one of Paragraphs A-W, wherein the heat transfer structure comprises a random network of heat conducting surfaces.

Y. The process of any one of Paragraphs A-X, wherein the heat transfer structure comprises an ordered network of heat conducting surfaces.

Z. The process of any one of Paragraphs A-Y, wherein the heat transfer structure comprises a plurality of fins extending radially from a central support.

AA. The process of any one of Paragraphs A-Z, wherein the heat transfer structure comprises
a first set of a plurality of fins extending radially from a central support to an internal circumferential wall of the heat transfer structure to define a first set of channels;
a second set of a plurality of fins extending radially from the circumferential wall to the inner tube wall, wherein each fin of the second set is in conductive thermal contact with the inner tube wall to define a second set of channels.

AB. The process of any one of Paragraphs A-AA, wherein the process further comprises introducing the gaseous stream through the reactor inlet at a pressure from about 250 psig to about 1,000 psig.

AC. The process of any one of Paragraphs A-AB, wherein a ratio of $H_2/CO$ in the synthesis gas from about 1.6 to about 2.0.

AD. A process for the conversion of synthesis gas, the process comprising contacting in a tubular reactor a gaseous stream comprising synthesis gas with a particulate Fischer-Tropsch catalyst comprising Co to produce a synthetic product comprising hydrocarbons,
wherein the tubular reactor comprises
a reactor inlet in fluid communication with one or more reactor tubes wherein each reactor tube comprises a tube inlet, a tube outlet located downstream of the tube inlet, an inner tube wall, an outer tube wall, a heat transfer structure within the reactor tube, and a volume of the particulate Fischer-Tropsch catalyst within the reactor tube;
a reactor outlet located downstream of the reactor inlet in fluid communication with the one or more reactor tubes; and
a cooling medium in contact with the one or more reactor tubes;
wherein
the diameter of the inner tube wall is from 20 mm to 50 mm and each reactor tube comprises a length containing the particulate Fischer-Tropsch catalyst that is less than about 5 meters;
at least about 5% of surface area of the inner tube wall containing the carbon monoxide hydrogenation catalyst is in conductive thermal contact with the heat transfer structure;
the particulate Fischer-Tropsch catalyst exhibits a conversion rate of at least 30 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using particulate Fischer-Tropsch catalyst with a weight average diameter of less than 65 μm;
the heat transfer structure comprises a network of heat conducting surfaces in conductive thermal contact with a portion of the volume of carbon monoxide hydrogenation catalyst and wherein the heat transfer structure is in at least partial conductive thermal contact throughout the surface area of the inner tube wall containing the particulate Fischer-Tropsch catalyst; and
at least one of
a ratio of effective thermal conductivity of the heat transfer structure and the particulate Fischer-Tropsch catalyst with the inner tube wall over thermal conductivity of the particulate Fischer-Tropsch catalyst of at least about 50:1; and
a total combined surface area of the heat transfer structure and inner tube wall containing the particulate Fischer-Tropsch catalyst per volume of the particulate Fischer-Tropsch catalyst (the "SA/V") from about 500 $m^2/m^3$ to about 4000 $m^2/m^3$;
the process further comprising introducing the gaseous stream through the reactor inlet at a pressure from about 250 psig to about 1,000 psig with a ratio of $H_2/CO$ in the synthesis gas from about 1.6 to about 2.0.

AE. The process of Paragraph AD, wherein at least about 10% of surface area of the inner tube wall containing the carbon monoxide hydrogenation catalyst is in conductive thermal contact with the heat transfer structure.

AF. The process of Paragraph AD or Paragraph AE, wherein the heat transfer structure comprises steel, aluminum, copper, an alloy thereof, or a combination of any two or more thereof.

AG. The process of any one of Paragraphs AD-AF, wherein the heat transfer structure comprises aluminum, copper, an alloy thereof, or a combination of any two or more thereof.

AH. The process of any one of Paragraphs AD-AG, wherein the heat transfer structure comprises a combination of steel and aluminum, steel and copper, aluminum and copper, or steel, aluminum, and copper.

AI. The process of any one of Paragraphs AD-AH, wherein the contacting step further comprises
maintaining at least about 50% carbon monoxide conversion per pass in the one or more reactor tubes.

AJ. The process of any one of Paragraphs AD-AI, wherein a catalyst gas hourly space velocity of the gaseous stream in the tubular reactor is from about 5,000 $hr^{-1}$ to about 20,000 $hr^{-1}$.

AK. The process of any one of Paragraphs AD-AJ, wherein the catalyst gas hourly space velocity of the gaseous stream in the tubular reactor is at least about 5,000 $hr^{-1}$.

AL. The process of any one of Paragraphs AD-AK, wherein the temperature of the gaseous stream at the reactor inlet is about 160° C. to about 265° C.

AM. The process of any one of Paragraphs AD-AL, wherein the particulate Fischer-Tropsch catalyst exhibits a conversion rate of about 45 millimoles to about 200 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm.

AN. The process of any one of Paragraphs AD-AM, wherein the particulate Fischer-Tropsch catalyst exhibits a conversion rate of about 100 millimoles to about 175 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm.

AO. The process of any one of Paragraphs AD-AN, wherein the particulate Fischer-Tropsch catalyst has a weight average diameter from about 100 micrometers (μm)) to about 1 millimeter (mm).

AP. The process of any one of Paragraphs AD-AO, wherein the particulate Fischer-Tropsch catalyst has an average outer surface to volume ratio from about 3.0 $mm^{-1}$ to about 50.0 $mm^{-1}$.

AQ. The process of any one of Paragraphs AD-AP, wherein the particulate Fischer-Tropsch catalyst has a diffusion path from about 50 μm to about 500 μm.

AR. The process of any one of Paragraphs AD-AQ, wherein the particulate Fischer-Tropsch catalyst comprises a Co loading from about 25 wt % to about 56 wt %.

AS. The process of any one of Paragraphs AD-AR, wherein the particulate Fischer-Tropsch catalyst is provided on a ceramic support.

AT. The process of any one of Paragraphs AD-AS, wherein the synthetic product comprises $C_5+$ hydrocarbons.

AU. The process of any one of Paragraphs AD-AT, wherein the cooling medium temperature is about 160° C. to about 265° C.

AV. The process of any one of Paragraphs AD-AU, wherein the heat transfer structure comprises a random network of heat conducting surfaces.

AW. The process of any one of Paragraphs AD-AV, wherein the heat transfer structure comprises an ordered network of heat conducting surfaces.

AX. The process of any one of Paragraphs AD-AW, wherein the heat transfer structure comprises a plurality of fins extending radially from a central support.

AY. The process of any one of Paragraphs AD-AX, wherein the heat transfer structure comprises
a first set of a plurality of fins extending radially from a central support to an internal circumferential wall of the heat transfer structure to define a first set of channels;
a second set of a plurality of fins extending radially from the circumferential wall to the inner tube wall, wherein each fin of the second set is in conductive thermal contact with the inner tube wall to define a second set of channels.

AZ. A process for the conversion of synthesis gas, the process comprising contacting in a tubular reactor a gaseous stream comprising synthesis gas with a carbon monoxide hydrogenation catalyst to produce a synthetic product;
wherein the tubular reactor comprises
a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube;
a reactor outlet located downstream of the reactor inlet in fluid communication with the one or more reactor tubes; and
a cooling medium in contact with the one or more reactor tubes;
wherein
the diameter of the inner tube wall is from 20 mm to 80 mm;
the carbon monoxide hydrogenation catalyst comprises a Co loading from about 25 wt % to about 56 wt %;
the heat transfer structure comprises a network of heat conducting surfaces in conductive thermal contact with a portion of the carbon monoxide hydrogenation catalyst and wherein the heat transfer structure is in at least partial conductive thermal contact throughout the surface area of the inner tube wall containing the carbon monoxide hydrogenation catalyst; and
at least one of
a ratio of effective thermal conductivity of the heat transfer structure and the carbon monoxide hydrogenation catalyst with the inner tube wall over thermal conductivity of the carbon monoxide hydrogenation catalyst of at least about 50:1; and
a total combined surface area of the heat transfer structure and inner tube wall containing the carbon monoxide hydrogenation catalyst per volume of the carbon monoxide hydrogenation catalyst (the "SA/V") from about 500 $m^2/m^3$ to about 4000 $m^2/m^3$.

BA. The process of Paragraph AZ, wherein at least about 5% of the surface area of the inner tube wall containing the carbon monoxide hydrogenation catalyst is in conductive thermal contact with the heat transfer structure.

BB. The process of Paragraph AZ or Paragraph BA, wherein at least about 10% of surface area of the inner tube wall containing the carbon monoxide hydrogenation catalyst is in conductive thermal contact with the heat transfer structure.

BC. The process of any one of Paragraphs AZ-BB, wherein the heat transfer structure comprises steel, aluminum, copper, an alloy thereof, or a combination of any two or more thereof.

BD. The process of any one of Paragraphs AZ-BC, wherein the heat transfer structure comprises aluminum, copper, an alloy thereof, or a combination of any two or more thereof.

BE. The process of any one of Paragraphs AZ-BD, wherein the heat transfer structure comprises a combination of steel and aluminum, steel and copper, aluminum and copper, or steel, aluminum, and copper.

BF. The process of any one of Paragraphs AZ-BE, wherein the contacting step further comprises maintaining at least about 50% carbon monoxide conversion per pass in the one or more reactor tubes.

BG. The process of any one of Paragraphs AZ-BF, wherein a catalyst gas hourly space velocity of the gaseous stream in the tubular reactor is from about 5,000 $hr^{-1}$ to about 20,000 $hr^{-1}$.

BH. The process of any one of Paragraphs AZ-BG, wherein the catalyst gas hourly space velocity of the gaseous stream in the tubular reactor is at least about 5,000 $hr^{-1}$.

BI. The process of any one of Paragraphs AZ-BH, wherein the temperature of the gaseous stream at the reactor inlet is about 160° C. to about 265° C.

BJ. The process of any one of Paragraphs AZ-BI, wherein the carbon monoxide hydrogenation catalyst exhibits a conversion rate of at least 30 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 µm.

BK. The process of any one of Paragraphs AZ-BJ, wherein the carbon monoxide hydrogenation catalyst is a particulate catalyst.

BL. The process of any one of Paragraphs AZ-BK, wherein the carbon monoxide hydrogenation catalyst is a particulate catalyst having a weight average diameter from about 100 micrometers (µm) to about 1 millimeter (mm).

BM. The process of any one of Paragraphs AZ-BL, wherein the carbon monoxide hydrogenation catalyst is a particulate catalyst having an average outer surface to volume ratio from about 3.0 $mm^{-1}$ to about 50.0 $mm^{-1}$.

BN. The process of any one of Paragraphs AZ-BM, wherein the carbon monoxide hydrogenation catalyst is a particulate catalyst having a diffusion path from about 50 µm to about 500 µm.

BO. The process of any one of Paragraphs AZ-BN, wherein the carbon monoxide hydrogenation catalyst comprises a particulate Fischer-Tropsch catalyst.

BP. The process of any one of Paragraphs AZ-BO, wherein the carbon monoxide hydrogenation catalyst comprises a particulate catalyst fused to a ceramic support.

BQ. The process of any one of Paragraphs AZ-BP, wherein the synthetic product comprises hydrocarbons.

BR. The process of any one of Paragraphs AZ-BQ, wherein the synthetic product comprises $C_5+$ hydrocarbons.

BS. The process of any one of Paragraphs AZ-BR, wherein the cooling medium temperature is about 160° C. to about 265° C.

BT. The process of any one of Paragraphs AZ-BS, wherein the heat transfer structure comprises a random network of heat conducting surfaces.

BU. The process of any one of Paragraphs AZ-BT, wherein the heat transfer structure comprises an ordered network of heat conducting surfaces.

BV. The process of any one of Paragraphs AZ-BU, wherein the heat transfer structure comprises a plurality of fins extending radially from a central support.

BW. The process of any one of Paragraphs AZ-BV, wherein the heat transfer structure comprises
a first set of a plurality of fins extending radially from a central support to an internal circumferential wall of the heat transfer structure to define a first set of channels;
a second set of a plurality of fins extending radially from the circumferential wall to the inner tube wall, wherein each fin of the second set is in conductive thermal contact with the inner tube wall to define a second set of channels.

BX. The process of any one of Paragraphs AZ-BW, wherein the process further comprises introducing the gaseous stream through the reactor inlet at a pressure from about 250 psig to about 1,000 psig.

BY. The process of any one of Paragraphs AZ-BX, wherein a ratio of $H_2/CO$ in the synthesis gas from about 1.6 to about 2.0.

BZ. A tubular reactor comprising:
one or more reactor tubes including
a tube inlet;
a tube outlet located downstream of the tube inlet;
an inner tube wall defining an interior of the one or more reactor tubes;
an outer tube wall defining an exterior of the one or more reactor tubes;
a volume of a catalyst provided in at least one section within the interior of the one or more reactor tubes; and
a heat transfer structure provided within the interior of the one or more reactor tubes, the heat transfer structure being in conductive thermal contact with a portion of the catalyst and in at least partial conductive thermal contact with the inner tube wall throughout a surface area of the inner tube wall in the at least one section containing the catalyst;
a reactor inlet in fluid communication with the one or more reactor tubes; and
a reactor outlet located downstream of the reactor inlet and in fluid communication with the one or more reactor tubes,
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.

CA. A tubular reactor comprising:
one or more reactor tubes including
a tube inlet;
a tube outlet located downstream of the tube inlet;
an inner tube wall defining an interior of the one or more reactor tubes;
an outer tube wall defining an exterior of the one or more reactor tubes;
a volume of a catalyst provided in at least one section within the interior of the one or more reactor tubes; and
a plurality of heat transfer structures are provided within the interior of the one or more reactor tubes and spaced along a length of the one or more reactor tubes with respect to an adjacent heat transfer structure, the heat transfer structures being in conductive thermal contact with a portion of the catalyst and in at least partial conductive thermal contact with the inner tube wall throughout a surface area of the inner tube wall in the at least one section containing the catalyst;
a reactor inlet in fluid communication with the one or more reactor tubes; and
a reactor outlet located downstream of the reactor inlet and in fluid communication with the one or more reactor tubes,
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.

CB. The tubular reactor of Paragraph CA, wherein catalyst is provided at a location of each of the plurality of heat transfer structures, and the location of each of the plurality of heat transfer structures defines a reaction zone.

CC. The tubular reactor of Paragraph CB, wherein a same catalyst is used in each reaction zone.

CD. The tubular reactor of Paragraph CB wherein a different catalyst is used in each reaction zone.

CE. The tubular reactor of Paragraph CB or Paragraph CD, wherein at least one reaction zone differs from another reaction zone by activity, weight average diameter, average outer surface to volume ratio, diffusion path, form of catalyst, or any combination of any two or more thereof.

CF. The tubular reactor of any one of Paragraphs CA-CE, wherein a diameter of the inner tube wall is about 20 mm to 80 mm.

CG. The tubular reactor of any one of Paragraphs CA-CF, wherein at least about 5% of the surface area of the inner tube wall is in conductive thermal contact with the heat transfer structure.

CH. The tubular reactor of any one of Paragraphs CA-CG, wherein at least about 10% of surface area of the inner tube wall is in conductive thermal contact with the heat transfer structure.

CI. The tubular reactor of any one of Paragraphs CA-CH, wherein the heat transfer structure comprises steel, aluminum, copper, an alloy thereof, or a combination of any two or more thereof.

CJ. The tubular reactor of any one of Paragraphs CA-CI, wherein the heat transfer structure comprises aluminum, copper, an alloy thereof, or a combination of any two or more thereof.

CK. The tubular reactor of any one of Paragraphs CA-CJ, wherein the heat transfer structure comprises a combination of steel and aluminum, steel and copper, aluminum and copper, or steel, aluminum, and copper.

CL. The tubular reactor of any one of Paragraphs CA-CK, wherein the heat transfer structure comprises a network of heat conducting surfaces.

CM. The tubular reactor of any one of Paragraphs CA-CL, wherein the heat transfer structure comprises a random network of heat conducting surfaces.

CN. The tubular reactor of any one of Paragraphs CA-CM, wherein the heat transfer structure comprises an ordered network of heat conducting surfaces.

CO. The tubular reactor of any one of Paragraphs CA-CN, wherein the heat transfer structure comprises a plurality of fins extending radially from a central support to the inner tube wall.

CP. The tubular reactor of Paragraph CO, wherein the central support is a metal rod that is concentric with the one or more reactor tubes and extends along at least a partial length of the one or more reactor tubes.

CQ. The tubular reactor of Paragraph CO or Paragraph CP, wherein the plurality of fins extending radially from the central support to the inner tube wall are non-orthogonal to the central support.

CR. The tubular reactor of Paragraph CO or Paragraph CP, wherein the plurality of fins extending radially from the central support to the inner tube wall are orthogonal to the central support.

CS. The tubular reactor of any one of Paragraphs CA-CR, wherein the heat transfer structure comprises
a first set of fins arranged in a shape of a ring, each fin extending radially from a central support to an internal circumferential wall of the heat transfer structure to define a first set of channels; and
a second set of fins arranged in a shape of a ring, each fin extending radially from the internal circumferential wall to the inner tube wall, wherein each fin of the second set is in conductive thermal contact with the inner tube wall to define a second set of channels.

CT. The tubular reactor of Paragraph CS, wherein the heat transfer structure further comprises
an additional set of fins arranged in a shape of a ring and disposed between the first set of fins and the second set of fins; and
an additional internal circumferential wall disposed between the second set of fins and the additional set of fins.

CU. The tubular reactor of any one of Paragraphs CA-CT, wherein
the heat transfer structure comprises a metal disposed on the inner tube wall of the one or more reactor tubes.

CV. The tubular reactor of claim CU, wherein
the metal is disposed on the inner tube wall of the one or more reactor tubes via brazing or physical vapor deposition.

CW. The tubular reactor of any one of Paragraphs CA-CV, wherein
the heat transfer structure comprises a metal insert disposed within the one or more reactor tubes.

CX. The tubular reactor of any one of Paragraphs CA-CW, wherein the heat transfer structure comprises a spiral conducting surface.

CY. The tubular reactor of any one of Paragraphs CA-CX, wherein the one or more reactor tubes is cylindrical, rectangular, square or obround in shape.

CZ. The tubular reactor of any one of Paragraphs CA-CY, wherein
the tube inlet and the tube outlet have a same predetermined diameter, and
at least a portion or the reactor tube provided between the tube inlet and the tube outlet has a diameter smaller than the predetermined diameter of the tube inlet and the tube outlet.

DA. The tubular reactor of any one of Paragraphs CA-CZ, wherein the heat transfer structure is configured to be retrofit to one or more reactor tubes of an existing tubular reactor.

DB. The tubular reactor of any one of Paragraphs CA-DA, wherein
the catalyst is confined within the heat transfer structure.

DC. The tubular reactor of Paragraph DB, wherein
the heat transfer structure is a brush insert comprising a plurality of bristles, and
the catalyst is confined in voids between the bristles.

DD. The tubular reactor of Paragraph DB, wherein
the heat transfer structure is a disordered three-dimensional mesh; and
the catalyst is confined in voids within the mesh.

DE. The tubular reactor of any one of Paragraphs CA-DD, further comprising:
a retention screen provided at an inlet of at least one heat transfer structure, and
the catalyst is confined within the retention screen.

DF. The tubular reactor of any one of Paragraphs CA-DB and DE, further comprising:
a second retention screen provided at an outlet of the at least one heat transfer structure, and
the catalyst is confined within the second retention screen.

DG. The tubular reactor of any one of Paragraphs CA-DF, wherein each of the heat transfer structures can be individually removed and replaced.

DH. The tubular reactor of any one of Paragraphs CA-DG, wherein the catalyst comprises a carbon monoxide hydrogenation catalyst.

DI. The tubular reactor of Paragraph DH, wherein the carbon monoxide hydrogenation catalyst exhibits a conversion rate of at least 30 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm.

DJ. The tubular reactor of any one of Paragraphs CA-DI, wherein the catalyst comprises Co.

DK. The tubular reactor of any one of Paragraphs CA-DJ, wherein the catalyst comprises Fe.

DL. The tubular reactor of any one of Paragraphs CA-DK, wherein the catalyst is a particulate catalyst.

DM. The tubular reactor of any one of Paragraphs CA-DL, wherein the catalyst is a particulate catalyst having a weight average diameter from about 100 μm to about 1 mm.

DN. The tubular reactor of any one of Paragraphs CA-DM, wherein the catalyst is a particulate catalyst having an average outer surface to volume ratio from about 3.0 $mm^{-1}$ to about 50.0 $mm^{-1}$.

DO. The tubular reactor of any one of Paragraphs CA-DN, wherein the catalyst is a particulate catalyst having a diffusion path from about 50 μm to about 500 μm.

DP. The tubular reactor of any one of claims Paragraphs CA-DO, wherein the catalyst comprises a Co loading from about 25 wt % to about 56 wt %.

DQ. The tubular reactor of any one of Paragraphs CA-DP, wherein the catalyst comprises a particulate Fischer-Tropsch catalyst.

DR. The tubular reactor of any one of Paragraphs CA-DQ, wherein the catalyst comprises a particulate catalyst provided on a ceramic support.

DS. The tubular reactor of any one of Paragraphs CA-DR, further comprising a cooling medium in contact with the one or more reactor tubes.

DT. The tubular reactor of claim DS, wherein a temperature of the cooling medium is about 160° C. to about 265° C.

DU. A method of manufacturing a tubular reactor, the method comprising:
providing one or more reactor tubes in fluid communication with a reactor inlet and a reactor outlet located downstream of the reactor inlet, the one or more reactor tubes including
a tube inlet;
a tube outlet located downstream of the tube inlet;
an inner tube wall defining an interior of the one or more reactor tubes; and
an outer tube wall defining an exterior of the one or more reactor tubes;
disposing a volume of a catalyst provided within the interior of the one or more reactor tubes in at least one section of the one or more reactor tubes; and
disposing a heat transfer structure within the interior of the one or more reactor tubes, the heat transfer structure being in conductive thermal contact with a portion of the catalyst and in at least partial conductive thermal contact with the inner tube wall throughout a surface area of the inner tube wall in the at least one section containing the catalyst;
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.

DV. The method of Paragraph DU, wherein disposing the heat transfer structure within the interior of the one or more reactor tubes comprises
providing the heat transfer structure within a perimeter of the reactor tube, the perimeter of the reactor tube being discontinuous and having an opening extending along a length thereof;
compressing the reactor tube to seal the opening and form a seam along the length thereof; and
welding the reactor tube along the seam such that and the heat transfer structure is in at least partial conductive thermal contact with the inner tube wall throughout the surface area of the inner tube wall.

DW. The method of Paragraph DU, wherein
the heat transfer structure comprises
a first set of fins arranged in a shape of a ring, each fin extending radially from a central support to an internal circumferential wall of the heat transfer structure to define a first set of channels; and a second set of fins arranged in a shape of a ring, each fin extending radially from the internal circumferential wall to the inner tube wall, wherein each fin of the second set is in conductive thermal contact with the inner tube wall to define a second set of channels; and disposing the heat transfer structure within the interior of the one or more reactor tubes comprises providing the second set of fins within a perimeter of the reactor tube, the perimeter of the reactor tube being discontinuous and having an opening extending along a length thereof;

compressing the reactor tube to seal the opening and form a seam along the length thereof; and welding the reactor tube along the seam such that and the second set of fins is in at least partial conductive thermal contact with the inner tube wall throughout the surface area of the inner tube wall.

DX. The method of Paragraph DW, wherein disposing the heat transfer structure within the interior of the one or more reactor tubes further comprises providing the second set of fins within the reactor tube prior to the first set of fins; and inserting the internal circumferential wall and the first set of fins into a central opening defined by the ring of the second set of fins, the internal circumferential wall of the heat transfer structure comprising a shim having a first end in contact with at least one fin in the first set of fins, and a second end overlapping the first end along a perimeter of the internal circumferential wall; and upon insertion of the internal circumferential wall and the first set of fins into the central opening, the internal circumferential wall expands, and the internal circumferential wall is held in place by friction fit between the first and second set of fins.

DY. The method of Paragraph DX, wherein upon insertion of the internal circumferential wall and the first set of fins into the central opening, the internal circumferential wall expands such that the first end and the second end do not overlap.

DZ. The method of Paragraph DX, wherein upon insertion of the internal circumferential wall and the first set of fins into the central opening, the internal circumferential wall expands such that a degree of overlap between the first end and the second end prior to insertion is less than a degree of overlap between the first end and the second end after insertion.

EA. The method of Paragraph DU, wherein the heat transfer structure comprises a first set of fins extending radially from a central support to an internal circumferential wall of the heat transfer structure to define a first set of channels; and a second set of fins extending radially from the internal circumferential wall to the inner tube wall, wherein each fin of the second set is in conductive thermal contact with the inner tube wall to define a second set of channels; and disposing the heat transfer structure within the interior of the one or more reactor tubes comprises providing the second set of fins within the reactor tube prior to the first set of fins; and inserting the internal circumferential wall and the first set of fins into a central opening defined by the ring of the second set of fins, the internal circumferential wall of the heat transfer structure comprising a shim having a first end in contact with at least one fin in the first set of fins, and a second end overlapping the first end along a perimeter of the internal circumferential wall; and upon insertion of the internal circumferential wall and the first set of fins into the central opening, the internal circumferential wall expands, and the internal circumferential wall is held in place by friction fit between the first and second set of fins.

EB. The method of Paragraph DU, wherein the one or more reactor tubes has an internal diameter;

the heat transfer structure comprises a metal insert having an external diameter smaller than the internal diameter of the one or more reactor tubes; and disposing the heat transfer structure within the interior of the one or more reactor tubes comprises inserting the metal insert within the one or more reactor tubes;

sealing one of the tube inlet and the tube outlet; and applying a pressure to an unsealed end of the reactor tube to expand the metal insert such that the metal insert is in at least partial conductive thermal contact with the inner tube wall of the one or more reactor tubes throughout the surface area of the inner tube wall.

EC. The method of Paragraph EB, wherein the metal insert is in an at least partially collapsed state when inserted within the one or more reactor tubes; and the metal insert is expanded to a shape corresponding to a shape of the one or more reactor tubes due to the applied pressure.

ED. The method of Paragraph DU, wherein disposing the heat transfer structure within the interior of the one or more reactor tubes comprises inserting the heat transfer structure within the reactor tube; and rotating the heat transfer structure to lock the heat transfer structure in place.

EE. The method of Paragraph DU, wherein disposing the heat transfer structure within the interior of the one or more reactor tubes comprises providing a plurality of fins arranged in a shape of a ring having a central opening therein;

inserting the ring within the reactor tube, and subsequently inserting a central support with the central space of the ring, wherein insertion of the central support causes the ring to expand such that the plurality of fins are pushed against the inner tube wall and held in place under compression between the central support and the inner tube wall.

EF. The method of any one of Paragraphs DU-EE, further comprising:

providing a plurality of heat transfer structures within the interior of the one or more reactor tubes, the plurality of heat transfer structures being spaced along a length of the one or more reactor tubes with respect to an adjacent heat transfer structure.

EG. A process for the production of an alkylene oxide, the process comprising contacting in a tubular reactor a gaseous stream comprising a $C_2$-$C_4$ alkylene and an oxygen source with an alkylene oxidation catalyst to produce a synthetic product comprising the alkylene oxide;

wherein the tubular reactor comprises a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the alkylene oxidation catalyst within the reactor tube;

a reactor outlet located downstream of the reactor inlet in fluid communication with the one or more reactor tubes; and a cooling medium in contact with the one or more reactor tubes;

wherein the diameter of the inner tube wall is from about 20 mm to about 80 mm;

the gaseous stream comprises one or more of the following:

(1) a $C_2$-$C_4$ alkylene to oxygen source mole ratio from about 0.2:1 to about 4:1;

(2) a diluent concentration less than about 50% by volume; and (3) a concentration of the oxygen source of at least about 8% by volume;

the heat transfer structure comprises a network of heat conducting surfaces in conductive thermal contact with a portion of the volume of alkylene oxidation catalyst and wherein the heat transfer structure is in at least partial conductive thermal contact throughout the surface area of the inner tube wall containing the alkylene oxidation catalyst; and at least one of a ratio of effective thermal conductivity of the heat transfer structure and the alkylene oxidation catalyst with the inner tube wall over thermal conductivity of the alkylene oxidation catalyst of at least about 50:1; and a total combined surface area of the heat transfer structure and inner tube wall containing the alkylene oxidation catalyst per volume of the alkylene oxidation catalyst (the "SA/V") from about 500 $m^2/m^3$ to about 4000 $m^2/m^3$.

EH. The process of Paragraph EG, wherein at least about 5% of surface area of the inner tube wall containing the alkylene oxidation catalyst is in conductive thermal contact with the heat transfer structure.

EI. The process of Paragraph EG or Paragraph EH, wherein at least about 10% of surface area of the inner tube wall containing the alkylene oxidation catalyst is in conductive thermal contact with the heat transfer structure.

EJ. The process of any one of Paragraphs EH-EI, wherein the heat transfer structure comprises steel, aluminum, copper, an alloy thereof, or a combination of any two or more thereof.

EK. The process of any one of Paragraphs EH-EJ, wherein the heat transfer structure comprises aluminum, copper, an alloy thereof, or a combination of any two or more thereof.

EL. The process of any one of Paragraphs EH-EK, wherein the heat transfer structure comprises a combination of steel and aluminum, steel and copper, aluminum and copper, or steel, aluminum, and copper.

EM. The process of any one of Paragraphs EH-EL, wherein the contacting step further comprises maintaining at least about 10% alkylene conversion per pass in the one or more reactor tubes.

EN. The process of any one of Paragraphs EH-EM, wherein an catalyst gas hourly space velocity of the gaseous stream in the tubular reactor is from about 100 $hr^{-1}$ to about 2,000,000 $hr^{-1}$.

EO. The process of any one of Paragraphs EH-EN, wherein the catalyst gas hourly space velocity of the gaseous stream in the tubular reactor is at least about 5,000 $hr^{-1}$.

EP. The process of any one of Paragraphs EH-EO, wherein the temperature of the gaseous stream at the reactor inlet is about 150° C. to about 1,000° C.

EQ. The process of any one of Paragraphs EH-EP, wherein the $C_2$-$C_4$ alkylene comprises one or more of ethylene and propylene.

ER. The process of any one of Paragraphs EH-EQ, wherein the alkylene oxidation catalyst comprises Ag.

ES. The process of any one of Paragraphs EH-ER, wherein the alkylene oxidation catalyst is a particulate catalyst.

ET. The process of any one of Paragraphs EH-ES, wherein the alkylene oxidation catalyst is a particulate catalyst having a weight average diameter from about 1 micrometer (μm) to about 1 millimeter (mm).

EU. The process of any one of Paragraphs EH-ET, wherein the alkylene oxidation catalyst is a particulate catalyst having an average outer surface to volume ratio from about 3.0 $mm^{-1}$ to about 50.0 $mm^{-1}$.

EV. The process of any one of Paragraphs EH-EU, wherein the alkylene oxidation catalyst is a particulate catalyst having a diffusion path from about 50 μm to about 500 μm.

EW. The process of any one of Paragraphs EH-EV, wherein the alkylene oxidation catalyst comprises a Ag loading from about 10 wt % to about 50 wt %.

EX. The process of any one of Paragraphs EH-EW, wherein the cooling medium temperature is about −70° C. to about 350° C.

EY. The process of any one of Paragraphs EH-EX, wherein a mole ratio of the $C_2$-$C_4$ alkylene to oxygen source is from about 0.2:1 to about 4:1.

EZ. The process of any one of Paragraphs EH-EY, wherein the heat transfer structure comprises a random network of heat conducting surfaces.

FA. The process of any one of Paragraphs EH-EZ, wherein the heat transfer structure comprises an ordered network of heat conducting surfaces.

FB. The process of any one of Paragraphs EH-FA, wherein the heat transfer structure comprises a plurality of fins extending radially from a central support.

FC. The process of any one of Paragraphs EH-FB, wherein the heat transfer structure comprises a first set of a plurality of fins extending radially from a central support to an internal circumferential wall of the heat transfer structure to define a first set of channels;

a second set of a plurality of fins extending radially from the circumferential wall to the inner tube wall, wherein each fin of the second set is in conductive thermal contact with the inner tube wall to define a second set of channels.

FD. A tubular reactor comprising:

one or more reactor tubes including a tube inlet;

a tube outlet located downstream of the tube inlet;

an inner tube wall defining an interior of the one or more reactor tubes;

an outer tube wall defining an exterior of the one or more reactor tubes;

a volume of a catalyst provided in at least one section within the interior of the one or more reactor tubes; and a heat transfer structure provided within the interior of the one or more reactor tubes, the heat transfer structure being in conductive thermal contact with a portion of the catalyst and in at least partial conductive thermal contact with the inner tube wall throughout a surface area of the inner tube wall in the at least one section containing the catalyst;
a reactor inlet in fluid communication with the one or more reactor tubes; and
a reactor outlet located downstream of the reactor inlet and in fluid communication with the one or more reactor tubes,
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.

FE. A tubular reactor comprising:
one or more reactor tubes including
a tube inlet;
a tube outlet located downstream of the tube inlet;
an inner tube wall defining an interior of the one or more reactor tubes;
an outer tube wall defining an exterior of the one or more reactor tubes;
a volume of a catalyst provided in at least one section within the interior of the one or more reactor tubes; and
a plurality of heat transfer structures are provided within the interior of the one or more reactor tubes and spaced along a length of the one or more reactor tubes with respect to an adjacent heat transfer structure, the heat transfer structures being in conductive thermal contact with a portion of the catalyst and in at least partial conductive thermal contact with the inner tube wall throughout a surface area of the inner tube wall in the at least one section containing the catalyst;
a reactor inlet in fluid communication with the one or more reactor tubes; and
a reactor outlet located downstream of the reactor inlet and in fluid communication with the one or more reactor tubes,
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.

FF. The tubular reactor of Paragraph FE, wherein catalyst is provided at a location of each of the plurality of heat transfer structures, and the location of each of the plurality of heat transfer structures defines a reaction zone.

FG. The tubular reactor of Paragraph FF, wherein a same catalyst is used in each reaction zone.

FH. The tubular reactor of Paragraph FF, wherein a different catalyst is used in each reaction zone.

FI. The tubular reactor of Paragraph FF or Paragraph FH, wherein at least one reaction zone differs from another reaction zone by activity, weight average diameter, average outer surface to volume ratio, diffusion path, form of catalyst, or any combination of any two or more thereof.

FJ. The tubular reactor of any one of Paragraphs FD-FI, wherein a diameter of the inner tube wall is about 20 mm to 80 mm.

FK. The tubular reactor of any one of Paragraphs FD-FJ, wherein at least about 5% of the surface area of the inner tube wall is in conductive thermal contact with the heat transfer structure.

FL. The tubular reactor of any one of Paragraphs FD-FK, wherein at least about 10% of surface area of the inner tube wall is in conductive thermal contact with the heat transfer structure.

FM. The tubular reactor of any one of Paragraphs FD-FL, wherein the heat transfer structure comprises steel, aluminum, copper, an alloy thereof, or a combination of any two or more thereof.

FN. The tubular reactor of any one of Paragraphs FD-FM, wherein the heat transfer structure comprises aluminum, copper, an alloy thereof, or a combination of any two or more thereof.

FO. The tubular reactor of any one of Paragraphs FD-FN, wherein the heat transfer structure comprises a combination of steel and aluminum, steel and copper, aluminum and copper, or steel, aluminum, and copper.

FP. The tubular reactor of any one of Paragraphs FD-FO, wherein the heat transfer structure comprises a network of heat conducting surfaces.

FQ. The tubular reactor of any one of Paragraphs FD-FP, wherein the heat transfer structure comprises a random network of heat conducting surfaces.

FR. The tubular reactor of any one of Paragraphs FD-FQ, wherein the heat transfer structure comprises an ordered network of heat conducting surfaces.

FS. The tubular reactor of any one of Paragraphs FD-FR, wherein the heat transfer structure comprises a plurality of fins extending radially from a central support to the inner tube wall.

FT. The tubular reactor of Paragraph FS, wherein the central support is a metal rod that is concentric with the one or more reactor tubes and extends along at least a partial length of the one or more reactor tubes.

FU. The tubular reactor of Paragraph FS or Paragraph FT, wherein the plurality of fins extending radially from the central support to the inner tube wall are non-orthogonal to the central support.

FV. The tubular reactor of Paragraph FS or Paragraph FT, wherein the plurality of fins extending radially from the central support to the inner tube wall are orthogonal to the central support.

FW. The tubular reactor of any one of Paragraphs FD-FV, wherein the heat transfer structure comprises
a first set of fins arranged in a shape of a ring, each fin extending radially from a central support to an internal circumferential wall of the heat transfer structure to define a first set of channels; and
a second set of fins arranged in a shape of a ring, each fin extending radially from the internal circumferential wall to the inner tube wall, wherein each fin of the second set is in conductive thermal contact with the inner tube wall to define a second set of channels.

FX. The tubular reactor of Paragraph FW, wherein the heat transfer structure further comprises
an additional set of fins arranged in a shape of a ring and disposed between the first set of fins and the second set of fins; and an additional internal circumferential wall disposed between the second set of fins and the additional set of fins.
FY. The tubular reactor of any one of Paragraphs FD-FX, wherein
the heat transfer structure comprises a metal disposed on the inner tube wall of the one or more reactor tubes.
FZ. The tubular reactor of Paragraph FY, wherein
the metal is disposed on the inner tube wall of the one or more reactor tubes via brazing or physical vapor deposition.
GA. The tubular reactor of any one of Paragraphs FD-FZ, wherein
the heat transfer structure comprises a metal insert disposed within the one or more reactor tubes.
GB. The tubular reactor of any one of Paragraphs FD-GA, wherein the heat transfer structure comprises a spiral conducting surface.
GC. The tubular reactor of any one of Paragraphs FD-GB, wherein the one or more reactor tubes is cylindrical, rectangular, square or obround in shape.
GD. The tubular reactor of any one of Paragraphs FD-GC, wherein
the tube inlet and the tube outlet have a same predetermined diameter, and
at least a portion or the reactor tube provided between the tube inlet and the tube outlet has a diameter smaller than the predetermined diameter of the tube inlet and the tube outlet.
GE. The tubular reactor of any one of Paragraphs FD-GD, wherein the heat transfer structure is configured to be retrofit to one or more reactor tubes of an existing tubular reactor.
GF. The tubular reactor of any one of Paragraphs FD-GE, wherein
the catalyst is confined within the heat transfer structure.
GG. The tubular reactor of Paragraph GF, wherein
the heat transfer structure is a brush insert comprising a plurality of bristles, and
the catalyst is confined in voids between the bristles.
GH. The tubular reactor of Paragraph GF, wherein
the heat transfer structure is a disordered three-dimensional mesh; and
the catalyst is confined in voids within the mesh.
GI. The tubular reactor of any one of Paragraphs FD-GH, further comprising:
a retention screen provided at an inlet of at least one heat transfer structure, and
the catalyst is confined within the retention screen.
GJ. The tubular reactor of any one of Paragraphs FD-GI, further comprising:
a second retention screen provided at an outlet of the at least one heat transfer structure, and
the catalyst is confined within the second retention screen.
GK. The tubular reactor of any one of Paragraphs FD-GJ, wherein each of the heat transfer structures can be individually removed and replaced.
GL. The tubular reactor of any one of Paragraphs FD-GK, wherein the catalyst comprises an alkylene oxidation catalyst.
GM. The tubular reactor of any one of Paragraphs FD-GL, wherein the catalyst comprises an alkylene oxidation catalyst, and wherein the alkylene oxidation catalyst comprises Ag.
GN. The tubular reactor of any one of Paragraphs FD-GM, wherein the catalyst comprises an alkylene oxidation catalyst, and wherein the alkylene oxidation catalyst comprises a Ag loading from about 10 wt % to about 50 wt %.
GO. The tubular reactor of any one of Paragraphs FD-GN, wherein the catalyst is a particulate catalyst.
GP. The tubular reactor of any one of Paragraphs FD-GO, wherein the catalyst is a particulate catalyst having a weight average diameter from about 100 µm to about 1 mm.
GQ. The tubular reactor of any one of Paragraphs FD-GP, wherein the catalyst is a particulate catalyst having an average outer surface to volume ratio from about 3.0 $mm^{-1}$ to about 50.0 $mm^{-1}$.
GR. The tubular reactor of any one of Paragraphs FD-GQ, wherein the catalyst is a particulate catalyst having a diffusion path from about 50 µm to about 500 µm.
GS. The tubular reactor of any one of Paragraphs FD-GR, further comprising a cooling medium in contact with the one or more reactor tubes.
GT. The tubular reactor of any one of Paragraphs FD-GS, wherein a temperature of the cooling medium is about −70° C. to about 350° C.
GU. A method of manufacturing a tubular reactor, the method comprising:
providing one or more reactor tubes in fluid communication with a reactor inlet and a reactor outlet located downstream of the reactor inlet, the one or more reactor tubes including
a tube inlet;
a tube outlet located downstream of the tube inlet;
an inner tube wall defining an interior of the one or more reactor tubes; and
an outer tube wall defining an exterior of the one or more reactor tubes;
disposing a volume of a catalyst provided within the interior of the one or more reactor tubes in at least one section of the one or more reactor tubes; and
disposing a heat transfer structure within the interior of the one or more reactor tubes, the heat transfer structure being in conductive thermal contact with a portion of the catalyst and in at least partial conductive thermal contact with the inner tube wall throughout a surface area of the inner tube wall in the at least one section containing the catalyst;
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 $m^2/m^3$ to about 4000 $m^2/m^3$.
GV. The method of Paragraph GU, wherein disposing the heat transfer structure within the interior of the one or more reactor tubes comprises
providing the heat transfer structure within a perimeter of the reactor tube, the perimeter of the reactor tube being discontinuous and having an opening extending along a length thereof;
compressing the reactor tube to seal the opening and form a seam along the length thereof; and
welding the reactor tube along the seam such that and the heat transfer structure is in at least partial conductive thermal contact with the inner tube wall throughout the surface area of the inner tube wall.

GW. The method of Paragraph GU, wherein
 the heat transfer structure comprises
  a first set of fins arranged in a shape of a ring, each fin extending radially from a central support to an internal circumferential wall of the heat transfer structure to define a first set of channels; and
  a second set of fins arranged in a shape of a ring, each fin extending radially from the internal circumferential wall to the inner tube wall, wherein each fin of the second set is in conductive thermal contact with the inner tube wall to define a second set of channels; and
 disposing the heat transfer structure within the interior of the one or more reactor tubes comprises
  providing the second set of fins within a perimeter of the reactor tube, the perimeter of the reactor tube being discontinuous and having an opening extending along a length thereof;
  compressing the reactor tube to seal the opening and form a seam along the length thereof; and
  welding the reactor tube along the seam such that and the second set of fins is in at least partial conductive thermal contact with the inner tube wall throughout the surface area of the inner tube wall.

GX. The method of Paragraph GW, wherein
 disposing the heat transfer structure within the interior of the one or more reactor tubes further comprises
  providing the second set of fins within the reactor tube prior to the first set of fins; and
  inserting the internal circumferential wall and the first set of fins into a central opening defined by the ring of the second set of fins, the internal circumferential wall of the heat transfer structure comprising a shim having a first end in contact with at least one fin in the first set of fins, and a second end overlapping the first end along a perimeter of the internal circumferential wall; and
  upon insertion of the internal circumferential wall and the first set of fins into the central opening, the internal circumferential wall expands, and the internal circumferential wall is held in place by friction fit between the first and second set of fins.

GY. The method of Paragraph GX, wherein
 upon insertion of the internal circumferential wall and the first set of fins into the central opening, the internal circumferential wall expands such that the first end and the second end do not overlap.

GZ. The method of Paragraph GX, wherein
 upon insertion of the internal circumferential wall and the first set of fins into the central opening, the internal circumferential wall expands such that a degree of overlap between the first end and the second end prior to insertion is less than a degree of overlap between the first end and the second end after insertion.

HA. The method of Paragraph GU, wherein
 the heat transfer structure comprises
  a first set of fins extending radially from a central support to an internal circumferential wall of the heat transfer structure to define a first set of channels; and
  a second set of fins extending radially from the internal circumferential wall to the inner tube wall, wherein each fin of the second set is in conductive thermal contact with the inner tube wall to define a second set of channels; and
 disposing the heat transfer structure within the interior of the one or more reactor tubes comprises
  providing the second set of fins within the reactor tube prior to the first set of fins; and
  inserting the internal circumferential wall and the first set of fins into a central opening defined by the ring of the second set of fins, the internal circumferential wall of the heat transfer structure comprising a shim having a first end in contact with at least one fin in the first set of fins, and a second end overlapping the first end along a perimeter of the internal circumferential wall; and
  upon insertion of the internal circumferential wall and the first set of fins into the central opening, the internal circumferential wall expands, and the internal circumferential wall is held in place by friction fit between the first and second set of fins.

HB. The method of Paragraph GU, wherein
 the one or more reactor tubes has an internal diameter;
 the heat transfer structure comprises a metal insert having an external diameter smaller than the internal diameter of the one or more reactor tubes; and
 disposing the heat transfer structure within the interior of the one or more reactor tubes comprises
  inserting the metal insert within the one or more reactor tubes;
  sealing one of the tube inlet and the tube outlet; and
  applying a pressure to an unsealed end of the reactor tube to expand the metal insert such that the metal insert is in at least partial conductive thermal contact with the inner tube wall of the one or more reactor tubes throughout the surface area of the inner tube wall.

HC. The method of Paragraph HB, wherein
 the metal insert is in an at least partially collapsed state when inserted within the one or more reactor tubes; and
 the metal insert is expanded to a shape corresponding to a shape of the one or more reactor tubes due to the applied pressure.

HD. The method of Paragraph GU, wherein disposing the heat transfer structure within the interior of the one or more reactor tubes comprises
 inserting the heat transfer structure within the reactor tube; and
 rotating the heat transfer structure to lock the heat transfer structure in place.

HE. The method of Paragraph GU, wherein disposing the heat transfer structure within the interior of the one or more reactor tubes comprises
 providing a plurality of fins arranged in a shape of a ring having a central opening therein;
 inserting the ring within the reactor tube, and
 subsequently inserting a central support with the central space of the ring,
 wherein insertion of the central support causes the ring to expand such that the plurality of fins are pushed against the inner tube wall and held in place under compression between the central support and the inner tube wall.

HF. The method of any one of Paragraphs GU-HE, further comprising:
 providing a plurality of heat transfer structures within the interior of the one or more reactor tubes, the plurality of heat transfer structures being spaced along a length of the one or more reactor tubes with respect to an adjacent heat transfer structure.

Other embodiments are set forth in the following claims, along with the full scope of equivalents to which such claims are entitled.

What is claimed is:

1. A process for the conversion of synthesis gas, the process comprising contacting in a tubular reactor a gaseous stream comprising synthesis gas with a carbon monoxide hydrogenation catalyst to produce a synthetic product;

wherein the tubular reactor comprises a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube;

a reactor outlet located downstream of the reactor inlet in fluid communication with the one or more reactor tubes; and a cooling medium in contact with the one or more reactor tubes; wherein the diameter of the inner tube wall is from 20 mm to 80 mm; the carbon monoxide hydrogenation catalyst exhibits a conversion rate of at least 30 millimoles CO per mL of catalyst per hour when tested by reacting a stream comprising 30 vol. % inert, gas and a ratio of $H_2/CO$ of 1.84 at a temperature of 205° C. and a pressure of 348 psig with a catalyst gas hourly space velocity of 20,000 $hr^{-1}$ using a particulate form of the carbon monoxide hydrogenation catalyst with a weight average diameter of less than 65 μm;

the heat transfer structure comprises a network of heat conducting surfaces in conductive thermal contact with a portion of the carbon monoxide hydrogenation catalyst and wherein the heat transfer structure is in at least partial conductive thermal contact throughout the surface area of the inner tube wall containing the carbon monoxide hydrogenation catalyst; and at least one of a ratio of effective thermal conductivity of the heat transfer structure and the carbon monoxide hydrogenation catalyst with the inner tube wall over thermal conductivity of the carbon monoxide hydrogenation catalyst of at least about 50:1; and a total combined surface area of the heat transfer structure and inner tube wall containing the carbon monoxide hydrogenation catalyst per volume of the carbon monoxide hydrogenation catalyst (the "SA/V") from about 500 $m^2/m^3$ to about 4000 $m^2/m^3$.

2. The process of claim 1, wherein at least about 5% of the surface area of the inner tube wall containing the carbon monoxide hydrogenation catalyst is in conductive thermal contact with the heat transfer structure.

3. The process of claim 1, wherein the heat transfer structure comprises steel, aluminum, copper, an alloy thereof, or a combination of any two or more thereof.

4. The process of claim 1, wherein the contacting step further comprises maintaining at least about 50% carbon monoxide conversion per pass in the one or more reactor tubes.

5. The process of claim 1, wherein a catalyst gas hourly space velocity of the gaseous stream in the tubular reactor is from about 5,000 $hr^{-1}$ to about 20,000 $hr^{-1}$.

6. The process of claim 1, wherein the carbon monoxide hydrogenation catalyst is a particulate catalyst having a weight average diameter from about 100 micrometers (μm) to about 1 millimeter (mm).

7. The process of claim 1, wherein the carbon monoxide hydrogenation catalyst is a particulate catalyst having an average outer surface to volume ratio from about 3.0 $mm^{-1}$ to about 50.0 $mm^{-1}$.

8. The process of claim 1, wherein the carbon monoxide hydrogenation catalyst comprises a particulate Fischer-Tropsch catalyst.

9. The process of claim 1, wherein the heat transfer structure comprises a random network of heat conducting surfaces.

10. The process of claim 1, wherein the heat transfer structure comprises an ordered network of heat conducting surfaces.

11. The process of claim 1, wherein the heat transfer structure comprises a plurality of fins extending radially from a central support.

12. The process of claim 1, wherein the heat transfer structure comprises a first set of a plurality of fins extending radially from a central support to an internal circumferential wall of the heat transfer structure to define a first set of channels;

a second set of a plurality of fins extending radially from the circumferential wall to the inner tube wall, wherein each fin of the second set is in conductive thermal contact with the inner tube wall to define a second set of channels.

13. A process for the conversion of synthesis gas, the process comprising contacting in a tubular reactor a gaseous stream comprising synthesis gas with a particulate Fischer-Tropsch catalyst comprising Co to produce a synthetic product comprising hydrocarbons, wherein the tubular reactor comprises a reactor inlet in fluid communication with one or more reactor tubes wherein each reactor tube comprises a tube inlet, a tube outlet located downstream of the tube inlet, an inner tube wall, an outer tube wall, a heat transfer structure within the reactor tube, and a volume of the particulate Fischer-Tropsch catalyst within the reactor tube;

a reactor outlet located downstream of the reactor inlet in fluid communication with the one or more reactor tubes; and a cooling medium in contact with the one or more reactor tubes; wherein the diameter of the inner tube wall is from 20 mm to 50 mm and each reactor tube comprises a length containing the particulate Fischer-Tropsch catalyst that is less than about 5 meters;

at least about 5% of surface area of the inner tube wall containing the carbon monoxide hydrogenation catalyst is in conductive thermal contact with the heat transfer structure;

the particulate Fischer-Tropsch catalyst exhibits a conversion rate of at least 30 millimoles CO per mL of catalyst per hour when tested by reacting a stream comprising 30 vol. % inert gas and a ratio of $H_2/CO$ of 1.84 at a temperature of 205° C. and a pressure of 348 psig with a catalyst gas hourly space velocity of 20,000 $hr^{-1}$ using particulate Fischer-Tropsch catalyst with a weight average diameter of less than 65 μm;

the heat transfer structure comprises a network of heat conducting surfaces in conductive thermal contact with a portion of the volume of carbon monoxide hydrogenation catalyst and wherein the heat transfer structure is in at least partial conductive thermal contact throughout the surface area of the inner tube wall containing the particulate Fischer-Tropsch catalyst; and at least one of a ratio of effective thermal conductivity of the heat transfer structure and the particulate Fischer-Tropsch catalyst with the inner tube wall over thermal conductivity of the particulate Fischer-Tropsch catalyst of at least about 50:1; and a total combined surface area of the heat transfer structure and inner tube wall containing the particulate Fischer-Tropsch catalyst per volume of the particulate Fischer-Tropsch catalyst (the "SA/V") from about 500 m$^2$/m$^3$ to about 4000 m$^2$/m$^3$;

the process further comprising introducing the gaseous stream through the reactor inlet at a pressure from about 250 psig to about 1,000 psig with a ratio of H$_2$/CO in the synthesis gas from about 1.6 to about 2.0.

14. A process for the conversion of synthesis gas, the process comprising contacting in a tubular reactor a gaseous stream comprising synthesis gas with a carbon monoxide hydrogenation catalyst to produce a synthetic product;

wherein the tubular reactor comprises
a reactor inlet in fluid communication with one or more reactor tubes wherein each reactor tube comprises a tube inlet, a tube outlet located downstream of the tube inlet, an inner tube wall comprising a surface area, an outer tube wall, a heat transfer structure within the reactor tube, and a volume of the carbon monoxide hydrogenation catalyst within the reactor tube;
a reactor outlet located downstream of the reactor inlet in fluid communication with the one or more reactor tubes; and
a cooling medium in contact with the one or more reactor tubes;
wherein
the diameter of the inner tube wall is from 20 mm to 80 mm;
the carbon monoxide hydrogenation catalyst comprises a Co loading from about 25 wt % to about 56 wt %;
the heat transfer structure comprises a network of heat conducting surfaces in conductive thermal contact with a portion of the carbon monoxide hydrogenation catalyst and wherein the heat transfer structure is in at least partial conductive thermal contact throughout the surface area of the inner tube wall containing the carbon monoxide hydrogenation catalyst; and
at least one of
a ratio of effective thermal conductivity of the heat transfer structure and the carbon monoxide hydrogenation catalyst with the inner tube wall over thermal conductivity of the carbon monoxide hydrogenation catalyst of at least about 50:1; and
a total combined surface area of the heat transfer structure and inner tube wall containing the carbon monoxide hydrogenation catalyst per volume of the carbon monoxide hydrogenation catalyst (the "SA/V") from about 500 m$^2$/m$^3$ to about 4000 m$^2$/m$^3$.

15. A tubular reactor comprising:
one or more reactor tubes including
a tube inlet;
a tube outlet located downstream of the tube inlet;
an inner tube wall defining an interior of the one or more reactor tubes;
an outer tube wall defining an exterior of the one or more reactor tubes;
a volume of a catalyst provided in at least one section within the interior of the one or more reactor tubes; and
a heat transfer structure provided within the interior of the one or more reactor tubes, the heat transfer structure being in conductive thermal contact with a portion of the catalyst and in at least partial conductive thermal contact with the inner tube wall throughout a surface area of the inner tube wall in the at least one section containing the catalyst;
a reactor inlet in fluid communication with the one or more reactor tubes; and a reactor outlet located downstream of the reactor inlet and in fluid communication with the one or more reactor tubes,
wherein the tubular reactor satisfies at least one of the following conditions:
a ratio of an effective thermal conductivity of the heat transfer structure and the catalyst with the inner tube wall to a thermal conductivity of the catalyst ($k_{eff}/k_{cat}$) is at least 50:1, or
a total combined surface area of the heat transfer structure and inner tube wall containing the catalyst per volume of the catalyst (the "SA/V") is about 500 m$^2$/m$^3$ to about 4000 m$^2$/m$^3$.

* * * * *